US012600799B2

(12) United States Patent
Görlich et al.

(10) Patent No.: US 12,600,799 B2
(45) Date of Patent: Apr. 14, 2026

(54) ANTI-IgG NANOBODIES

(71) Applicant: MAX-PLANCK-GESELLSCHAFT ZUR FÖRDERUNG DER WISSENSCHAFTEN E.V., Munich (DE)

(72) Inventors: Dirk Görlich, Göttingen (DE); Tino Pleiner, Göttingen (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 1234 days.

(21) Appl. No.: 16/754,847

(22) PCT Filed: Oct. 11, 2018

(86) PCT No.: PCT/EP2018/077751
§ 371 (c)(1),
(2) Date: Apr. 9, 2020

(87) PCT Pub. No.: WO2019/072977
PCT Pub. Date: Apr. 18, 2019

(65) Prior Publication Data
US 2024/0018267 A1      Jan. 18, 2024

(30) Foreign Application Priority Data
Oct. 11, 2017      (EP) ...................................... 17195992

(51) Int. Cl.
*C07K 16/42*          (2006.01)

(52) U.S. Cl.
CPC .......... *C07K 16/42* (2013.01); *C07K 2317/22* (2013.01); *C07K 2317/33* (2013.01); *C07K 2317/569* (2013.01); *C07K 2317/92* (2013.01)

(58) Field of Classification Search
CPC ........................... C07K 16/42; C07K 2317/22; C07K 2317/33; C07K 2317/569; C07K 2317/92
See application file for complete search history.

(56) References Cited

FOREIGN PATENT DOCUMENTS

| | | | |
|---|---|---|---|
| WO | 01/44301 | A1 | 6/2001 |
| WO | 02/48193 | A2 | 6/2002 |
| WO | 02/48193 | A3 | 6/2002 |
| WO | 2009/011572 | A1 | 1/2009 |

OTHER PUBLICATIONS

De Genst et al., "Antibody repertoire development in camelids," Dev. Comp. Immunol. 2006, vol. 30, pp. 187-198.*
Sircar et al., "Analysis and Modeling of the Variable Region of Camelid Single-Domain Antibodies," J. Immunol., 2011, vol. 186, pp. 6357-6367.*
Zabetakis et al., "Contributions of the complementarity determining regions to the thermal stability of a single-domain antibody," PLoS One, 2013, 8(10):e77678, 7 pages.*
Rudikoff et al., "Single amino acid substitution altering antigen-binding specificity," Proc. Natl. Acad. Sci. USA, 1982, vol. 79, pp. 1979-1983.*
Zhu et al., "50 Years of Antibody Numbering Schemes: A Statistical and Structural Evaluation Reveals Key Differences and Limitations," Antibodies, 2024, vol. 13(4):99, pp. 1-23.*
Arbabi Ghahroudi, M., Desmyter, A., Wyns, L., Hamers, R. & Muyldermans, S. (1997) Selection and identification of single domain antibody fragments from camel heavy-chain antibodies. FEBS Lett, 414, 521-526.
Balzarotti, F., Eilers, Y., Gwosch, K.C., Gynna, A.H., Westphal, V., Stefani, F.D., Elf, J. & Hell, S.W. (2017) Nanometer resolution imaging and tracking of fluorescent molecules with minimal photon fluxes. Science, 355, 606-612.
Bates, M., Dempsey, G.T., Chen, K.H. & Zhuang, X. (2012) Multicolor super-resolution fluorescence imaging via multi-parameter fluorophore detection. Chemphyschem, 13, 99-107.
Bates, M., Huang, B., Dempsey, G.T. & Zhuang, X. (2007) Multicolor super-resolution imaging with photo-switchable fluorescent probes. Science, 317, 1749-1753.
Bradbury, A. & Pluckthun, A. (2015a) Reproducibility: Standardize antibodies used in research. Nature, 518, 27-29.
Bradbury, A.R. & Pluckthun, A. (2015b) Getting to reproducible antibodies: the rationale for sequenced recombinant characterized reagents. Protein Eng Des Sel, 28, 303-305.
Cordes, V.C., Reidenbach, S. & Franke, W.W. (1995) High content of a nuclear pore complex protein in cytoplasmic annulate lamellae of Xenopus oocytes. Eur J Cell Biol, 68, 240-255.
Cordes, V.C., Reidenbach, S., Rackwitz, H.R. & Franke, W.W. (1997) Identification of protein p270/Tpr as a constitutive component of the nuclear pore complex-attached intranuclear filaments. J Cell Biol, 136, 515-529.
Desmyter, A., Spinelli, S., Roussel, A. & Cambillau, C. (2015) Camelid nanobodies: killing two birds with one stone. Curr Opin Struct Biol, 32, 1-8.
Frey, S. & Görlich, D. (2014) A new set of highly efficient, tag-cleaving proteases for purifying recombinant proteins. J Chromatogr A, 1337, 95-105.

(Continued)

*Primary Examiner* — Galina M. Yakovleva
(74) *Attorney, Agent, or Firm* — Rothwell, Figg, Ernst & Manbeck, P.C.

(57) ABSTRACT

The present invention relates to novel anti-IgG nanobodies, particularly nanobodies directed against rabbit or mouse IgG. Further, the invention relates to the use of said nanobodies and methods for producing them.

11 Claims, 17 Drawing Sheets
Specification includes a Sequence Listing.

(56) References Cited

OTHER PUBLICATIONS

Gottfert, F., Pleiner, T., Heine, J., Westphal, V., Gorlich, D., Sahl, S.J. & Hell, S.W. (2017) Strong signal increase in STED fluorescence microscopy by imaging regions of subdiffraction extent. Proc Natl Acad Sci U S A, 114, 2125-2130.

Gray, A.C., Sidhu, S.S., Chandrasekera, P.C., Hendriksen, C.F. & Borrebaeck, C.A. (2016) Animal-Friendly Affinity Reagents: Replacing the Needless in the Haystack. Trends Biotechnol, 34, 960-969.

Hamers-Casterman, C., Atarhouch, T., Muyldermans, S., Robinson, G., Hamers, C., Songa, E.B., Bendahman, N. & Hamers, R. (1993) Naturally occurring antibodies devoid of light chains. Nature, 363, 446-448.

Helma, J., Cardoso, M.C., Muyldermans, S. & Leonhardt, H. (2015) Nanobodies and recombinant binders in cell biology. J Cell Biol, 209, 633-644.

Huang, B., Babcock, H. & Zhuang, X. (2010) Breaking the diffraction barrier: super-resolution imaging of cells. Cell, 143, 1047-1058.

Huang, F., Sirinakis, G., Allgeyer, E.S., Schroeder, L.K., Duim, W.C., Kromann, E.B., Phan, T., Rivera-Molina, F.E., Myers, J.R., Irnov, I., Lessard, M., Zhang, Y., Handel, M.A., Jacobs-Wagner, C., Lusk, C.P., Rothman, J.E., Toomre, D., Booth, M.J. & Bewersdorf, J. (2016) Ultra-High Resolution 3D Imaging of Whole Cells. Cell, 166, 1028-1040.

Hülsmann, B.B., Labokha, A.A. & Görlich, D. (2012) The permeability of reconstituted nuclear pores provides direct evidence for the selective phase model. Cell, 150, 738-751.

Kijanka, M., Dorresteijn, B., Oliveira, S. & van Bergen en Henegouwen, P.M. (2015) Nanobody-based cancer therapy of solid tumors. Nanomedicine (Lond), 10, 161-174.

Krainer, F.W. & Glieder, A. (2015) An updated view on horseradish peroxidases: recombinant production and biotechnological applications. Appl Microbiol Biotechnol, 99, 1611-1625.

Lam, S.S., Martell, J.D., Kamer, K.J., Deerinck, T.J., Ellisman, M.H., Mootha, V.K. & Ting, A.Y. (2015) Directed evolution of APEX2 for electron microscopy and proximity labeling. Nat Methods, 12, 51-54.

Liu, L., Spurrier, J., Butt, T.R. & Strickler, J.E. (2008) Enhanced protein expression in the baculovirus/insect cell system using engineered SUMO fusions. Protein Expr Purif, 62, 21-28.

Martell, J.D., Deerinck, T.J., Sancak, Y., Poulos, T.L., Mootha, V.K., Sosinsky, G.E., Ellisman, M.H. & Ting, A.Y. (2012) Engineered ascorbate peroxidase as a genetically encoded reporter for electron microscopy. Nat Biotechnol, 30, 1143-1148.

Marx, V. (2013) Calling the next generation of affinity reagents. Nat Methods, 10, 829-833.

McMahon, C., Baier, A.S., Zheng, S., Pascolutti, R., Ong, J.X., Erlandson, S.C., Hilger, D., Ring, A.M., Manglik, A. & Kruse, A.C. (2017) Platform for rapid nanobody discovery in vitro. bioRxiv, doi: https://doi.org/10.1101/151043.

Moutel, S., Bery, N., Bernard, V., Keller, L., Lemesre, E., de Marco, A., Ligat, L., Rain, J.C., Favre, G., Olichon, A. & Perez, F. (2016)

NaLi—H1: A universal synthetic library of humanized nanobodies providing highly functional antibodies and intrabodies. eLife, 5; DOI:10.7554/eLife. 16228.

Muyldermans, S. (2013) Nanobodies: natural single-domain antibodies. Annu Rev Biochem, 82, 775-797.

Pleiner, T. et al., 2015, "Nanobodies: site-specific labeling for super-resolution imaging, rapid epitope-mapping and native protein complex isolation", DOI:10.7554/eLife. 11349.001.

Reardon, S. (2016) US government issues historic $3.5-million fine over animal welfare. Nature, doi:10.1038/nature.2016.19958.

Ries, J., Kaplan, C., Platonova, E., Eghlidi, H. & Ewers, H. (2012) A simple, versatile method for GFP-based super-resolution microscopy via nanobodies. Nat Methods, 9, 582-584.

Rust, M.J., Bates, M. & Zhuang, X. (2006) Sub-diffraction-limit imaging by stochastic optical reconstruction microscopy (STORM). Nat Methods, 3, 793-795.

Sahl, S.J., Hell, S.W. & Jakobs, S. (2017) Fluorescence nanoscopy in cell biology. Nat Rev Mol Cell Biol, vol. 18, 685-701.

Shen, H. (2013) Discovery of goat facility adds to antibody provider's woes. Nature, doi:10.1038/nature.2013.12203.

Szymborska, A., de Marco, A., Daigle, N., Cordes, V.C., Briggs, J.A. & Ellenberg, J. (2013) Nuclear pore scaffold structure analyzed by super-resolution microscopy and particle averaging. Science, 341, 655-658.

Traenkle, B. & Rothbauer, U. (2017) Under the Microscope: Single-Domain Antibodies for Live-Cell Imaging and Super-Resolution Microscopy. Front Immunol, 8, 1030.

Van Bockstaele, F., Holz, J.B. & Revets, H. (2009) The development of nanobodies for therapeutic applications. Curr Opin Investig Drugs, 10, 1212-1224.(Abstract only).

Weber, K., Rathke, P.C. & Osborn, M. (1978) Cytoplasmic microtubular images in glutaraldehyde-fixed tissue culture cells by electron microscopy and by immunofluorescence microscopy. Proc Natl Acad Sci U S A, 75, 1820-1824.

Xu, K., Babcock, H.P. & Zhuang, X. (2012) Dual-objective STORM reveals three-dimensional filament organization in the actin cytoskeleton. Nat Methods, 9, 185-188.

Zimmermann, I., Egloff, P., Hutter, C., Stohler, P., Bocquet, N., Hug, M., Siegrist, M., Svacha, L., Gera, J. & Gmuer, S. (2017) Synthetic single domain antibodies for the conformational trapping of membrane proteins. bioRxiv, doi: https://doi.org/10.1101/168559.

Tu Zhui et al., "Preparation and characterization of novel IgG affinity resin coupling anti-Fc camelid single-domain antibodies", Journal of Chromatography B: Biomedical Sciences & Applications, Elsevier, Amsterdam, NL, vol. 983, Jan. 14, 2015, pp. 26-31.

Els Beghein et al., "Nanobody Technology:A Versatile Toolkit for Microscopic Imaging, Protein-Protein Interaction Analysis, and Protein Function Exploration", Frontiers in Immunology, vol. 8, Jul. 4, 2017.

Tino Pleiner et al., "A toolbox of anti-mouse and anti-rabbit IgG secondary nanobodies", The Journal of Cell Biology : JCB, vol. 217, No. 3, Dec. 20, 2017, pp. 1143-1154.

Inoue et al., "Affinity transfer to a human protein by CDR3 grafting of camelid VHH," Protein Science, 2011, vol. 20, pp. 1971-1981.

* cited by examiner

Figure 1.

A. Overview of Selected Anti-IgG Single-Domain Antibodies

| Nb ID | SEQ ID NO | CDR3 | Subclass Specificity | Epitope | Species specificity |
|---|---|---|---|---|---|
| TP896 | 35 | GKFPVESRRHGGTAQWDEYDY | NA | Fab | Rabbit |
| TP897 | 36 | LVFGGEY | NA | Fc | Rabbit, Gp, Hs (weak) |
| TP1170 | 37 | TYSGNYYSNYTVANYGT | Kappa | - | Mouse |
| TP975 | 38 | GSGPAFRLSGGSWSPRGDGS | Kappa | - | Mouse |
| TP1014 | 39 | RGSSDYDVAMQGHEYTY | Lambda | - | Mouse, rat, rabbit (weak) |
| TP1107 | 40 | GWVRLPDPDLV | IgG1 | Fc | Mouse, rat, Hs (weak) |
| TP878 | 41 | CPGDYTSTICNSDGMDY | IgG1 | Fc | Mouse |
| TP879 | 42 | AQFFNDGHQYCPNPNY | IgG1 | Fc | Mouse, rat |
| TP1104 | 43 | VVLVGREV | IgG1 | Fc | Mouse |
| TP881 | 44 | GAVRLVAGALARPAD | IgG1 | Fc | Mouse, rat (weak) |
| TP882 | 45 | YRRSGAYCTSGGQDY | IgG1 | Fc | Mouse, rat |
| TP883 | 46 | AVTYASCNEYDY | IgG1 | Fc | Mouse, rat, Hs (weak) |
| TP884 | 47 | GGSDTATSRAI | IgG1 | Fc | Mouse, rat (weak) |
| TP894 | 48 | FEQKNIYCSGYSLTLSARGVMDH | IgG1 | Fc | Mouse |
| TP895 | 49 | VARGTWGRGGVDRTTDQAMCIPRDPSVDF | IgG1 | Fc | Mouse |
| TP885 | 50 | VPGYSDYRQGYDY | IgG1 | Hinge(?) | Mouse, rat |
| TP886 | 51 | EVTYYSGTYYLFGTKQEYDY | IgG1 | Fab (κ+λ) | Mouse |
| TP887 | 52 | QMKFQITTMDSDYDY | IgG1/2a | Fab (κ) | Mouse |
| TP888 | 53 | IFHREITTVPRKYDY | IgG1/2a | Fab (κ) | Mouse |
| TP889 | 54 | STMRSIDFYVTDFGS | IgG1/2a | Fab (κ) | Mouse |
| TP890 | 55 | TFKWEVTTTPDGYDY | IgG1/2a | Fab (κ) | Mouse |
| TP1106 | 56 | AVVRQWPNAHQGAYDY | IgG1/2a/2b | Fab (κ) | Mouse |
| TP1129 | 57 | NKGPHYHSDYFDSNLYDF | IgG2a | Fc | Mouse |
| TP922 | 58 | EGWEDTITEEPNDENY | IgG2a | Fc | Mouse |
| TP923 | 59 | EEGGT | IgG2a | Fc | Mouse |
| TP926 | 60 | CARCFFVPRMTSAAAYGY | IgG2a | Hinge(?) | Mouse |
| TP925 | 61 | VRLSRGYLCRNYDMDY | IgG1/2a/2b | Fc | Mouse |
| TP979 | 62 | GVGDGSSCPDSAYEYAY | IgG2b | Fab (κ) | Mouse, Gp |
| TP984 | 63 | LQSWGSYPHDDY | IgG2b | Fab (κ) | Mouse |
| TP924 | 64 | GGAATVVGGPYDY | IgG3 | Fc | Mouse, rabbit |
| TP929 | 65 | LERATMCPRRDPTWYDY | IgG2a/3 | Fc | Mouse, rabbit (weak) |

B. All specificity classes of anti-mouse IgG single domain antibodies

Figure 1 – figure supplement 1.
a  Crossreactivity to polyclonal IgG of other species
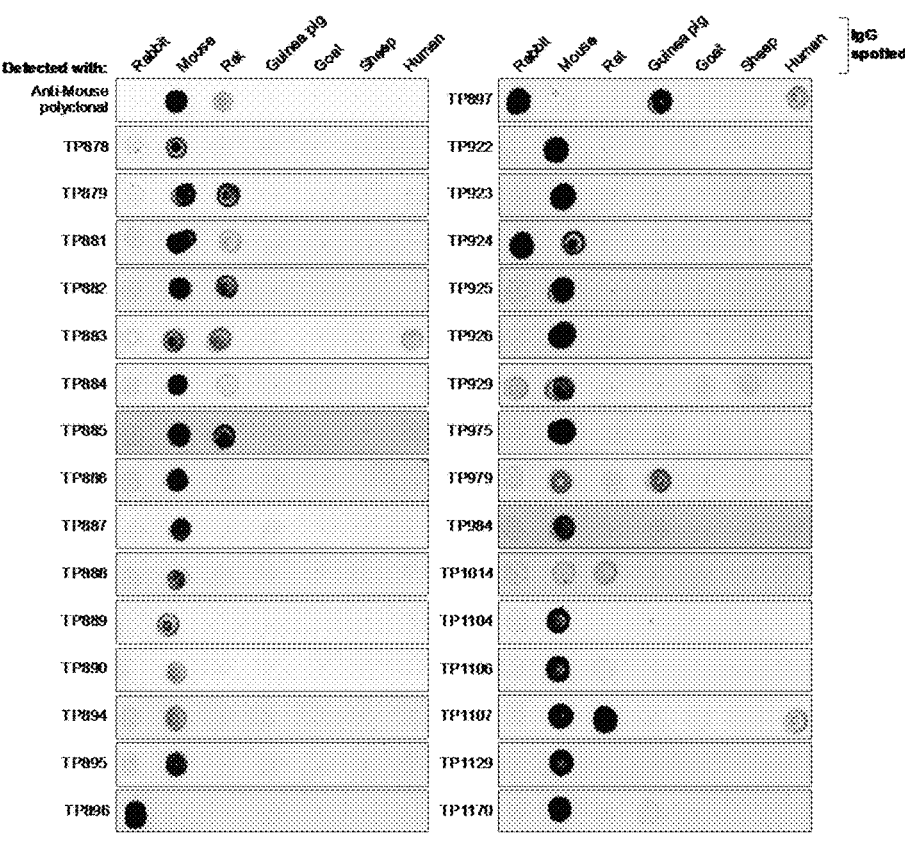
b  Isolation of rabbit IgG from rabbit serum
c  Isolation of mouse mAb from hybridoma supernatant
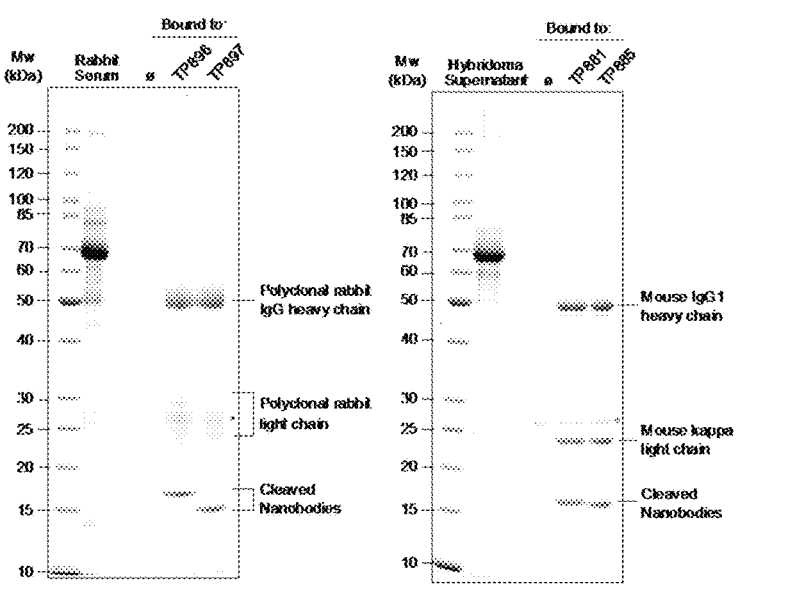

Figure 2 – figure supplement 1.
a HRP conjugation to anti-IgG1 Fc Nb TP1107
b Expression of anti-IgG1 Fc Nb TP1107 fusion to ascorbate peroxidase APEX2
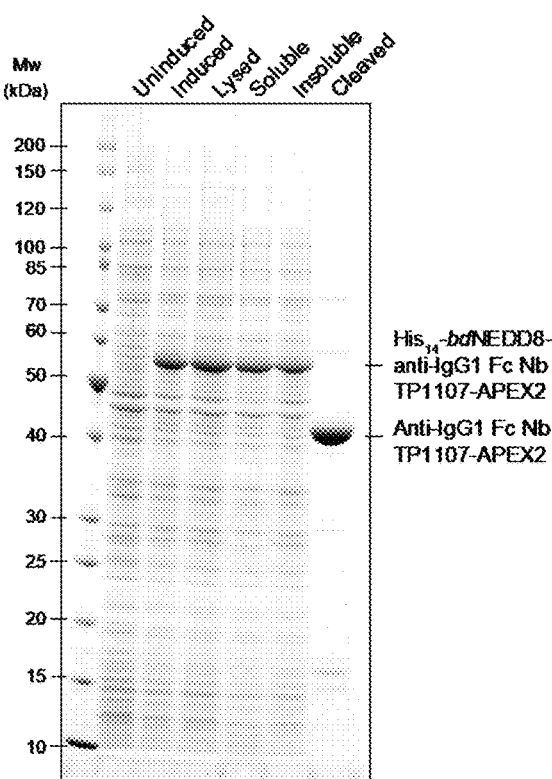

a    Immunofluorescence with anti-mouse IgG1 antibodies b   Immunofluorescence with anti-mouse IgG2a antibodies c Immunofluorescence with anti-rabbit IgG antibodies d   Multicolor-staining of HeLa cells

Figure 4 – figure supplement 1.
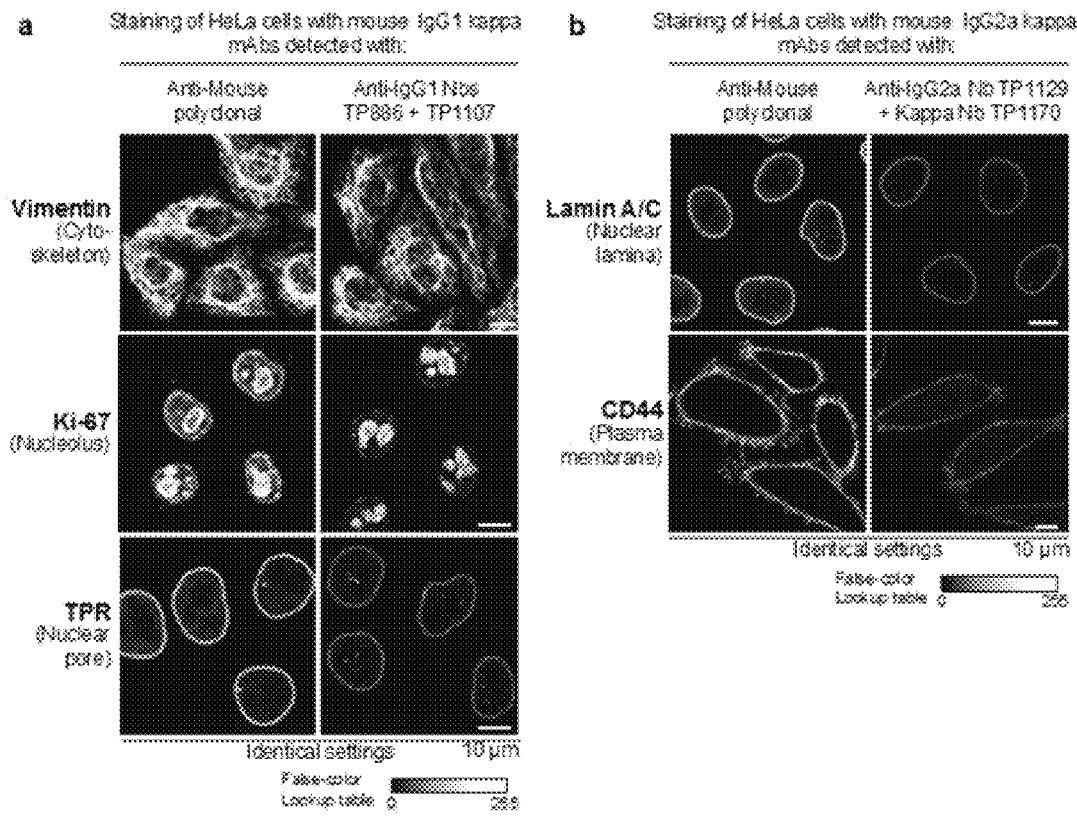

Figure 4 – figure supplement 1.
c          Affinity maturation of anti-IgG2a Fc antibody TP921
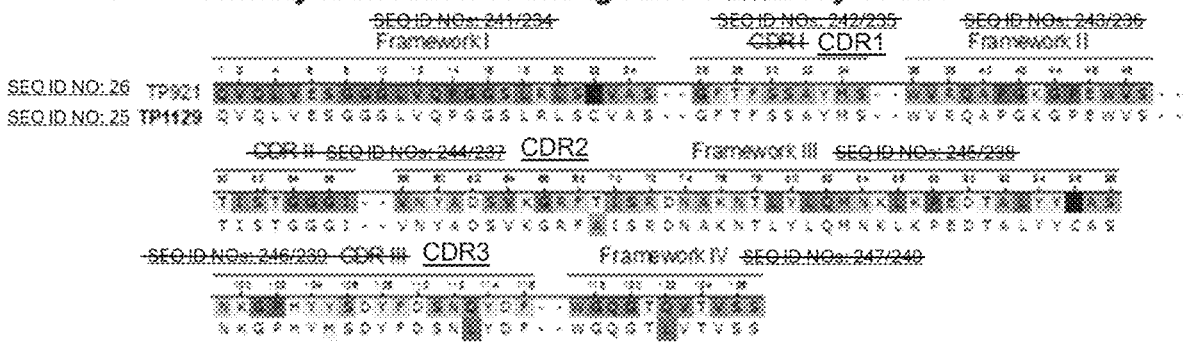
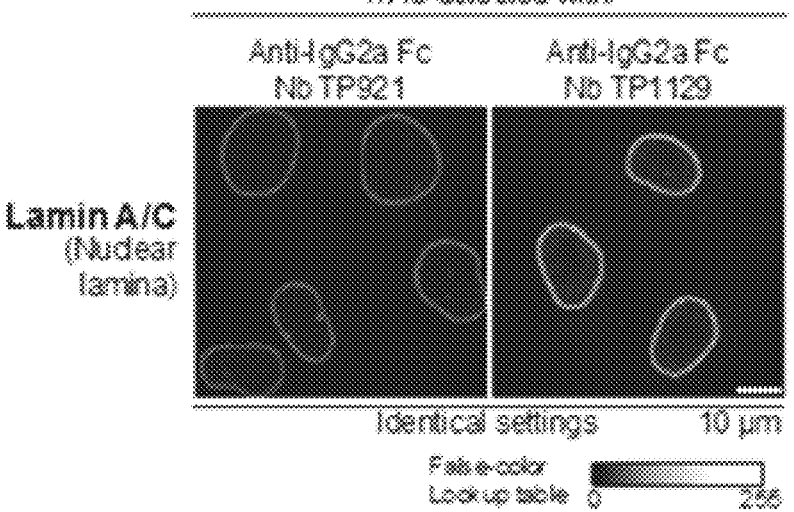

Figure 4 – figure supplement 1.
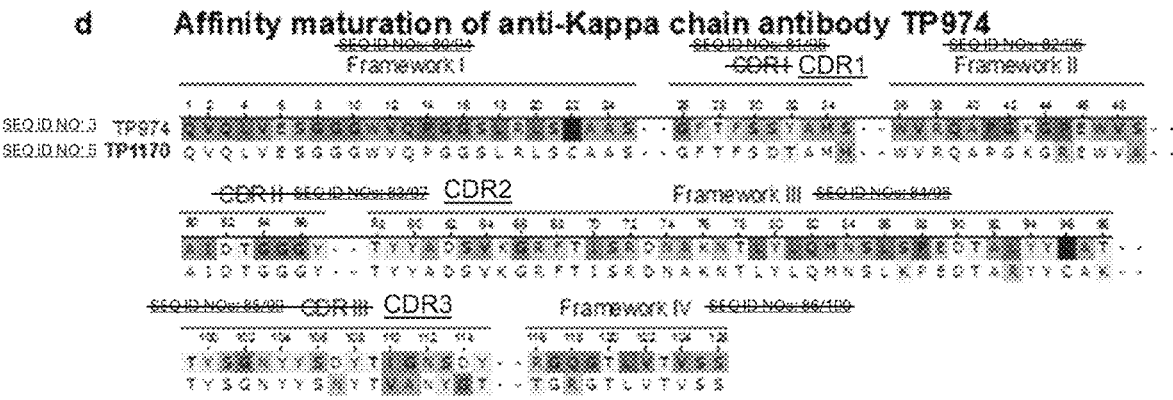
d   Affinity maturation of anti-Kappa chain antibody TP974
Staining of HeLa cells with mouse IgG2a kappa
mAb detected with:
Anti-Kappa chain
Nb TP974
Anti-Kappa chain
Nb TP1170
Lamin A/C
(Nuclear
lamina)
Identical settings          10 μm
False color
Lookup table

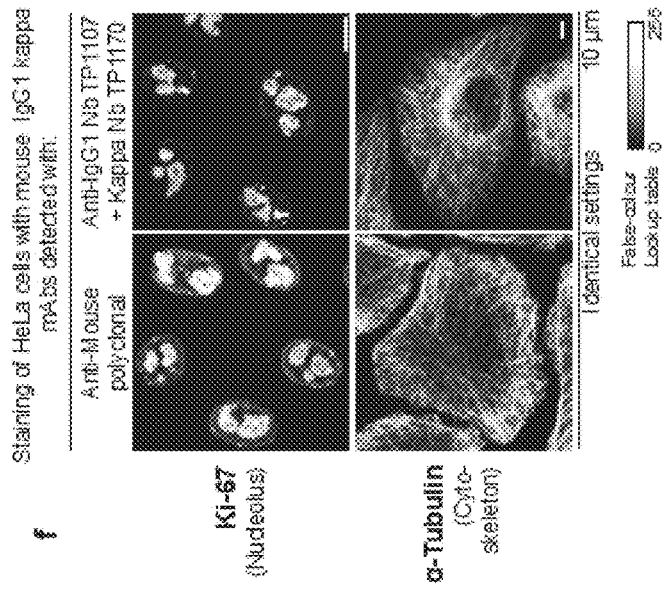
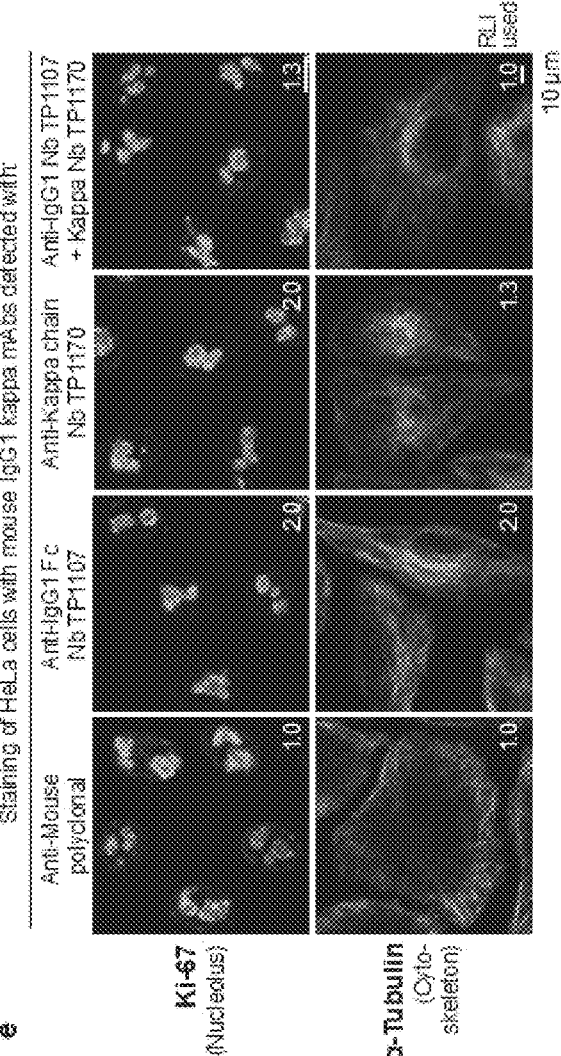
Figure 4 – figure supplement 1.

a  One-step immunostaining of HeLa cells b   One-step multicolor-staining of HeLa cells with IgG1 mABs

ANTI-IgG NANOBODIES

CROSS REFERENCE TO RELATED APPLICATION

This application is a 35 U.S.C. 371 National Phase Entry Application from PCT/EP2018/077751, filed Oct. 11, 2018, which claims the benefit of European Patent Application No. 17195992.7 filed on Oct. 11, 2017, the disclosure of which is incorporated herein in its entirety by reference.

SEQUENCE LISTING

The instant application contains a Sequence Listing which has been submitted via EFS-Web and is hereby incorporated by reference in its entirety. The Sequence Listing, created on May 29, 2025, is named "2923-1357_20250110_ST25.txt" and is 101,946 bytes in size.

DESCRIPTION

The present invention relates to novel anti-IgG single-domain antibodies, particularly single-domain antibodies directed against rabbit or mouse IgG. Further, the invention relates to the use of said single-domain antibodies and methods for producing them.

Mouse and rabbit antibodies are fundamental tools for numerous basic research techniques as well as medical diagnostic assays. The detection or immobilization of these primary antibodies is most often performed indirectly via polyclonal anti-IgG secondary antibodies. Yet, the need for a continuous supply of anti-IgG sera requires keeping, immunizing, bleeding and eventually sacrificing large numbers of goats, sheep, rabbits, or donkeys, which is not only costly but also a major animal welfare and ethical problem (Shen, 2013; Reardon, 2016). Furthermore, every new batch of serum contains another heterogeneous mixture of antibodies, which need to be affinity-purified on IgG columns and then depleted (by pre-adsorption) of nonspecific and crossreacting antibodies. Moreover, the success of this procedure has to be laboriously quality controlled each time. The large size of secondary antibodies (~10-15 nm; 150 kDa) is also a disadvantage, since it limits tissue penetration and introduces a considerable label displacement, reducing the obtainable image resolution by super-resolution fluorescence microscopy methods (Ries et al., 2012; Szymborska et al., 2013; Pleiner et al., 2015). Their non-recombinant nature further precludes genetic engineering i.e. tagging or fusion to reporter enzymes.

Why then, have recombinant anti-IgG detection reagents not yet replaced polyclonal secondary antibodies? The major issue is regarding signal strength. The signal in traditional immunofluorescence, for example, is amplified by: (i) multiple secondary IgG molecules binding to distinct epitopes of a primary antibody; (ii) a large IgG tolerating many labels per molecule; and (iii) by their bivalent binding mode exploiting avidity for high affinity target recognition. In the light of these facts, it appears very challenging to achieve comparable signal levels with a small, monovalent and monoclonal reagent.

Yet, we considered single-domain antibodies derived from camelid heavy-chain antibodies (Hamers-Casterman et al., 1993; Arbabi Ghahroudi et al., 1997; Muyldermans, 2013), as perhaps the best candidates for such reagents. Due to their small size (~3×4 nm; 13 kDa), the possibility of their renewable production as recombinant fusion proteins, as well as favorable biophysical properties, single-domain antibodies attracted considerable attention as powerful tools in cell biology (Helma et al., 2015), structural biology (Desmyter et al., 2015) and as future therapeutic agents (Van Bockstaele et al., 2009; Kijanka et al., 2015). They are particularly useful for super-resolution imaging (Ries et al., 2012; Szymborska et al., 2013; Pleiner et al., 2015; Göttfert et al., 2017; Traenkle and Rothbauer, 2017). The resolving power of some of the best microscopes reported to date (e.g. ~6 nm by Balzarotti et al., 2017; ~ 10-20 nm by Huang et al., 2016 or Xu et al., 2012) may be reduced due to the offset between fluorescent label and target introduced by primary and secondary antibodies (20-30 nm). Site-specifically labeled single-domain antibodies represent a promising solution to this problem, since they can place fluorophores closer than 2 nm to their antigen and, despite their small size, even tolerate up to three dyes (Pleiner et al., 2015).

In this study, we describe the generation of a comprehensive toolbox of Nanobodies® (Ig single variable domains) against all mouse IgG subclasses and rabbit IgG. This work required very extensive optimizations of our routine Nanobody® (single domain antibody) selection efforts, such as a time-stretched and thus affinity-enhancing immunization scheme, subsequent affinity maturation including off-rate selections, as well as testing and improving "200 initial candidates. When labeled site-specifically with fluorophores, the resulting Nanobodies® (single domain antibodies) performed remarkably well in Western Blotting and immunofluorescence. In contrast to polyclonal secondary antibodies, they even allow a single-step multicolor labeling and co-localization. Moreover, we show that anti-IgG Nanobodies® can be conjugated to horseradish peroxidase (HRP) or expressed as fusions to ascorbate peroxidase (APEX2) (Lam et al., 2015) and thus used for enhanced chemiluminescence Western blotting or colorimetric ELISAs or immuno-EM detection. These monoclonal recombinant Nanobodies® are thus perfect substitutes for conventional animal-derived polyclonal secondary antibodies. We envision that they can be engineered to enable a more versatile use of the plethora of existing antibodies and even allow the development of more sophisticated antibody-based diagnostic tests.

A first aspect of the invention relates to a single-domain antibody directed against rabbit IgG comprising
    (a) a CDR3 sequence as shown in SEQ ID NO. 1 or 2, or
    (b) a CDR3 sequence which has an identity of at least 80%, particularly at least 90% to a CDR3 sequence as shown in SEQ ID NO. 1 or 2.

In a particular embodiment, the single-domain antibody comprises
    (a) a combination of CDR1, CDR2 and CDR3 sequences as shown in SEQ ID NO. 1 or 2, or
    (b) a combination of CDR1, CDR2 and CDR3 sequences which has an identity of at least 80%, particularly at least 90% to a combination of CDR1, CDR2 and CDR3 sequences as shown in SEQ ID NO. 1 or 2.

In a further particular embodiment, the single-domain antibody comprises a sequence as shown in SEQ ID NO. 1 or 2, or a sequence which has an identity of at least 70%, particularly at least 80% and more particularly at least 90% to a sequence as shown in SEQ ID NO. 1 or 2.

A further aspect of the invention relates to a single-domain antibody directed against mouse IgG comprising
    (a) a CDR3 sequence as shown in any one of SEQ ID NO. 3-34, or
    (b) a CDR3 sequence which has an identity of at least 80%, particularly at least 90% to a CDR3 sequence as shown in any one of SEQ ID NO. 3-34.

In a particular embodiment, the single-domain antibody comprises (a) a combination of CDR1, CDR2 and CDR3 sequences as shown in any one of SEQ ID NO. 3-34, or (b) a combination of CDR1, CDR2 and CDR3 sequences which has an identity of at least 80%, particularly at least 90% to a combination of CDR1, CDR2 and CDR3 sequences as shown in any one of SEQ ID NO. 3-34.

In a further particular embodiment, the single-domain antibody comprises a sequence as shown in any one of SEQ ID NO. 3-34 or a sequence which has an identity of at least 70%, particularly at least 80% and more particularly at least 90% to a sequence as shown in any one of SEQ ID NO. 3-34.

Still a further aspect of the present invention is a reagent for detecting, isolating and/or purifying IgG, particularly rabbit or mouse IgG comprising at least one single-domain antibody as described above.

Still a further aspect of the invention is a method for detecting, isolating and/or purifying IgG, particularly rabbit and/or mouse IgG, comprising binding of at least one single-domain antibody as described above to IgG.

In a preferred embodiment, the single-domain antibody is specifically directed to one of the following groups of types of IgG molecules and epitopes:

rabbit IgG Fab fragment rabbit IgG Fc fragment mouse IgG kappa light chain or mouse IgG lambda light chain mouse IgG1, e.g. IgG1 Fc fragment, IgG1 hinge region, or IgG1 Fab fragment mouse IgG1/IgG2a, e.g. IgG1/IgG2a Fab fragment mouse IgG1/IgG2a/IgG2b, e.g. IgG1/IgG2a/IgG2b Fab fragment mouse IgG2a, e.g. IgG2a Fc fragment or IgG2a hinge region mouse IgG2a/2b, e.g. IgG2a/IgG2b Fc fragment mouse IgG2b, e.g. IgG2b Fab fragment mouse IgG3, e.g. IgG3 Fc fragment mouse IgG2a/3, e.g. IgG3 Fc fragment Specific embodiments of preferred anti-IgG single-domain antibodies are shown in Tables 1 and 2. Table 1 indicates isotype, epitope and species specificity of particular single-domain antibodies of the present invention.

TABLE 1

| SEQ ID | Nb ID | Isotype specificity | Epitope | Species specificity |
|---|---|---|---|---|
| 1 | TP896 | N/A | Fab | Rabbit only |
| 2 | TP897 | N/A | Fc | Rabbit, Guinea pig, Human (weak) |
| 3 | TP974 | Kappa chain | — | Mouse, Guinea pig (weak) |
| 4 | TP1079 | Kappa chain | — | Mouse, Guinea pig (weak) |
| 5 | TP1170 | Kappa chain | — | Mouse, Guinea pig (weak) |
| 6 | TP975 | Kappa chain | — | Mouse only |
| 7 | TP1014 | Lambda chain | — | Mouse, Rat, Rabbit (weak) |
| 8 | TP1107 | IgG1 | Fc | Mouse, Rat, Human (weak) |
| 9 | TP878 | IgG1 | Fc | Mouse only |
| 10 | TP879 | IgG1 | Fc | Mouse, Rat |
| 11 | TP1104 | IgG1 | Fc | Mouse only |
| 12 | TP881 | IgG1 | Fc | Mouse, Rat (weak) |
| 13 | TP882 | IgG1 | Fc | Mouse, Rat |
| 14 | TP883 | IgG1 | Fc | Mouse, Rat, Human (weak) |
| 15 | TP884 | IgG1 | Fc | Mouse, Rat (weak) |
| 16 | TP894 | IgG1 | Fc | Mouse only |
| 17 | TP895 | IgG1 | Fc | Mouse only |
| 18 | TP885 | IgG1 | Hinge (?) | Mouse, Rat |
| 19 | TP886 | IgG1 | Fab ($\kappa + \lambda$) | Mouse only |
| 20 | TP887 | IgG1/IgG2a | Fab ($\kappa$ only) | Mouse only |
| 21 | TP888 | IgG1/IgG2a | Fab ($\kappa$ only) | Mouse only |
| 22 | TP889 | IgG1/IgG2a | Fab ($\kappa$ only) | Mouse only |
| 23 | TP890 | IgG1/IgG2a | Fab ($\kappa$ only) | Mouse only |
| 24 | TP1106 | IgG1/IgG2a/IgG2b | Fab ($\kappa$ only) | Mouse only |
| 25 | TP1129 | IgG2a | Fc | Mouse only |
| 26 | TP921 | IgG2a | Fc | Mouse only |
| 27 | TP922 | IgG2a | Fc | Mouse only |
| 28 | TP923 | IgG2a | Fc | Mouse only |
| 29 | TP926 | IgG2a | Hinge (?) | Mouse only |
| 30 | TP925 | IgG2a/2b | Fc | Mouse only |
| 31 | TP979 | IgG2b | Fab ($\kappa$ only) | Mouse, Guinea pig |
| 32 | TP984 | IgG2b | Fab ($\kappa$ only) | Mouse only |
| 33 | TP924 | IgG3 | Fc | Mouse, Rabbit |
| 34 | TP929 | IgG2a/3 | Fc | Mouse, Rabbit (weak) |

N/A = not applicable; Fab = Fragment antigen-binding; Fc = Fragment crystallisable; $\kappa$ = kappa light chain; $\lambda$ = lambda light chain.

Table 2 indicates the amino acid sequences as well as the individual framework portions, i.e. framework 1, 2, 3 and 4, and CDR sequences, i.e. CDR1, CDR2 and CDR3 sequences of particular single-domain antibodies of the present invention, i.e., SEQ ID NO:35 to SEQ ID NO:271.

TABLE 2

| SEQ ID | FW I SEQ ID | FW I | CDR1 SEQ ID | CDR1 | FW II SEQ ID | FW II | CDR2 SEQ ID | CDR2 |
|---|---|---|---|---|---|---|---|---|
| 1 | 66 | QVQLVESGGGLAQPGGSLRLSCAVS | 67 | GFRFSFYQMT | 68 | WVRQAPGKGLEWVA | 69 | DINSAGGT |
| 2 | 72 | QVQLVESGGGLVQAGDSLRLSCVAS | 73 | GRSLDGATMR | 74 | WYRQAPGKEREFVA | 75 | GIFWDEIG |
| 3 | 78 | QVQLVESGGGWVQPGGSLRLSCAAS | 79 | GFTFSSYAMS | 80 | WVRQAPGKGPEWVS | 81 | AIDTGGGY |
| 4 | 85 | QVQLVESGGGLVLPGGSLRLSCVAS | 86 | GFTFSDTAMM | 87 | WVRQAPGKGREWVA | 88 | AIDTGGSS |
| 5 | 91 | QVQLVESGGGWVQPGGSLRLSCAAS | 92 | GFTFSDTAMM | 93 | WVRQAPGKGREWVA | 94 | AIDTGGGY |
| 6 | 97 | QVQLVESGGGLVQPGGSLRLSCAAS | 98 | GFTFSNYDMS | 99 | WVRQAPGKGLEWVS | 100 | AISSGGGS |
| 7 | 103 | QVQLVESGGGEVQAGGSLRLSCAAS | 104 | GRTFSRNVMG | 105 | WFRQAPGKEREFLA | 106 | AINWSGNS |
| 8 | 109 | QVQLVESGGGLVQPGGSLRLSCAAS | 110 | GFTFSDTWMN | 111 | WVRQAPGKGLYWIS | 112 | AINPDGGN |
| 9 | 115 | QVQLVESGGGLVQAGGSLRLSCAAS | 116 | GSIFSINAMA | 117 | WYRHRPGMQRERVA | 118 | AISSGGT |
| 10 | 121 | QVQLVESGGGLVQPGGSLRLSCVVS | 122 | GGTMNAYAIG | 123 | WFRQAPGKEREAVS | 124 | CITSNSKY |
| 11 | 127 | QVQLVESGGGLVQPGGSLRLSCTAS | 128 | GFTFSDSPMT | 129 | WARQAPGKRLEWVS | 130 | TISSDGEK |
| 12 | 133 | QVQLVESGGGLVQPGGSLRLSCAAF | 134 | GFTFSNYYMN | 135 | WVRQAPGKGLEWIS | 136 | GINSGGGT |
| 13 | 139 | QVQLVESGGGLVQPGGSLTLSCATS | 140 | GFSLDYYSIG | 141 | WFRQAPGKEREGVS | 142 | CISSTGGS |
| 14 | 145 | QVQLVESGGGLVQPGGSLRLSCAAS | 146 | GFTLDYYAIG | 147 | WFRQAPGKEREGVA | 148 | CITSSEGS |
| 15 | 151 | QVQLVESGGGLVQPGGSLTLSCVIS | 152 | GFRMDIATMS | 153 | WVRQAPGKGLEWVA | 154 | GIINYRNF |
| 16 | 157 | QVQLVESGGGLVQPGGSLRLSCAVS | 158 | GLTLDFKGIG | 159 | WFRQAPGKEREGVS | 160 | CINPSDSS |
| 17 | 163 | QVQLVESGGGLVQPGGSLRLSCAAS | 164 | GFTLDYYAIG | 165 | WFRQAPGKEHEGVS | 166 | CISPSGGS |
| 18 | 169 | QVQLVESGGGLVQAGGSVRLSCAAS | 170 | GFTFSSYYMT | 171 | WVRQAPGKGPEWVS | 172 | AINTGGDA |
| 19 | 175 | QVQLVESGGGLVQPGGSLRLSCAAS | 176 | GFTFANYYMS | 177 | WVRQAPGKGPEWVS | 178 | AINTLGGK |
| 20 | 181 | QVQLVESGGGLVQAGGSLRLSCAAS | 182 | GRTFSTYIMG | 183 | WVRQAPGKGPEWVS | 184 | AITWIGGS |
| 21 | 187 | QVQLVESGGGLVQDGGSLRLSCAAS | 188 | GRTFSVYAMG | 189 | WFRQAPGKEREFVA | 190 | AISWIGGS |
| 22 | 193 | QVQLVESGGGLVQAGDSLRLSCTAS | 194 | GRTFSTYAMG | 195 | WFRQAPGKEREFVA | 196 | AISWIGGS |
| 23 | 199 | QVQLVESGGEAVQTGGSLRLSCAAS | 200 | GRTFSTYLMG | 201 | WFRQAPGKEREFVA | 202 | AISWIGGS |
| 24 | 205 | QVQLVESGGGLVQPGGSLRLYCAAS | 206 | GRTDTTYALG | 207 | WFRQPPGKERQFVA | 208 | SITWIGGA |
| 25 | 211 | QVQLVESGGGLVQPGGSLRLSCVAS | 212 | GFTFSSAYMS | 213 | WVRQAPGKGPEWVS | 214 | TISTGGGI |
| 26 | 217 | QVQLVESGGGLVQPGGSLRLSCVAS | 218 | GFTFSSAYMS | 219 | WVRQAPGKGPEWVS | 220 | TISTGGGI |
| 27 | 224 | QVQLVESGGGLVQPGGSLRLSCAAS | 225 | GFTFSSYYMS | 226 | WVRQAPGKGLEWVS | 227 | DISTDGGR |
| 28 | 230 | QVQLVESGGGLVQPGESLTLSCAAS | 231 | GFTFSNVAMS | 232 | WVRQAPRKGLEWVS | 233 | SISSDGGR |
| 29 | 236 | QVQLVESGGGLVQAGGSLRLSCAAS | 237 | ETIFSINVMG | 238 | WFRQAPGKERELVA | 239 | KISSVGS |
| 30 | 242 | QVQLVESGGGLVQPGGSLRLSCAAS | 243 | ETIFSINVMG | 244 | WFRQAPGKERELVA | 244 | SISSDGGR |
| 31 | 248 | QVQLVESGGGLVQPGGSLRLSCAAS | 249 | GFTLDYYAIG | 250 | WFRLAPGKEREGVS | 251 | CISSSGGS |
| 32 | 254 | QVQLVESGGGLVQGGGSLRLSCAAS | 255 | RSIFSINAMG | 256 | WYRQALGKERELVA | 257 | AISSGGS |
| 33 | 260 | QVQLVESGGGLVQPGGSLRLSCAAS | 261 | GFTFSSYAMT | 262 | WVRQAPGKGLEWVG | 263 | DINGVGNY |
| 34 | 266 | QVQLVESGGGLVQPGGSLRLSCAAS | 267 | GFTLDYYAIG | 268 | WFRQAPGKEREGVS | 269 | CISSSSGR |

TABLE 2-continued

| SEQ ID | FW III SEQ ID | FW III | CDR3 SEQ ID | CDR3 | FW IV SEQ ID | FW IV |
|---|---|---|---|---|---|---|
| 1 | 70 | TYYADSVKGRFAISRDNAKNTLYLQMNSLKPEDTAVYYCAK | 35 | GKFPVESRRHGGTAQWDEYDY | 71 | WGQGTRVTVSS |
| 2 | 76 | TEYADTAKGRFTISRDNAKNTIYLQMTNLRSEDTAMYYCNG | 36 | LVFGGEY | 77 | WGQGTQVTVSS |
| 3 | 82 | TYYADSVKGRFTISRDNAKNTLYLQMNSLSPEDTALYYCAT | 83 | TYSGNYYSDYTIGNSDY | 84 | RGQGTLVTVSS |
| 4 | 89 | TYYADSVQGRFTISRDSAKNTLYLQMNSLKPEDTARYYCAK | 37 | TYSGNYYSNYTVANYGT | 90 | TGRGTLVTVSS |
| 5 | 95 | TYYADSVKGRFTISRDNAKNTLYLQMNSLKPEDTARYYCAK | 37 | TYSGNYYSNYTVANYGT | 96 | TGRGTLVTVSS |
| 6 | 101 | TYYVDSVKGRFTISRDNAKNTVYLQMNSLKPEDTAVYYCAT | 38 | GSGPAFRLSGGSWSPRGDGS | 102 | RGQGTLVTVSS |
| 7 | 107 | IGYRDSVKGRFTASRDNVNNTLYLRMNNLKPEDTAVYYCAA | 39 | RGSSDYDVAMQGHEYTY | 108 | WGQGTQVTVSS |
| 8 | 113 | TAYADSVKGRFTISRDNAKNMVYLQMDNLRPEDTAMYYCAK | 40 | GWVRLPDPDLV | 114 | RGQGTQVTVSS |
| 9 | 119 | TSYADSVKGRFTISRDNARDTLYLQMNSLKPEDTAMYYCAA | 41 | CPGDYTSTICNSDGMDY | 120 | WGKGTLVTVSS |
| 10 | 125 | TNYADSVKGRFTISRDNAKSTAYLQMNSLEPEDTAVYYCAA | 42 | AQFFNDGHQYCPNPNY | 126 | WGQGTQVTVSS |
| 11 | 131 | IGYRDAVKGRFTISRDNAKNTLYLQMNSLKPEDTAVYYCLN | 43 | VVLVGREV | 132 | FSNGTLVTVSS |
| 12 | 137 | TAYADSVKGRFTISRDNAKNTLYLQMNSLKPEDTAVYYCAK | 44 | GAVRLVAGALRPAD | 138 | WGQGTQVTVSS |
| 13 | 143 | TNYVDSVKGRFTISRDNAKNTVYLQMNSLKPEDTGVYYCAA | 45 | YRRSGAYCTSGGQDY | 144 | WGKGTLVTVSS |
| 14 | 149 | TYYADSVKGRFTISRDNAKNTVYLQMNSLKPEDTAVYYCAA | 46 | AVTYASCNEYDY | 150 | SGQGTQVTVSS |
| 15 | 155 | TWYSDSVKGRFTISTDTAKSEVYLQMNSLKSEDTAVYYCAH | 47 | GGSDTATSRAI | 156 | RGQGTQVTVSS |
| 16 | 161 | AAYADSVKGRFTISRDNAKNTVYLQMNNLQPEDTAVYYCVA | 48 | FEQKNIYCSGYSLTLSARGVMDH | 162 | WGKGTLVTVSS |
| 17 | 167 | TNYADSVKGRFTISRDNAKNTVYLQMNSLKPEDTAVYSCVA | 49 | VARGTWGRGGVDRTTDQAMCIPR DPSVDF | 168 | WGKGTQVTVSS |
| 18 | 173 | TRYAESVKGRFTISRDNAKNMLYLQMNSLKPEDTALYYCGR | 50 | VPGYSDYRQGYDY | 174 | RGQGTLVTVSS |
| 19 | 179 | TKYADSVKGRFTISRDNAKSTLYLQMNSLKPEDTALYYCAR | 51 | EVTYYSGTYXLFGTKQEYDY | 180 | RGQGTQVTVSS |
| 20 | 185 | TYYADSVKGRFTISRDYAKNTLYLQMNSLKPEDTAVYYCAA | 52 | QMKFQITTMDSDYDY | 186 | WGQGTQVTVSS |
| 21 | 191 | TYSADSVKGRFTISREYAKNTLYLQMNSLRPEDTAVYYCAA | 53 | IFHREITTVPRKYDY | 192 | WGQGTQVTVSS |
| 22 | 197 | TYYADSVKGRFTISRDYAENTLYLQMNSLKPEDTAVYYCAA | 54 | STMRSIDFYVTDFGS | 198 | WGQGTLVTVSS |
| 23 | 203 | TYYADSVKGRFTISRDYAENTLYLQMNSLKPEDTAVYYCAA | 55 | TFKWEVTTTPDGYDY | 204 | WGQGTQVTVSS |
| 24 | 209 | TNYAASVKGRFTISKDLGTNTFNLQMNSLTPDDTAVYYCAA | 56 | AVVRQWPNAHQGAYDY | 210 | WGQGTQVTVSS |
| 25 | 215 | VNYADSVKGRFAISRDNAKNTLYLQMNKLKPEDTALYYCAS | 57 | NKGPHYHSDYFDSNLYDF | 216 | WGQGTLVTVSS |
| 26 | 221 | VNYADSVKGRFTISRDNAKNTLYLQMNKLKPEDTALYYCAS | 222 | NKGPHYYSDYFDSNQYDF | 223 | WGQGTQVTVSS |
| 27 | 228 | TLYADSVKGRFTISRDNAKNTLYLQMNSLKPEDTALYFCAR | 58 | EGWEDTITEEPNDENY | 229 | WGKGTLVTVSS |
| 28 | 234 | TLYAASVKGRFTVSRDNAKNTLTLQMDSLKAEDTAVYYCTE | 59 | EEGGT | 235 | RGQGTQVTVSS |
| 29 | 240 | TYYADPVKGRFTISRDDTKNTLSLQMNSLKPEDTAMYYCAA | 60 | CARCFFVPRMTSAAAYGY | 241 | WGQGTQVTVSS |
| 30 | 246 | TTYGDSVQGRFTSSRDNAKNTAYLQMNHLKPEDTAVYYCAA | 61 | VRLSRGYLCRNYDMDY | 247 | WGKGTQVTVSS |
| 31 | 252 | TNYADSVKGRFTISRNNAKNTVYLQMNSLKPEDTAVYYCAL | 62 | GVGDGSSCPDSAYEYAY | 253 | WGQGTQVTVSS |
| 32 | 258 | TYYVDSVKGRFTISRDHVKNTLYLQMNSLKPEDTAMYYCAA | 63 | LQSWGSYPHDDY | 259 | WGQGTQVTVSS |
| 33 | 264 | TYYADSVKGRFTISRDNAKNTLYLQMNNLKPEDTAVYYCAP | 64 | GGAATVVGGPYDY | 265 | WGQGTQVTVSS |
| 34 | 270 | TDYVDSVKGRFTISRDNARNTVYLQMNSLKPEDTAVYYCAA | 65 | LERATMCPRDPTWYDY | 271 | WGQGTQVTVSS |

In its broadest sense, the single-domain antibody of the invention is defined by the presence of at least one CDR3 loop which, as such, is capable of mediating efficient binding to the target molecule. In many cases, CDR1 and/or CDR2 sequences may be varied e.g. by loop grafting, without detrimentally affecting the target specificity. The CDR3 sequence of a single-domain antibody of the invention is defined as a sequence having an identity on the amino acid level of at least 80%, particularly of at least 90% and more particularly of at least 95% with a CDR3 sequence shown in any one of SEQ ID NOs 1-34. In a special embodiment, the CDR3 sequence of the single-domain antibody is as defined in any one of SEQ ID NOs 1-34.

In a more specific embodiment, the single-domain antibody of the present invention is defined by a combination of CDR1, CDR2 and CDR3 sequences as shown in any one of SEQ ID NOs 1-34 or a combination of CDR1, CDR2 and CDR3 sequences having a sequence identity on the amino acid level of at least 80%, of at least 90% or at least 95% to a combination of CDR1, CDR2 and CDR3 sequences as shown in any one of SEQ ID NOs 1-34.

In an even more specific embodiment, the single-domain antibodies of the invention have an amino acid sequence as shown in any one of SEQ ID NOs 1-34 or an amino acid sequence having an identity of at least 70%, at least 75%, at least 80%, at least 85%, at least 90% or at least 95% on the amino acid level to an amino acid sequence as shown in any one of SEQ ID NO. 34. In particular, the single-domain antibodies of the invention have an amino acid sequence as shown in any one of SEQ ID NOS 1-34.

The single-domain antibodies of the present invention are characterized by a high binding specificity to different IgG subclasses, in particular to the four mouse IgG subclasses, e.g. to the mouse IgG1 subclass, mouse IgG2a subclass, mouse IgG2b subclass and/or mouse IgG3 subclass, or to the rabbit IgG subclass. For example, single-domain antibodies of the present invention recognizing mouse IgG1 subclass molecules may be selected from single-domain antibodies of SEQ ID NOs: 8-24. In particular, anti-mouse single-domain antibodies specifically targeting mouse IgG1 molecules may be selected from single-domain antibodies of SEQ ID NOs: 8-19. Further, single-domain antibodies of the present invention recognizing mouse IgG2a isotype molecules may be selected from the single-domain antibodies of SEQ ID NOs: 20-30 and 34. In particular, anti-mouse single-domain antibodies specifically targeting IgG2a molecules may be selected from single-domain antibodies of SEQ ID NOs: 25-29. Nanobodies® of the present invention which recognize mouse IgG2b subclass molecules are selected from single-domain antibodies of SEQ ID NOs: 24 and 30-32, whereby single-domain antibodies of SEQ ID NOs: 31 and 32 specifically bind to mouse IgG2b subclass molecules. The present invention also provides single-domain antibodies which recognize mouse IgG3 subclass molecules, selected from the single-domain antibodies of SEQ ID NOs: 32 and 33, whereby SEQ ID NO: 33 specifically recognizes mouse IgG3 subclass molecules. Nanobodies® of the present invention may also be able of binding specifically to the mouse light chain, independently of the heavy chain of the IgG subclass (single-domain antibodies of SEQ ID NOs: 3-7). For example, specific anti-kappa chain single-domain antibodies of the invention may be selected from single-domain antibodies of SEQ ID NOs: 3-6.

Preferred embodiments of preferred anti-IgG single-domain antibodies of the invention specific for particular IgG subclasses are shown in Table 3:

TABLE 3

| Grouping Feature | Group Name | SEQ ID No. | Group Description |
|---|---|---|---|
| Binding to a particular IgG subclass | All Mouse IgG1 | SEQ ID No. 3-24 | Binding to Mouse IgG1 |
| | All Mouse IgG2a | SEQ ID No. 20-30, 34 | Binding to Mouse IgG2a |
| | All Mouse IgG2b | SEQ ID No. 24, 30-32 | Binding to Mouse IgG2b |
| | All Mouse IgG3 | SEQ ID No. 32 and 33 | Binding to Mouse IgG3 |
| | All Mouse light chain | SEQ ID No. 3-7 | Binding to Mouse Light chain independently of heavy chain subclass |
| | All Mouse Kappa chain | SEQ ID No. 3-6 | Binding to Mouse Kappa chain independently of heavy chain subclass |

The single-domain antibodies of the present invention are further characterized by high binding specificity for different binding regions of the IgG molecules, e.g. specifically targeting epitopes on the mouse kappa and/or lambda light chain or the mouse Fc, hinge or Fab fragment on the IgG molecules. Some of single-domain antibodies may have mixed specificities, e.g. may be mouse Fab-binders, which target an interface between a kappa and/or lambda light chain and an IgG, e.g. IgG1, IgG2a or IgG2b, heavy chain. For example, single-domain antibodies of the present invention specifically binding to an epitope comprising a portion of the K and/or A light chain of mouse IgG molecules may be selected from single-domain antibodies of SEQ ID NOs: 3-7, 19-24 and 31-32. Anti-IgG single-domain antibodies of the present invention specifically targeting an epitope on the Fc fragment of mouse IgG molecules may be selected from single-domain antibodies of SEQ ID NOs: 8-17, 25-28, 30 and 33-34. In particular, single-domain antibodies of SEQ ID NOs: 8-17 target to a mouse IgG1 Fc fragment, single-domain antibodies of SEQ ID NOs: 25-28, 30 and 34 bind to mouse IgG2a Fc fragment and single-domain antibodies of SEQ ID NOs: 33 and 34 recognize an epitope location on the Fc fragment of IgG3 subclass molecules.

Table 4 indicates preferred embodiments of preferred anti-IgG single-domain antibodies targeting specific epitope regions on particular IgG sbtype molecules:

TABLE 4

| Grouping Feature | Group Name | SEQ ID No. | Group Description |
|---|---|---|---|
| Binding to a particular region on IgG | All Mouse IgG1 Fab | SEQ ID No. 3-7, 20-24 | Binding to Mouse IgG1 Fab fragment |
| | All Mouse IgG1 Fc | SEQ ID No. 8-17 | Binding to Mouse IgG1 Fc fragment |
| | All Mouse IgG2a FC | SEQ ID No. 25-28, 30, 34 | Binding to Mouse IgG2a Fc fragment |
| | All Mouse IgG2a Fab | SEQ ID No. 20-24 | Binding to Mouse IgG2a Fab fragment |
| | All Mouse IgG2b Fab | SEQ ID No. 31-32 | Binding to Mouse IgG2b Fab fragment |

The single-domain antibodies of the present invention can be characterized by a high target affinity and/or a very low off-rate. The target affinity may be in the range from low nanomolar to sub-picomolar, preferably below 10 nM, below 1 nM or below 100 pM as measured by quantitative phage display. This is supported by the following experimental observations. When titrating target IgG down to subpicomolar concentration, a stoichiometric phage retrieval during anti-IgG single-domain antibody selections was observed, arguing for a non-affinity limited process. Off-rate selections using high excesses of competitor IgG showed no significant Nanobody®-IgG complex dissociation over a course of 4 h. Similarly, we observed no spectral intermixing during one-step co-immunolocalizations with differentially labeled, pre-formed IgG-Nanobody® complexes. Due to their low off-rate, the anti-IgG single-domain antibodies remain bound to their target even after extended washing procedures.

Further, the single-domain antibodies of the present invention can be characterized by a weak crossreactivity to IgGs from other species, e.g. from rat, guinea pig or from humans. According to a preferred embodiment of the invention the single-domain antibodies show a crossreaction of 15% or less, preferably of 10% or less, more preferably of 5% or less to IgGs from other species, in particular to IgGs from rats, guinea pigs or humans, especially to IgGs from humans. In a very preferred embodiment of the invention the single-domain antibodies are exclusively specific to rabbit and/or mouse IgG molecules and show no crossreaction to IgGs from other species, in particular to human IgGs. The crossreactivity of the anti-IgG single-domain antibodies of the present invention is measured by conventional methods, such as fluorescent dot blots or ELISA. A specificity profiling dot blot assay of the anti-IgG single-domain antibodies of the present invention to analyze their crossreaction to IgG from other species is described in Example 1.5 and FIG. 1—supplement 1a.

The single-domain antibodies of the invention may be genetically modified, e.g. by incorporating an additional cysteine residue at the N-terminus and/or at the C-terminus and/or other surface-exposed positions within the framework region. This facilitates coupling to heterologous moieties via the SH-side chain of cysteine.

Further, the present invention refers to conjugates of the above single-domain antibodies. Such conjugates may be genetic fusions, wherein the Nanobody® is conjugated via peptide bonds to a heterologous peptide or protein sequence. Examples of heterologous protein sequences are peroxidases such as class I peroxidases, e.g. APEX2, or phosphatases (e.g. lambda phosphatase; alkaline phosphatase), or luciferase.

On the other hand, the conjugate may comprise heterologous moieties, e.g. proteinaceous moieties and/or non-proteinaceous moieties coupled to amino acid side chains, e.g. thiol, amino, guanidino, carboxy or hydroxy groups on amino acid side chains, or other reactive groups such as azide or alkyne groups on modified amino acid side chains, and/or to the N- or C terminus by non-peptidic bonds. Suitable conjugation partners are labelling groups, e.g. enzyme reporter groups as described above or fluorescent labelling groups, solid phase-binding groups such as streptavidin or biotin.

In a preferred embodiment, one, two or three labelling groups, e.g. fluorescent labelling groups may be coupled to the side chain of cysteine residues. In a further specific embodiment, one, two or three enzyme reporter groups such as horseradish peroxidase or phosphatases may be coupled to the side chain of cysteine residues.

In a further preferred embodiment, one, two or three labelling groups, e.g. fluorescent labelling groups may be coupled to the side chain of lysine residues. In a further specific embodiment, one, two or three enzyme reporter groups such as horseradish peroxidase or phosphatases may be coupled to the side chain of lysine residues.

A further aspect of the present invention relates to a nucleic acid molecule encoding a single-domain antibody as indicated above. The nucleic acid may be a double stranded or single stranded nucleic acid, e.g. DNA or RNA. The nucleic acid molecule encoding the single-domain antibody may be an operative linkage with an expression control sequence, in particular with an expression control sequence which is heterologous to a native single-domain antibody expression control sequence.

The nucleic acid molecule can be incorporated in a prokaryotic or eukaryotic vector suitable for transfecting or transforming hosts, e.g. host cells, e.g. bacterial cells such as E. coli, or eukaryotic host cells, e.g. yeast cells (e.g. S. cerivisiae or Pichia pastoris), insect cells or mammalian cells, e.g. cultured mammalian cells (e.g. HEK-293, HeLa or CHO cells). For this purpose, the nucleic acid molecule may have a codon-optimized sequence with regard to expression in the desired host. Suitable non-human host organisms include multicellular organisms, e.g. mammals, such as mice, rabbits, rats. Suitable types of vectors include plasmids, phages, phagemids, viruses etc. as known to the skilled person. In a preferred embodiment, the vector is a prokaryotic expression vector.

Still a further aspect of the invention is a recombinant cell or recombinant non-human organism transformed or transfected with a nucleic acid molecule or a vector as indicated above. Preferably, the cell or non-human organism is capable of expressing the single-domain antibody of the invention.

The single-domain antibodies of the present invention are particularly suitable for detection, purification and/or isolation of IgG molecules. Specific embodiments include purification and/or isolation of IgG from biological fluids such as blood, plasma, serum or all culture supernatant, detection, purification and/or isolation of IgG-antigen-complexes, immunofluorescence procedures including indirect one-step-immunofluorescence, e.g. by premixing of anti-IgG single-domain antibodies with primary antibodies, indirect one-step co-localisations, e.g. by using different primary antibodies with differently labelled anti-IgG single-domain antibodies, immunoblots with labelled, e.g. fluorescence-labelled and/or enzyme-labelled anti-IgG single-domain antibodies, immunoassays, e.g. in the ELISA format, with labelled, e.g. enzyme-labelled anti-IgG single-domain antibodies etc. Further, the single-domain antibodies can also be used as intracellular antibodies, i.e. intrabodies.

The single-domain antibodies of the invention may be used alone or as combinations comprising several different single-domain antibodies, e.g. a single-domain antibody directed against an Fc fragment of a specific IgG subtype such as mouse IgG1 may be combined with a single-domain antibody directed against the same IgG subtype such as mouse IgG1, but against a different epitope, e.g. Fab, hinge etc. Alternatively, combinations of single-domain antibodies directed against different subtypes of IgG, e.g. IgG1 and IgG2a, preferably each carrying a different reporter and/or labelling group, are provided. These combinations of compatible single-domain antibodies provide strong signal amplification and may be used for immunostaining, e.g. in multi-colour immunostaining (co-localizations of multiple targets) or immunoblotting detecting e.g. two or more antigens at the same time.

Thus, the invention encompasses combinations of several single-domain antibodies.

In one embodiment, the combination comprises at least 2 single-domain antibodies, e.g. 2 or 3 single-domain antibodies each recognizing the same type of IgG molecules, e.g. mouse IgG1, mouse IgG2a or rabbit IgG, wherein individual single-domain antibodies of said combination bind to non-overlapping epitopes on the IgG molecules, e.g. respectively to the kappa and/or lambda light chain or to the Fab, Fc or hinge fragment of the IgG molecules. For example, a combination of single-domain antibodies recognizing mouse IgG1 may be selected from the single-domain antibodies of SEQ ID NO: 5 and 8, SEQ ID NO: 8 and 19, SEQ ID NO: 18 and 19 and SEQ ID NO: 5 and 18 or single-domain antibodies comprising at least the CDR3 sequences thereof. A combination of single-domain antibodies recognizing mouse IgG2a may be selected from the single-domain antibodies of SEQ ID NO: 5 and 25 or single-domain antibodies comprising at least the CDR3 sequences thereof. A combination of single-domain antibodies recognizing rabbit IgG may be selected from the single-domain antibodies of SEQ ID NO: 1 and 2 or single-domain antibodies comprising at least the CDR3 sequences thereof. The simultaneous use of combinations of two or more of such single-domain antibodies results in an adequate signal amplification in applications like immunofluorescence and immunoblotting.

Table 5 indicates preferred embodiments of combinations of anti-IgG single-domain antibodies of the invention directed to the same IgG subtype molecules but individually binding to non-overlapping epitopes on the IgG molecules:

TABLE 5

| Grouping Feature | Group Name | SEQ ID No. | Group Description |
|---|---|---|---|
| Additive Signal Strength | Boost mouse IgG1 | SEQ ID No. 5 and SEQ ID No. 8 | Mouse Kappa chain and IgG1 Fc Binder, non-overlapping epitopes |
| | Boost mouse IgG1 | SEQ ID No. 8 and SEQ ID No. 19 | Mouse IgG1 Fc and IgG1 Fab Binder, non-overlapping epitopes |
| | Boost mouse IgG1 | SEQ ID No. 18 and SEQ ID No. 19 | Mouse IgG1 Hinge and IgG1 Fab Binder, non-overlapping epitopes |
| | Boost mouse IgG1 | SEQ ID No. 5 and SEQ ID No. 18 | Mouse Kappa chain and IgG1 Hinge Binder, non-overlapping epitopes |
| | Boost mouse IgG2a | SEQ ID No. 5 and SEQ ID No. 25 | Mouse Kappa chain and IgG2a Fc Binder, non-overlapping epitopes |
| | Boost rabbit IgG | SEQ ID No. 1 and SEQ ID No. 2 | Rabbit IgG Fab and Fc Binder, non-overlapping epitopes |

Further, the invention encompasses combinations of single-domain antibodies which recognize IgG molecules of different types without cross-reaction, e.g. a single-domain antibody recognizing mouse IgG1 and/or a single-domain antibody recognizing mouse IgG2a and/or a single-domain antibody recognizing rabbit IgG as described above. When appropriately labeled, such a combination of single-domain antibodies can be used for colocalizations in immunofluorescence or multiplexing in immunoblotting.

The single-domain antibodies of the invention may also be provided as a preformed immune complex with an IgG antibody directed against an antigen of interest. Due to their high target affinity and/or low off-rate, the immunocomplexes are stable and can be preformed before use. The immunocomplexes may be used alone or as combinations comprising several different immunocomplexes, e.g. immunocomplexes comprising different IgG antibodies each complexed with a specific single-domain antibody. The single-domain antibodies may be directed against the same IgG subtype or against different IgG subtypes. Thus, combinations of different preformed complexes, preferably each carrying a different reporter and/or labelling group, are provided. These complexes and combinations may be used for immunostaining, e.g. in multi-colour immunostaining or immunoblotting.

Thus, the invention encompasses combinations comprising differently labeled versions of the same single-domain antibody, each bound to different IgG molecules of the same type, but recognize different antigens. Such combinations of pre-formed immune complexes may be used for colocalizations in immunofluorescence or multiplexing in immunoblotting.

The single-domain antibodies of the present invention can be produced in bacteria such as *E. coli*. They provide reproducible quality, since they are defined by means of their sequence, thus obviating the use of immune sera, i.e. varying mixtures of polyclonal antibodies.

The single-domain antibodies of the present invention have advantageous properties in view of known anti-IgG single-domain antibodies, e.g. as commercially available from Abcam. These advantages are demonstrated in the present examples.

Further, the invention is explained in more detail by the following figures and examples:

Characterization of the anti-IgG single-domain antibody toolbox.

Figure 1:
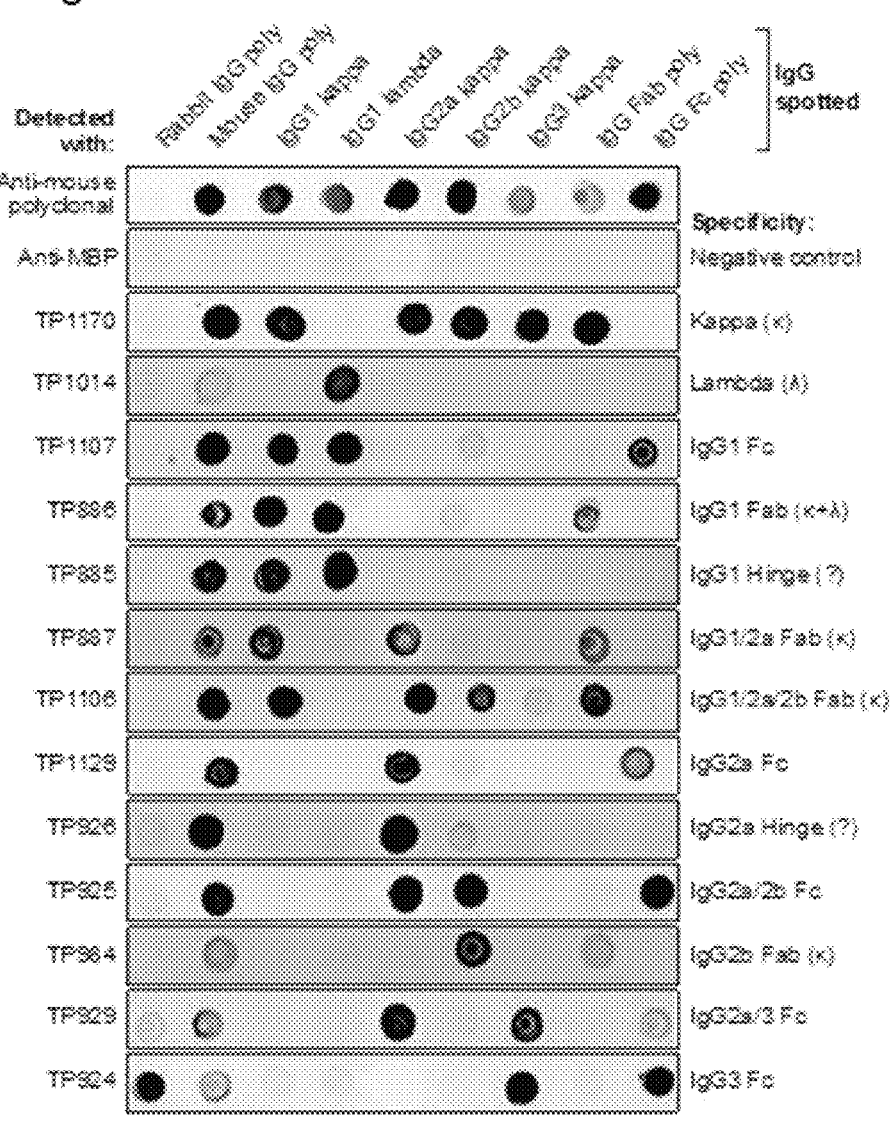
FIG. 1.

(a) Overview of selected anti-IgG single-domain antibodies identified according to the invention. The obtained single-domain antibodies were characterized for IgG subclass specificity, epitope location on Fab or Fc fragment and species crossreactivity (FIG. 1—figure supplement 1). The protein sequences of all anti-IgG single-domain antibodies can be found in Table 2. Nb=Nanobody®; CDR3=Complementarity-determining region 3; Gp=Guinea pig; Hs=Human; κ=kappa light chain; λ=lambda light chain; Fab=Fragment antigen-binding, Fc=Fragment crystallizable.

(b) IgG subclass reactivity profiling of selected anti-mouse IgG single-domain antibodies representing all identified specificity groups. The indicated IgG species were spotted on nitrocellulose strips and the strips blocked with 4% (w/v) milk in 1×PBS. Then 300 nM of the indicated tagged single-domain antibodies were added in milk. After washing with 1×PBS, bound single-domain antibodies were detected using a fluorescent scanner. Note that the signal strength on poylclonal IgG depends on the relative abundance of the specific subclass (e.g. IgG2b and IgG3 are low-abundant) or light chain (kappa: lambda ratio=99:1). TP885 and TP926 showed no detectable binding to polyclonal Fab or Fc fragment and might bind to the hinge region. MBP=maltose binding protein; poly=polyclonal.

FIG. 1—figure supplement 1.

Species crossreactivity profiling and native target IgG isolation.

(a) Crossreactivity profiling of anti-IgG single-domain antibodies. Using the same Dot blot assay as described in FIG. 1*b*, the crossreactivity of anti-IgG single-domain antibodies to polyclonal IgG from the indicated species was determined.

(b) Isolation of polyclonal rabbit IgG from rabbit serum. Anti-rabbit IgG single-domain antibodies TP896 and TP897 carrying an N-terminal Avi-SUMOStar tag were biotinylated and immobilized on magnetic Streptavidin beads. After incubation with crude rabbit serum and washing, Nanobody®-bound polyclonal rabbit IgG was specifically eluted via SUMOStar protease cleavage in physiological buffer. Empty beads served as negative control.

(c) Isolation of anti-Nup62 mouse IgG1 kappa mAb A225 from hybridoma supernatant with anti-mouse IgG1 single-domain antibodies TP881 and TP885 as described in a. The asterisk indicates the SUMOStar protease used for elution.

FIG. 2.

Application of peroxidase-linked anti-IgG single-domain antibodies.

(a) A twofold dilution series of *Xenopus laevis* egg extract was blotted and probed with anti-Nup62 mouse IgG1 mAb A225. It was then decorated with horseradish peroxidase (HRP)-conjugated goat anti-mouse polyclonal IgG (5 nM) or anti-mouse IgG1 Fc single-domain antibody TP1107 (5 nM) and detected via enhanced chemiluminescence (ECL). Similarly, a rabbit polyclonal antibody targeting Nup54 was decorated with HRP-conjugated goat anti-rabbit polyclonal IgG or anti-rabbit IgG single-domain antibody TP897 (5 nM).

(b) A twofold dilution series of *Xenopus* egg extract was blotted on nitrocellulose and probed with an anti-Nup62 mouse IgG1 monoclonal antibody (upper panel). It was then detected either via HRP-conjugated anti-mouse IgG1 single-domain antibody ab193651 (Abcam, United Kingdom, used at 1:3,500 dilution, ~5 nM) or 5 nM anti-mouse IgG1 Fc single-domain antibody TP1107. For this, TP1107 was conjugated to maleimide-activated HRP (#31485, Thermo Fisher Scientific, USA) via a C-terminal cysteine by incubating both in equimolar amounts for 1 h at room temperature. The blot was developed using Enhanced chemiluminescence (ECL). (Lower panels) A twofold dilution series of *Xenopus* egg extract was blotted on nitrocellulose and probed with polyclonal rabbit antibodies against Nup54 or Nup107. They were then detected either via HRP-conjugated anti-rabbit IgG single-domain antibody ab191866 (Abcam, United Kingdom, used at 1:3,500 dilution, ~5 nM) or 5 nM anti-rabbit IgG single-domain antibody TP897. TP897 was conjugated to HRP as described above and the blot developed by ECL.

(c) Oxidation of the fluorogenic ELISA substrate Amplex™ UltraRed. A dilution series of pure HRP or recombinant anti-mouse IgG1 Fc single-domain antibody TP1107-Ascorbate peroxidase (APEX2) fusion was incubated with Amplex™ UltraRed and $H_2O_2$. Oxidation leads to formation of the fluorescent compound resorufin. The obtained data were fitted with a four-parameter logistic regression. The inflection points of the curves can be used to compare attainable sensitivity. A.U.=arbitrary units.

Figure 2:
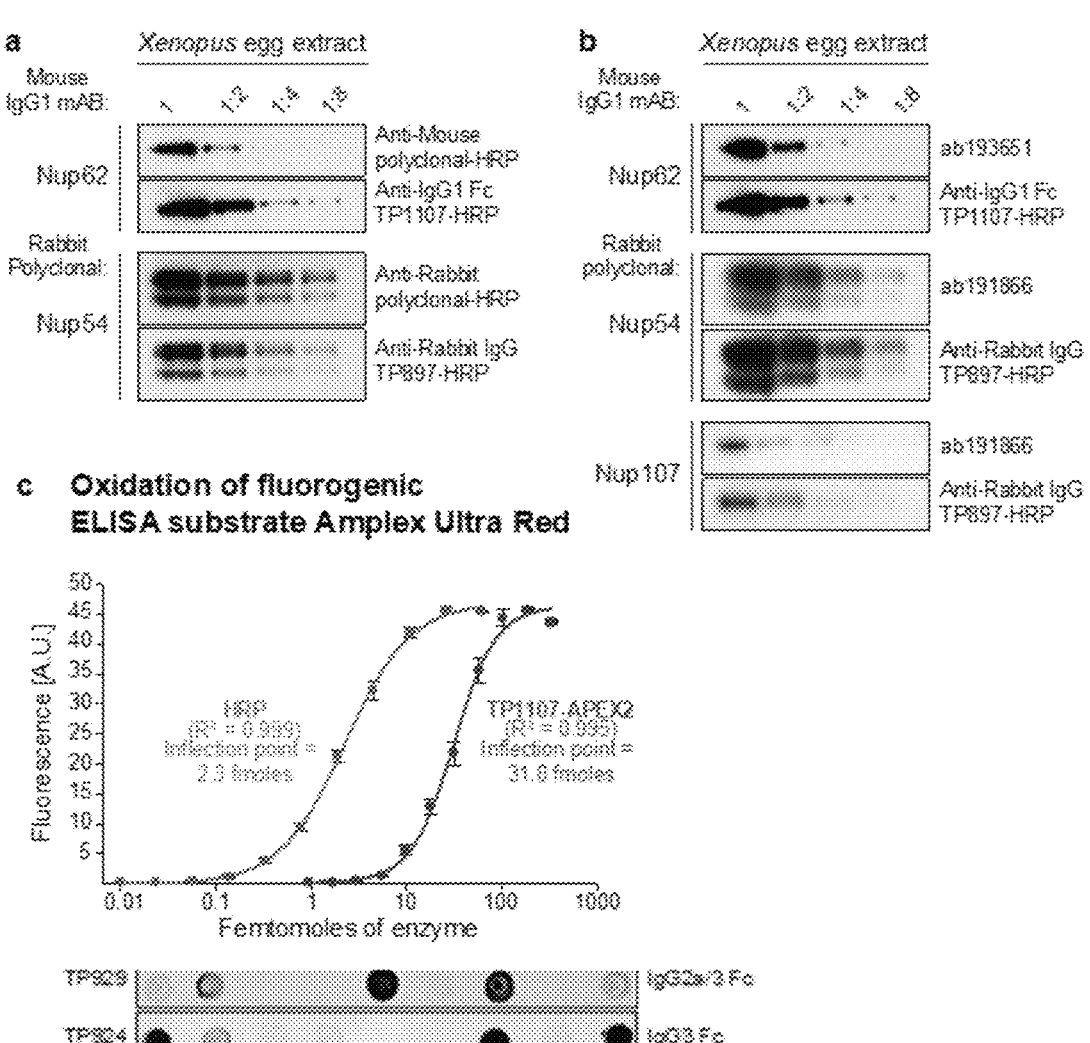

FIG. 2—figure supplement 1.

Anti-IgG single-domain antibody conjugation to HRP and fusion to APEX2.

(a) Anti-mouse IgG1 Fc single-domain antibody TP1107 with a C-terminal cysteine was conjugated to maleimide-activated horseradish peroxidase (HRP) by incubation of equimolar amounts for 1 h at room temperature.

(b) Expression of anti-mouse IgG1 Fc single-domain antibody TP1107-ascorbate peroxidase (APEX2) fusion in *E. coli*. After binding to nickel beads via the N-terminal $His_{14}$-bdNEDD8-tag, untagged fusion protein was eluted by on-column bdNEDP1 cleavage (Frey and Görlich, 2014).

FIG. 3.

Western blotting with infrared dye labeled anti-IgG single-domain antibodies.

(a) A twofold dilution series of *Xenopus laevis* egg extract was analyzed by SDS-PAGE and Western Blotting. The indicated rabbit polyclonal antibodies were used to detect nucleoporins (Nups). These primary antibodies were then decorated either via IRDye® (near-infrared fluorescent dye) 800-labeled goat anti-rabbit polyclonal IgG (1:5,000; LI-COR Biosciences, USA) or anti-rabbit IgG single-domain antibody TP897 (10 nM). Blots were analyzed with an Odyssey Infrared Imaging System (LI-COR Biosciences, USA).

(b) (Left panel) A twofold dilution series of HeLa cell lysate was analyzed by SDS-PAGE and Western Blotting. The indicated mouse IgG1 mAbs were decorated either via IRDye® 800-labeled goat anti-mouse polyclonal IgG (1:1, 340, 5 nM, LI-COR Biosciences, USA) or anti-mouse IgG1 Fc single-domain antibody TP1107 (5 nM). (Right panel) A twofold dilution series of *Xenopus* egg extract was blotted and probed with anti-Nup62 mouse IgG1 mAb A225. It was then detected either via IRDye® 800-labeled goat anti-mouse polyclonal IgG (5 nM), anti-mouse IgG1 Fc single-domain antibody TP1107 (5 nM), anti-mouse IgG1 Fab single-domain antibody TP886 (5 nM), anti-mouse kappa chain single-domain antibody TP1170 (2.5 nM), a combination of TP1107 and TP886 or TP1107 and TP1170. Blue pixels indicate signal saturation.

(c) A dilution series of filamentous bacteriophages was blotted and probed with an anti-minor coat protein pill mouse IgG2a mAb. It was then decorated either via IRDye® 800-labeled goat anti-mouse polyclonal IgG (2.5 nM) or anti-mouse kappa chain single-domain antibody TP1170 (2.5 nM).

FIG. 4.

Imaging with anti-IgG single-domain antibodies.

(a) Immunofluorescence with anti-mouse IgG1 single-domain antibodies. HeLa cells were stained with the indicated mouse IgG1 kappa mAbs. These primary antibodies were then detected with Alexa 488-labeled goat anti-mouse polyclonal antibody, anti-mouse IgG1 Fab single-domain antibody TP886 (SEQ ID NO:19) or anti-mouse IgG1 Fc single-domain antibody TP1107 (SEQ ID NO:8). A combination of TP886 (SEQ ID NO:19) and TP1107 (SEQ ID NO:8) yielded increased staining intensities. Laser intensities used to acquire the anti-IgG single-domain antibody images were normalized to the intensity used to acquire the anti-mouse polyclonal antibody image (RLI=relative laser intensity is used here as a measure of fluorescence signal strength).

(b) Immunofluorescence with anti-mouse IgG2a single-domain antibodies. HeLa cells were stained with the indicated mouse IgG2a mAbs. These primary antibodies were then detected with Alexa 488-labeled goat anti-mouse polyclonal antibody, anti-mouse IgG2a Fc single-domain antibody TP1129 (SEQ ID NO:25) or anti-kappa chain single-domain antibody TP1170 (SEQ ID NO:5). A combination of TP1129 (SEQ ID NO:25) and TP1170 (SEQ ID NO:5) yielded increased staining intensities. (c) Immunofluorescence with anti-rabbit IgG single-domain antibody TP897 (SEQ ID NO: 2). HeLa cells were stained with the indicated rabbit antibodies. These primary antibodies were then detected with Alexa 488-labeled goat anti-rabbit polyclonal antibody or anti-rabbit IgG single-domain antibody TP897 (SEQ ID NO:2). (d) Multicolor-staining of Hela cells. Hela cells were incubated with the indicated mouse IgG1, mouse IgG2a or rabbit IgG antibodies. These primary antibodies were detected via anti-mouse IgG1 Fc single-domain antibody TP1107 (SEQ ID NO:8), anti-mouse IgG2a Fc single-domain antibody TP1129 (SEQ ID NO:25) or anti-rabbit IgG single-domain antibody TP897 (SEQ ID NO:2), respectively, labeled with the indicated Alexa dyes. The upper two panels show dual and the lower panel shows a triple co-localization.

Figure 4:
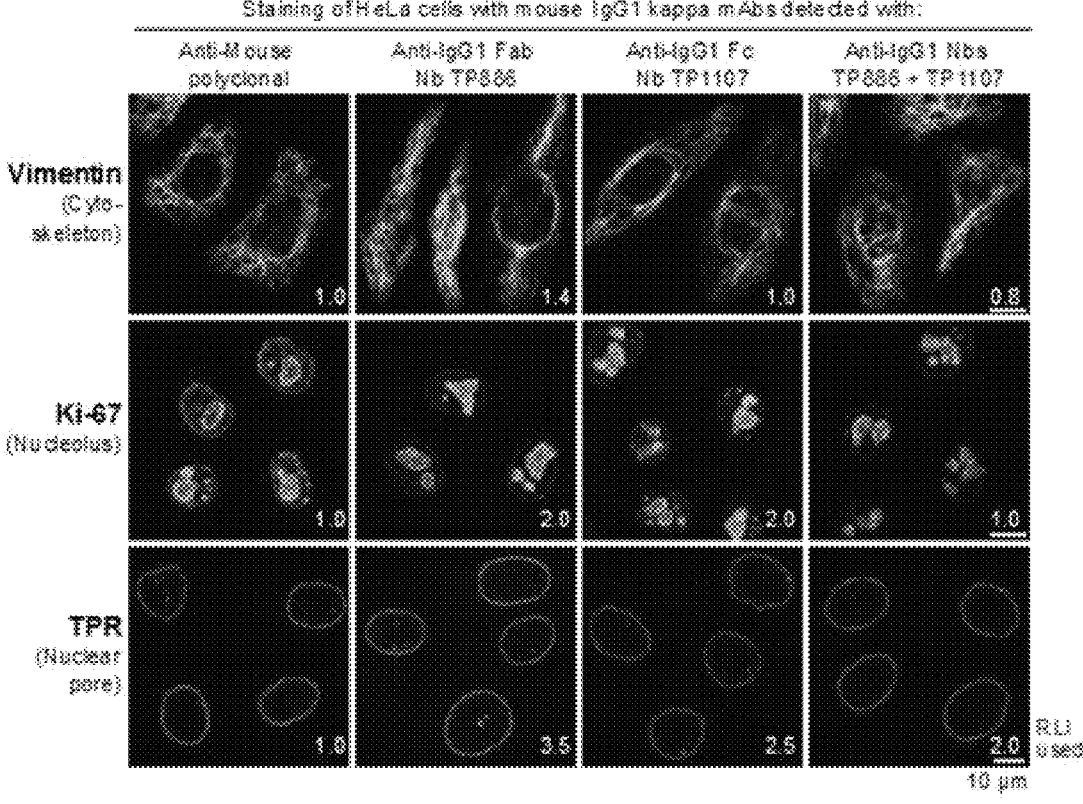
Figure 4:
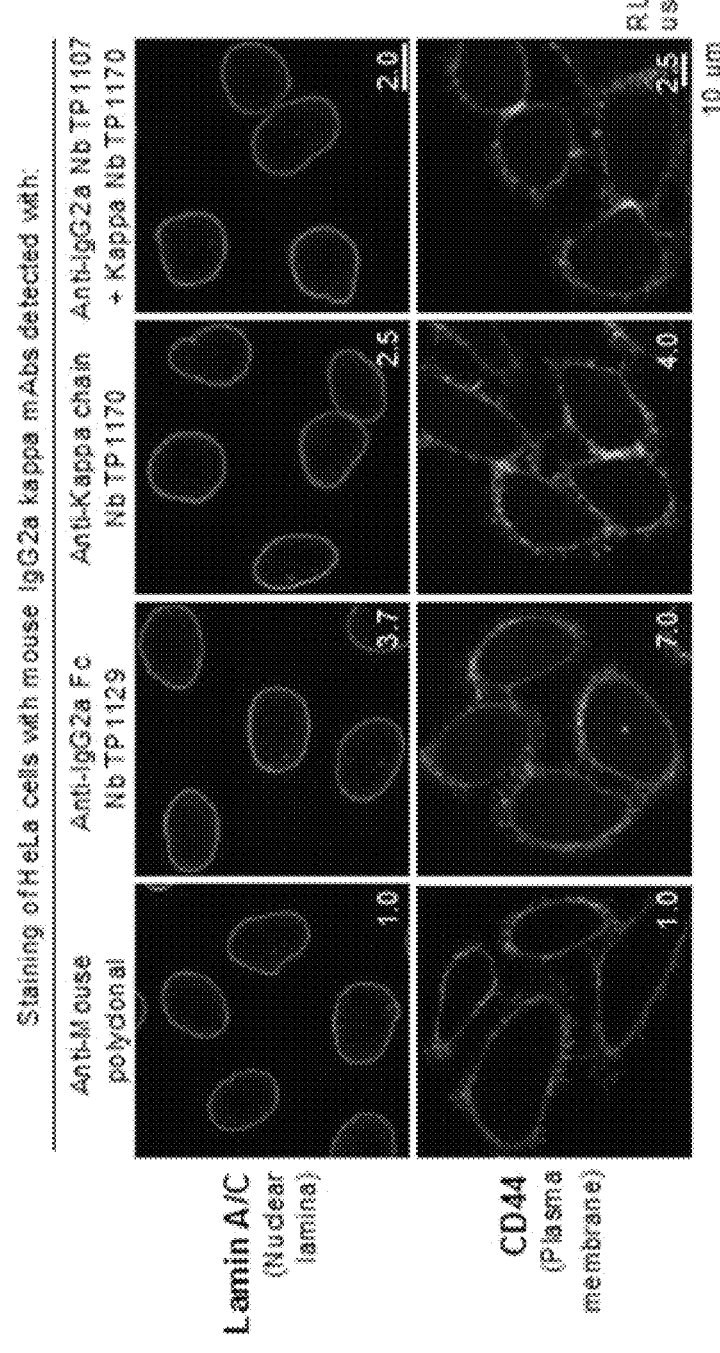
Figure 4:
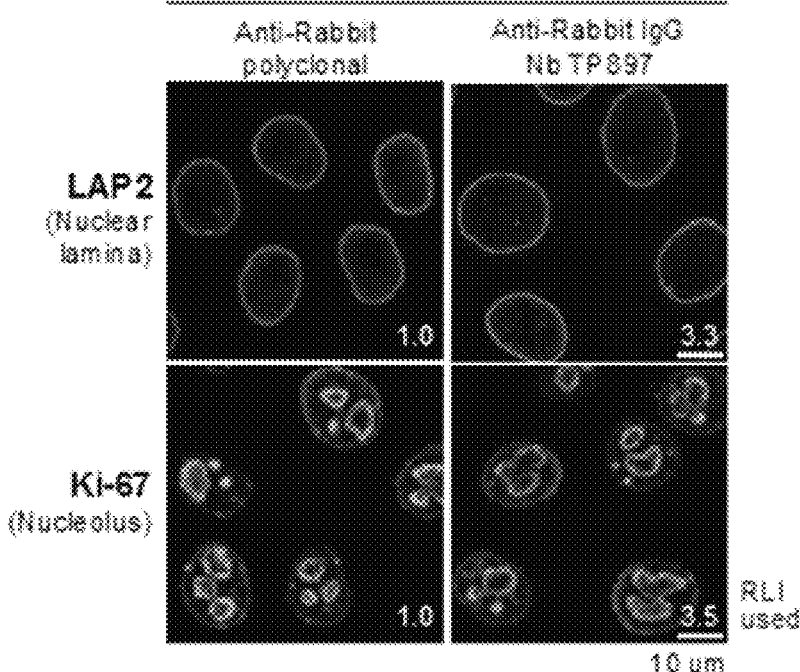
Figure 4:
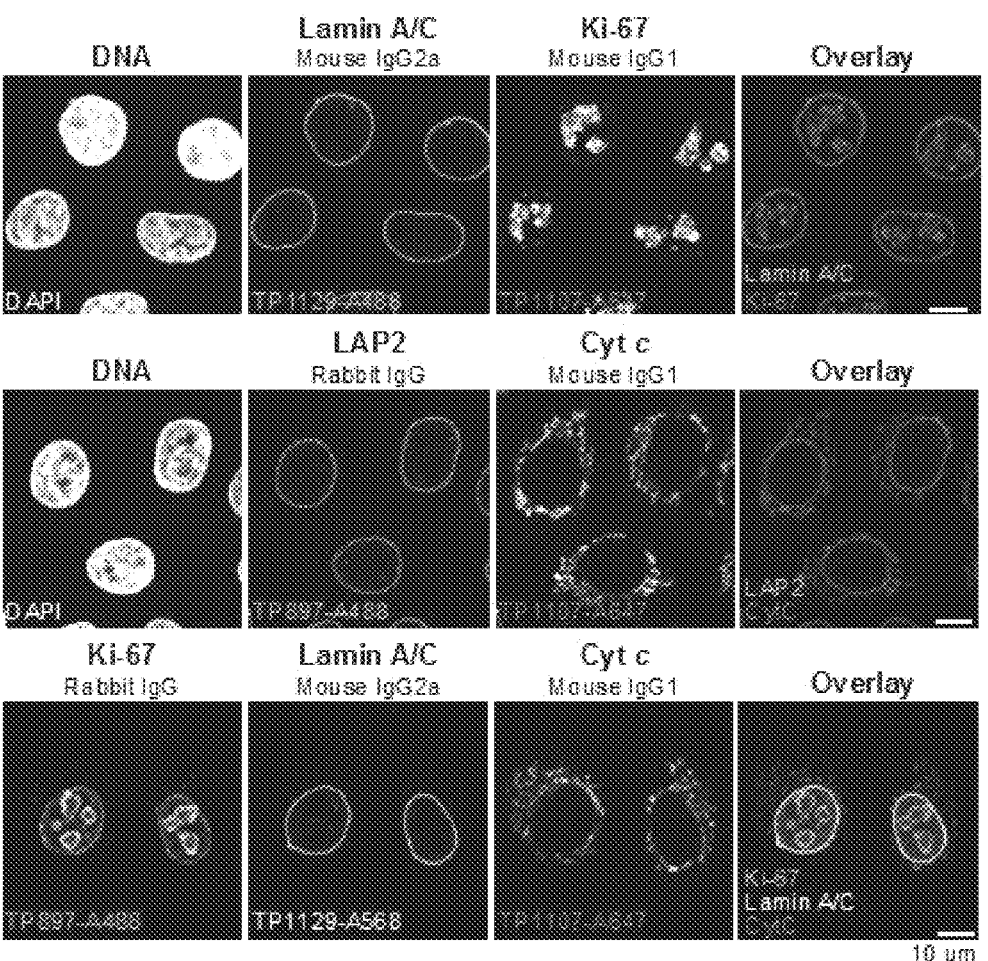

FIG. 4—figure supplement 1.

Immunofluorescence with anti-mouse IgG single-domain antibodies.

(a-b) Images for a given mAb or polyclonal antibody were acquired under identical settings and pixel intensities are represented via a false-color lookup table. (a) HeLa cells were stained with the indicated mouse IgG1 mAbs. These primary antibodies were then detected with Alexa 488-labeled goat anti-mouse polyclonal antibody or a combination of anti-mouse IgG1 Fab single-domain antibody TP886 and anti-mouse IgG1 Fc single-domain antibody TP1107 (SEQ ID NO:8). (b) Hela cells were stained with the indicated mouse IgG2a mAbs. These primary antibodies were then detected with Alexa 488-labeled goat anti-mouse polyclonal antibody or a combination of anti-mouse IgG2a Fc single-domain antibody TP1129 and anti-kappa chain Nanobody® TP1170 (SEQ ID NO:5).

(c) Protein sequence alignment of anti-mouse IgG2a single-domain antibody TP921 (SEQ ID NO:26; and the corresponding Framework I "SEQ ID NO:217," CDR1 "SEQ ID NO: 218," Framework II "SEQ ID NO:219," CDR2 "SEQ ID NO:220," Framework III "SEQ ID NO:221," CDR3 "SEQ ID NO:222," and Framework IV "SEQ ID NO:223") and the variant TP1129 (SEQ ID NO:25; and the corresponding Framework I "SEQ ID NO: 211," CDR1 "SEQ ID NO:212," Framework II "SEQ ID NO:213," CDR2 "SEQ ID NO: 214," Framework III "SEQ ID NO:215," CDR3 "SEQ ID NO:57," and Framework IV "SEQ ID NO:216") obtained after affinity maturation. Hela cells were stained with a mouse IgG2a mAb targeting Lamin A/C. The mAb was detected via TP921 (SEQ ID NO:26) or TP1129 (SEQ ID NO:25) labeled with a single Alexa 488 dye and the images acquired under identical settings.

(d) Protein sequence alignment of anti-mouse kappa chain single-domain antibody TP974 (SEQ ID NO:3; and the corresponding Framework I "SEQ ID NO:78," CDR1 "SEQ ID NO:79," Framework II "SEQ ID NO:80," CDR2 "SEQ ID NO:81," Framework III "SEQ ID NO:82," CDR3 "SEQ ID NO:83," and Framework IV "SEQ ID NO: 84") and the variant TP1170 (SEQ ID NO:5; and the corresponding Framework I "SEQ ID NO:91," CDR1 "SEQ ID NO:92," Framework II "SEQ ID NO: 93," CDR2 "SEQ ID NO:94," Framework III "SEQ ID NO:95," CDR3 "SEQ ID NO: 37," and Framework IV "SEQ ID NO:96") obtained after DNA shuffling and affinity maturation. Hela cells were stained with a mouse IgG2a mAb targeting Lamin A/C. The mAb was detected via TP974 (SEQ ID NO:3) or TP1170 (SEQ ID NO: 5), both labeled with two Alexa 488 dyes.

(e) Hela cells were stained with the indicated mouse IgG1 kappa mAbs. These primary antibodies were then detected with Alexa 647-labeled goat anti-mouse polyclonal antibody, anti-mouse IgG1 Fc single-domain antibody TP1107 (SEQ ID NO: 8) or anti-mouse kappa chain Nanobody® TP1170 (SEQ ID NO:5). A combination of TP1107 (SEQ ID NO:8) and TP1170 (SEQ ID NO:5) yielded increased staining intensities, see (f) for identical settings scan. RLI=relative laser intensity (as defined in FIG. 4a).

FIG. 5.

One-step immunostaining of Hela cells with anti-IgG single-domain antibodies.

(a) The indicated mouse IgG1 mAbs were pre-incubated with an equal amount of Alexa 488-labeled goat anti-mouse secondary antibody or a combination of anti-mouse IgG1 Fab single-domain antibody TP886 (SEQ ID NO:19) and anti-mouse IgG1 Fc single-domain antibody TP1107 (SEQ ID NO:8). Likewise, the anti-LAP2 rabbit polyclonal antibody was pre-incubated either with Alexa 488-labeled goat anti-rabbit secondary antibody or anti-rabbit IgG single-domain antibody TP897 (SEQ ID NO: 2). The resulting mixes were then applied to fixed and blocked Hela cells. After washing, the cells were directly mounted for imaging. For every primary antibody, images were acquired under identical settings and pixel intensities are represented via a false-color lookup table.

(b) Multicolor-staining of HeLa cells with mouse IgG1 subclass mAbs. The indicated mouse IgG1 mAbs were separately pre-incubated with Alexa 488, Alexa 568 or Alexa 647-coupled anti-mouse IgG1 Fc single-domain antibody TP1107 (SEQ ID NO: 8) and then mixed before staining Hela cells in a single step. Washed cells were directly mounted for imaging.

DETAILED DESCRIPTION

Examples

1. Methods 1.1 Alpaca Immunization

Two female alpacas, held at the Max Planck Institute for Biophysical Chemistry, were immunized 4 times with 1.0 mg polyclonal mouse or rabbit IgG at 3 week intervals. The anti IgG project turned out to be the so far most challenging single-domain antibody project in the lab, because we aimed at an extremely low off-rate for imaging and blotting applications. We therefore resumed immunizations after a 12 months (rabbit IgG) or an 8 months break (mouse IgG). Single-domain antibodies obtained after these late immunizations still showed very clear phage enrichment (>1000-fold) even with femtomolar concentrations of the IgG baits. We therefore assume that they have very high affinity.

1.2 Selection of Anti-IgG Single-Domain Antibodies

The generation of single-domain antibody immune libraries and the selection of antigen-specific single-domain antibodies by phage display from these libraries were performed as previously described (Pleiner et al., 2015). IgG was biotinylated at accessible lysines by addition of a 4× molar excess of NHS-PEG$_{12}$-biotin (Iris Biotech GmbH, Germany) for 2 h at room temperature in 1×PBS. Then the reaction was quenched and the excess of unreacted biotin separated from biotinylated IgG via buffer exchange into 50 mM Tris/HCl PH 7.5, 300 mM NaCl using PD-10 Desalting columns (GE Healthcare, USA).

1.3 Expression and Purification of Untagged Single-Domain Antibodies

Single-domain antibodies with engineered cysteines were expressed in the cytoplasm of E. coli NEB express F' (New England Biolabs, USA). A 50 ml preculture (2YT medium containing 50 μg/ml Kanamycin) was grown overnight at 28° C. The culture was then diluted with fresh medium to 250 ml. After 1 h of growth at 25° C., protein expression was induced for 3-5 h by adding 0.2 mM IPTG. After addition of 1 mM PMSF and 10 mM EDTA to the culture, bacteria were harvested by centrifugation, resuspended in lysis buffer (50 mM Tris/HCl PH 7.5, 300 mM NaCl, 10 mM imidazole, 5 mM DTT) and then lysed by sonication. The lysate was cleared by ultracentrifugation for 1.5 h (T647.5 rotor, Sorvall, 38,000 rpm) at 4° C. Single-domain antibodies with engineered cysteines carried an N-terminal His$_{14}$-bdNEDD8-tag and were affinity purified via Ni$^{2+}$ chelate affinity chromatography. After washing with two column volumes (CV) of lysis buffer and one CV of maleimide-labeling buffer (100 mM potassium phosphate pH 7.5, 150 mM NaCl, 1 mM EDTA, 250 mM Sucrose), untagged single-domain antibodies were eluted by on-column cleavage with 500 nM bdNEDP1 protease (Frey and Görlich, 2014) in maleimide-labeling buffer for 45 min at 4° C. and labeled immediately with fluorophores. For longer storage, 10 mM DTT or TCEP were included in the maleimide-labeling buffer to keep cysteines reduced. Purified single-domain antibodies were aliquoted and frozen in liquid nitrogen

1.4 Site-Specific Fluorescent Labeling of Single-Domain Antibodies with Engineered Cysteines The fluorescent labeling of single-domain antibodies with maleimide dyes was described in detail before (Pleiner et al., 2015). Briefly, stored single-domain antibodies were thawed and the buffer was exchanged again to Maleimide-labeling buffer to remove the reducing agent, using either illustra NAP-5 or PD-10 desalting columns (GE Healthcare). For a standard labeling reaction, 5-10 nmoles of single-domain antibody were rapidly mixed with 1.2× molar excess of fluorescent dye per cysteine on the single-domain antibody and incubated for 1.5 h on ice. Free dye was separated from labeled single-domain antibody by buffer exchange to Maleimide labeling buffer on illustra NAP-5 or PD-10 desalting columns. Quantitative labeling was quality controlled by calculating the degree of labeling (DOL). Fluorescently labeled single-domain antibodies were always aliquoted, snap-frozen in liquid nitrogen and stored at −80° C. until further use.

1.5 Dot Blot Assay for Anti-IgG Single-Domain Antibody Specificity Profiling For profiling the binding of anti-IgG single-domain antibodies to different IgG subclasses and to analyze their crossreaction to IgG from other species, a dot blot assay was performed. Nitrocellulose membrane was cut in strips and different IgGs (500 ng for polyclonal total IgG, Fab and Fc fragments; ~ 250 ng for monoclonal IgG in 1 μl) were spotted. Strips were blocked with 4% milk (w/v) in 1×PBS for 30 min at room temperature. Then, single-domain antibodies were added at ~300 nM in 1 ml milk for 30 min. After washing two times with 1×PBS for 10 min each, bound single-domain antibodies were detected at 488 nm in a fluorescence scanner (Starion FLA-9000, Fujifilm, Japan). The following IgGs were used: IgG1 kappa mAb A225 (Cordes et al., 1995); IgG1 lambda (#010-001-331, Rockland, USA); IgG2a kappa (#02-6200, Thermo Fisher Scientific, USA); IgG2b kappa (#02-6300, Thermo Fisher Scientific, USA); IgG3 kappa (#401302, BioLegend, USA); polyclonal IgG Fab fragments (#010-0105, Rockland, USA); polyclonal IgG Fc fragments (#31205, Thermo Fisher Scientific, USA). Polyclonal IgG of the following species were used: rabbit (self-made, affinity-purified from serum); mouse (#18765); rat (#14131); goat (#15256); sheep (#15131); human (#14506, all Sigma-Aldrich, USA) and guinea-pig (#CR4-10, Sino Biological, China).

1.6 Native Isolation of IgG with Anti-IgG Single-Domain Antibodies

Polyclonal rabbit IgG from serum or mouse mAbs from hybridoma cell culture supernatant were isolated natively with anti-IgG single-domain antibodies. For this, 0.3 nmoles of biotinylated single-domain antibodies carrying a N-terminal $His_{14}$-Biotin acceptor peptide-$(GlySer)_9$-SUMOStar-$(GlySer)_9$-tag were immobilized on 1 mg magnetic Dynabeads™ MyOne™ Streptavidin T1 (monosized, monodispersed, superparamagnetic beads, Thermo Fisher Scientific, USA). Excess biotin binding sites were quenched with biotin-PEG-COOH (#PEG1053, Iris Biotech, Germany). The beads were then incubated with 1 ml pre-cleared (10 min, 16,000 g at 4° C.) serum or hybridoma supernatant for 30 min at 4° C. After washing two times with wash buffer (50 mM Tris/HCl, 300 mM NaCl), Nanobody®-bound IgG was eluted by addition of 50 μl 0.5 μM SUMOStar protease (Liu et al., 2008) in wash buffer for 20 min on ice. An aliquot of the eluate was then analyzed by SDS-PAGE and Coomassie staining.

1.7 Western Blotting

Bacteriophage protein III was detected with a mouse anti-pIII IgG2a mAb (#E8033S, New England Biolabs, USA). Mouse mAbs used for detection of human proteins in HeLa cell lysate were the following products: anti-Skp1 (clone H-6, #sc-5281, Santa Cruz Biotechnology, USA), anti-a-tubulin (clone DM1A, #T6199, Sigma-Aldrich, USA) and anti-Histone H3 (clone 96C10, #3638, Cell Signaling Technologies, USA). Polyclonal goat anti-mouse IgG coupled to IRDye® 800CW (#925-32210; LI-COR Biosciences, USA) was used to detect primary mouse antibodies at a dilution of 1:1340 (5 nM). Polyclonal rabbit antibodies against *Xenopus laevis* nucleoporins Nup98, Nup93, Nup54 and Nup88 were prepared in the lab (Hülsmann et al., 2012). Polyclonal goat anti-rabbit IgG coupled to IRDye® 800CW (#925-32211; LI-COR Biosciences, USA) was used to detect primary rabbit antibodies at the lowest suggested dilution of 1:5,000. Anti-mouse IgG1 Fab single-domain antibody TP886 (5 nM), anti-mouse IgG1 Fc single-domain antibody TP1107 (5 nM) and anti-rabbit IgG single-domain antibody TP897 (10 nM) were labeled with a single IRDye® 800CW maleimide (#929-80020, LI-COR Biosciences, USA) via a C-terminal cysteine and used at the indicated concentrations in 4% (w/v) milk in 1×PBS. Polyclonal goat anti-mouse-HRP conjugate was from DakoCytomation (Denmark) and used at 1:1,000 dilution (5 nM). Anti-mouse IgG1 Fc single-domain antibody TP1107 was conjugated to maleimide-activated HRP (#31485, Thermo Fisher Scientific, USA) via a C-terminal cysteine by mixing both in equimolar amounts and incubation for 1 h at room temperature. The conjugate was used at 5 nM in 4% (w/v) milk in 1×PBS. The ECL solution was self-made and contained 5 mM Luminol (#A4685, Sigma-Aldrich, USA), 0.81 mM 4-lodophenylboronic acid (#471933, Sigma-Aldrich, USA) and 5 mM freshly added $H_2O_2$ in 0.1 M Tris/HCl PH 8.8.

1.8 Amplex™ UltraRed Assay

APEX2 was derived from pTRC-APEX2 (Addgene plasmid #72558), which was a gift from Alice Y. Ting (Lam et al., 2015). The anti-mouse IgG1 Fc single-domain antibody TP1107-APEX2 fusion was expressed from pTP1135 with an N-terminal $His_{14}$-bdNEDD8-tag in *E. coli* NEB express F' (New England Biolabs, USA) for 6 h at 25° C. in the presence of 1 mM of the heme precursor 5-aminolevulinic acid (#A3785, Sigma-Aldrich, USA). Following lysis, the protein was purified by nickel chelate affinity chromatography and eluted by cleavage with 500 nM bdNEDP1 protease (Frey and Görlich, 2014) in 100 mM potassium phosphate pH 7.5, 150 mM NaCl, 250 mM sucrose. The final assay mix contained 160 UM Amplex™ UltraRed, 160 PM $H_2O_2$ in either 100 mM Citrate pH 6.6, 150 mM NaCl (optimal pH for APEX2) or 100 mM potassium phosphate pH 6.0, 150 mM NaCl (optimal pH for HRP). 50 μl of this mix was used per reaction. Anti-mouse IgG1 Fc single-domain antibody TP1107-APEX2 was titrated from 167 nM to 470 fM in a 1.8-fold dilution series and 2 μl of each dilution added to 50 μl reaction mix in triplicates. HRP (#31490, Thermo Scientific, USA) was titrated from 31 nM to 5 fM in a 2.4-fold dilution series and 2 μl per dilution added to 50 μl reaction mix in triplicates. The 96-well plate containing these reactions was incubated at room temperature for 30 min and then resorufin fluorescence was measured at 590 nm (530 nm excitation) in a Bio-Tek Synergy HT Multi-Detection Microplate Reader (BioTek Instruments Inc., USA).

1.9 Immunofluorescence

Hela cells grown on glass coverslips were fixed for 10 min at room temperature with 3% (w/v) paraformaldehyde (PFA) and then washed two times with 1×PBS for 5 min each. Residual PFA was quenched by incubation with 50 mM NH₄Cl in 1×PBS for 5 min. After two washes with 1×PBS for 5 min each, the cells were permeabilized with 0.3% (v/v) Triton-X-100 for 3 min. Then the cells were washed three times quickly with 1×PBS and blocked for 30 min with 1% (w/v) BSA in 1×PBS (blocking buffer). Following blocking, the coverslips were stained with primary antibody, which was diluted in blocking buffer, in a humid chamber for 1 h at room temperature. The coverslips were then washed two times in 1×PBS for 15 min each and added again to a humid chamber for incubation with secondary antibody or anti-IgG single-domain antibody diluted in blocking buffer. Afterwards, the cells were washed two times in 1×PBS for 15 min each and the coverslips mounted with Slow Fade Gold (Thermo Fisher Scientific, USA) for imaging on a Leica TCS SP5 confocal microscope equipped with hybrid detectors (Leica, Germany). For methanol fixation, the cells were incubated with −20° C.-cooled methanol for 6 min at room temperature, washed two times in 1×PBS for 5 min each and then blocked in blocking buffer. The staining was performed as described above.

1.10 Antibodies for Immunofluorescence

The following rabbit antibodies were used for immunofluorescence on Hela cells: anti-Lap2 polyclonal antibody (1:100 dilution, #14651-1-AP, Proteintech, UK); anti-Ki-67 mAb clone D3B5 (1:200 dilution, #9129, Cell Signaling Technologies, USA). The following mouse mAbs were used for immunofluorescence on Hela cells: anti-Vimentin mAb clone V9 (1:10 dilution of Hybridoma supernatant, kind gift of Mary Osborn); anti-Ki-67 mAb clone B56 (1:50 dilution, #556003, BD Bioscience, USA); anti-TPR mAb 203-37 (1:500 dilution, Matritech Inc., USA; (Cordes et al., 1997)); anti-Cytochrome (Cyt) c mAb clone 6H2-B4 (1:50 dilution, #556432, BD Bioscience, USA); anti-Lamin A/C mAb clone 4C11 (1:50 dilution, #4777T, Cell Signaling Technologies, USA); anti-CD44 mAb clone 156-3C11 (1:200 dilution, #3570T, Cell Signaling Technologies, USA). Polyclonal goat anti-rabbit IgG (#111-545-003) and goat anti-mouse IgG (#115-545-003, Jackson ImmunoResearch, USA) coupled to Alexa Fluor® 488 (fluorescent dye) were used as secondary antibodies at 1:150 dilution ("33 nM). Anti-IgG single-domain antibodies were labeled with maleimide Alexa Fluor® dyes at engineered surface cysteines (Pleiner et al., 2015) and used at 20 nM. The used single-domain antibodies had the following degree of labeling: TP886-Alexa 488=1.9, TP1107-Alexa 488=2.7, TP1107-Alexa 647=2.2, TP1129-Alexa 488=2.5, TP1129-Alexa 568=2.0, TP1079-Alexa 488=2.2, TP897-Alexa 488=2.2.

2. Results 2.1 a Comprehensive Anti-IgG Single-Domain Antibody Toolbox

We immunized two alpacas separately with polyclonal mouse or rabbit IgG and used chemically biotinylated mouse monoclonal antibodies (mAbs) of defined subclasses as well as rabbit IgGs for phage display selections of single-domain antibodies from the resulting immune libraries. First results with the initially obtained anti-IgG single-domain antibodies were rather disappointing, i.e. we experienced dim and noisy signals in immunofluorescence as well as in Western blots. We reasoned that an increase in affinity and specificity might yield improved reagents and therefore re-immunized the animals after a one-year pause. For this, we used IgGs pre-bound to multivalent particulate antigens expected to provide strong T-helper cell epitopes. Moreover, we increased the stringency of the subsequent phage display selections by lowering the bait concentration down to the femtomolar range, which should not only select per se for sub-nanomolar binders, but also bring displayed single-domain antibodies in direct competition with each other, because the number of bait molecules was up to 1000-fold lower than the number of displaying phages. Finally, we performed in vitro affinity maturations by random mutagenesis and further rounds of phage display, this time also combined with off-rate selections. In this way, we obtained a large toolkit of anti-rabbit and anti-mouse IgG single-domain antibodies (FIG. 1a).

All single-domain antibodies were extensively characterized for subclass specificity, epitope location on Fab or Fc fragment and crossreactivity to IgGs from other species (Table 1, FIG. 1b, FIG. 1—figure supplement 1a). Their full protein sequences are listed in Table 2. Notably, we identified single-domain antibodies against all four mouse IgG subclasses and the sole rabbit IgG subclass. Strikingly, many anti-mouse IgG single-domain antibodies target IgG1, which represents the most abundant subclass of commercially available mouse mAbs (~62-64%), followed by IgG2a (~22-24%) and the less frequent IgG2b (~13%) and IgG3 (~1-2%). Since the vast majority (~99%) of mouse mAbs possess a kappa light chain, anti-kappa chain single-domain antibodies promised to be the most broadly useful tools and we therefore actively selected for such binders by swapping the IgG heavy chain subclass during sequential selection rounds. For the identification of binders targeting the rare lambda chain, we had to pre-deplete the single-domain antibody immune library of heavy chain and kappa chain-binders. Some of the identified single-domain antibodies have mixed specificities, e.g. multiple mouse Fab-binders target an interface between kappa light chain and IgG1 or IgG2a heavy chain. Most anti-mouse IgG single-domain antibodies are exclusively mouse-specific, while others additionally crossreact with rat IgG (FIG. 1—figure supplement 1a). The anti-rabbit IgG single-chain antibody TP897 also efficiently recognizes guinea pig IgG. All single-domain antibodies were produced by cytoplasmic expression in E. coli, mostly with an N-terminal His-NEDD8-tag for purification by Ni(II) chelate affinity capture and proteolytic release (Frey and Görlich, 2014). They were further equipped with ectopic cysteines for subsequent maleimide labeling reactions (Pleiner et al., 2015). Without further optimization, we typically obtained yields of 15 mg per liter of bacterial culture, which already suffices for a million immunofluorescence stains or 200 liters of Western blotting solution (see below).

We first assessed if the anti-IgG single-domain antibodies were specific and could purify their IgG target from its common source. Anti-rabbit IgG single-domain antibodies TP896 and TP897 isolated polyclonal rabbit IgG from crude rabbit serum with high specificity (FIG. 1—figure supplement 1b). Likewise, anti-mouse IgG single-domain antibodies TP881 and TP885 could purify an IgG1 mAb from hybridoma cell culture supernatant (FIG. 1—figure supplement 1c). Notably, Nanobody®-bound IgG was released under physiological conditions using SUMOStar protease cleavage (Pleiner et al., 2015). The main virtue of this approach is perhaps not to purify IgGs from sera, but to perform immune-affinity purifications of antigens or antigen complexes that have been pre-bound to the primary antibodies. In contrast to traditional IPs, this approach allows to release the purified complexes under fully native conditions.

2.2 Western Blotting with Horseradish Peroxidase-Conjugated Anti-IgG Single-Domain Antibodies We next tested the performance of anti-IgG single-domain antibodies as detection reagents in Western Blotting, which is a major application for secondary antibodies. A popular mode of signal detection in Western Blotting is enhanced chemiluminescence (ECL) in which antibody-horseradish peroxidase (HRP) conjugates are used. HRP is a heme-containing enzyme that catalyzes the oxidation of luminol in the presence of $H_2O_2$ to yield bright chemiluminescence, which is greatly increased by phenol-derived enhancers. We conjugated maleimide-activated HRP to anti-mouse IgG1 Fc single-chain antibody TP1107 via a C-terminal cysteine (FIG. 2—figure supplement 1a) and used the resulting conjugate in ECL Western Blotting. The Nanobody®-HRP conjugate is functional and outperformed a polyclonal secondary antibody-HRP conjugate from a commercial supplier (FIG. 2*a*). The anti-rabbit IgG single-chain antibody TP897 could also be linked to HRP and the resulting conjugate was functional and specific.

2.3 Comparison with Commercially Available Anti-IgG Single-Domain Antibodies

Commercially available anti-mouse IgG1 or anti-rabbit IgG single-domain antibodies designated as ab193651 and ab191866 (Abcam, United Kingdom) were compared with anti-mouse IgG1 single-chain antibody TP1107 and anti-rabbit IgG single-chain antibody TP897 as HRP conjugates (FIG. 2*b*). The single-domain antibodies of the invention provide a substantially higher sensitivity when used at equal concentrations.

2.4 Recombinant Ascorbate Peroxidase Fusion to Anti-IgG Single-Domain Antibodies Due to its stability and the breadth of its catalyzed colorimetric or chemiluminescent reactions that allow strong signal amplification, HRP is the most preferred enzyme for conjugation to secondary antibodies. However, it still has to be isolated from horseradish roots as a mixture of different isoforms, cannot be made in a practical scale and with a useful specific activity in *E. coli* (Krainer and Glieder, 2015), and it fails entirely as a genetic fusion to bacterially expressed single-domain antibodies. As an alternative, we tested the engineered APEX2 ascorbate peroxidase (Martell et al., 2012; Lam et al., 2015) as a fusion partner of the anti-mouse IgG1 Fc single-domain antibody TP1107. The TP1107-APEX2 fusion was not only well-expressed and soluble in *E. coli* (FIG. 2—figure supplement 1b), but also, it was active and efficiently catalyzed the oxidation of the initially colorless substrate Amplex™ UltraRed to the highly fluorescent resorufin (FIG. 2*b*). In line with previous reports (Lam et al., 2015), HRP seemed slightly more efficient than APEX2 in catalyzing this reaction. Nonetheless, low femtomole amounts of TP1107-APEX2 could be detected, suggesting its applicability e.g. in ELISA assays as well as for immunohistochemistry and enzymatic antigen-localization in immunoelectron microscopy applications.

Figure 3:
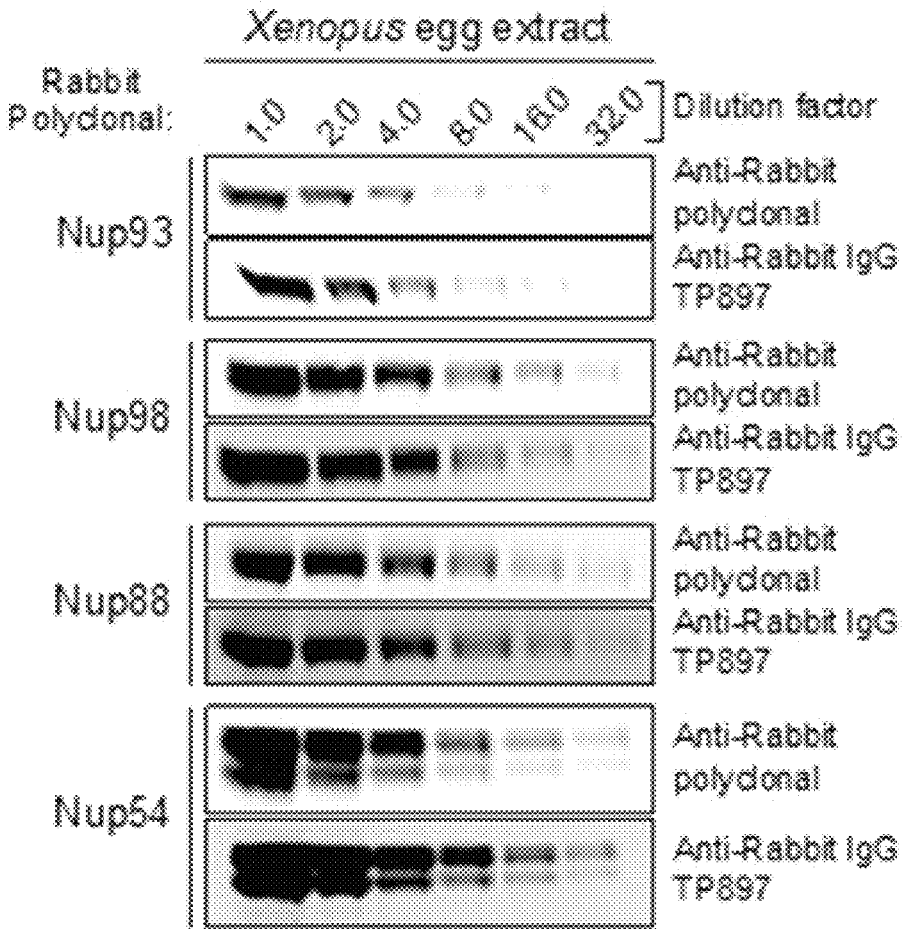
Figure 3:
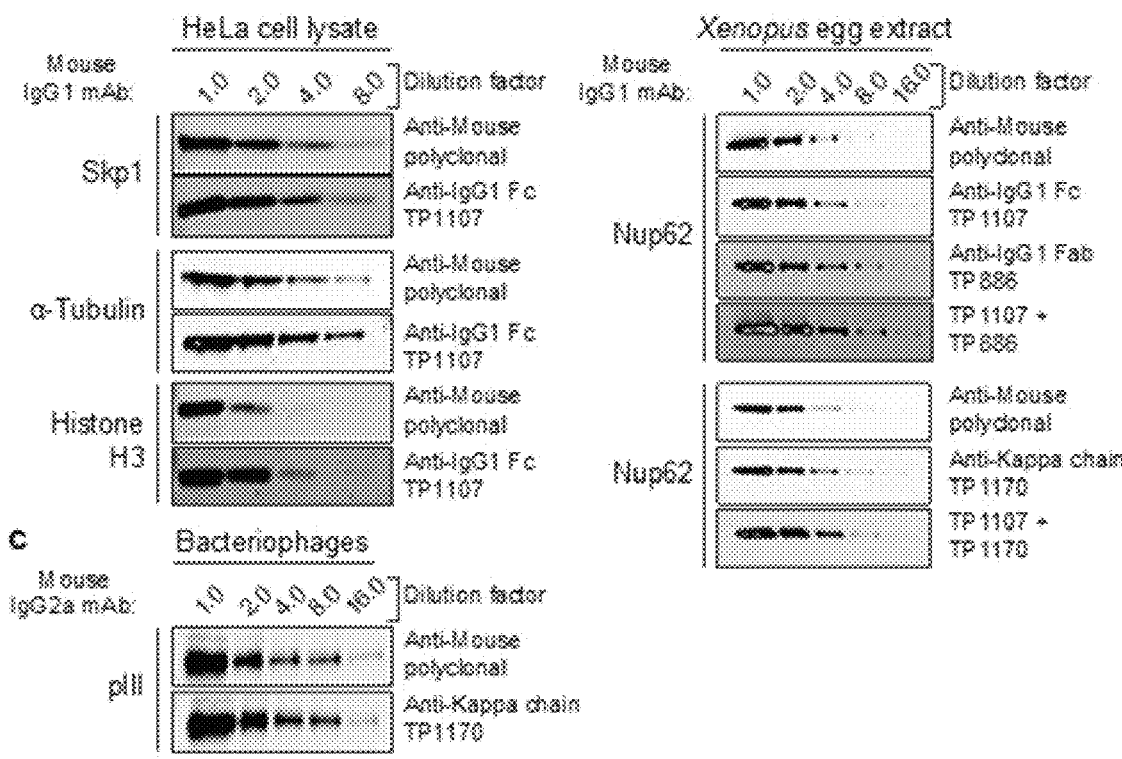

2.5 Western Blotting with Infrared Fluorophore-Linked Anti-IgG Single-Domain Antibodies A convenient alternative to peroxidase conjugation or fusion is the labeling of secondary antibodies with infrared fluorescent dyes. In fact, infrared fluorescent Western blotting has emerged as a superior alternative to classical ECL. It offers high signal-to-noise ratios, allows straightforward quantification due to signal linearity over many orders of magnitude and even enables the simultaneous dual color detection of multiple proteins. We thus labeled anti-IgG single-domain antibodies site-specifically with the infrared fluorophore IRDye® 800 at a C-terminal cysteine (Pleiner et al., 2015). The anti-rabbit IgG single-domain antibody TP897 alone performed just as well as a commercial polyclonal anti-rabbit IgG secondary antibody, when it was used with rabbit polyclonal antibodies to detect various nucleoporins (Nups) in a *Xenopus* egg extract (FIG. 3*a*). Similarly, the anti-mouse IgG1 Fc-specific single-domain antibody TP1107 gave comparable or even higher signal intensities than a polyclonal anti-mouse IgG secondary antibody in Western Blotting on HeLa cell lysate (FIG. 3*b*). Combinations of TP1107 with the compatible anti-mouse IgG1 Fab-specific single-domain antibody TP886 or the anti-mouse kappa chain Nanobody® TP1170 provided a clearly better detection sensitivity than the polyclonal secondary antibody. TP1170 allows sensitive detection of IgG2a subclass mAbs, as shown here for the detection of the bacteriophage minor coat protein pIII (FIG. 3*c*). We routinely found infrared fluorophore-labeled anti-IgG single-domain antibodies to yield higher detection sensitivity than their HRP-conjugated counterparts. When combined with the compatible IRDye® 680, dual color blots using e.g. mouse and rabbit primary antibodies are easily possible (not shown). In contrast to polyclonal secondary antibodies, IRDye®-labeled anti-IgG single-domain antibodies give also a clean and strong signal when pre-bound to primary antibodies before application. This makes a separate incubation with the secondary antibody dispensable and saves up to 2 h processing time per blot. We explored such a one-step staining strategy in more detail below for immunofluorescence.

2.6 Single and Multi-Color Imaging with Anti-IgG Single-Domain Antibodies

We next sought to assess the performance of the anti-IgG single-domain antibodies as detection reagents in conventional indirect immunofluorescence. For this, cells are incubated sequentially with primary and secondary antibodies with intervening washing steps. Fluorophore-linked polyclonal secondary antibodies are routinely used for detection, since they can bind primary antibodies at multiple sites and thus deliver many fluorophores to enable large signal amplification. In contrast, individual anti-IgG single-domain antibodies target only a single epitope per antibody (or two for symmetrical binding sites) and we therefore expected only modest signal amplification. Strikingly however, the anti-IgG1 single-domain antibodies TP886 and TP1107, which specifically target IgG1 Fab and Fc fragment, respectively, not only performed well in Western Blotting, but also were well-behaved imaging reagents. For maximum brightness, we labeled these single-domain antibodies with 2-3 fluorophores each at defined cysteines (Pleiner et al., 2015) and used them individually for the detection of mouse IgG1 mAbs in an indirect Hela cell immunostaining (FIG. 4*a*). Surprisingly, both were only slightly dimmer than the polyclonal mixture of anti-mouse secondary antibodies. We assume that the excellent single-domain antibody signal is also due to less steric hindrance as compared to the much larger conventional secondary antibody. When both single-domain antibodies were used in combination, we detected increased signal strengths that often were directly comparable to those obtained with the secondary antibody (e.g. for Vimentin or Ki-67) (see also FIG. 4—figure supplement 1a). Importantly, despite a high labeling density with (the always somewhat sticky) fluorophores, we observed no detectable background staining with these anti-IgG single-domain antibodies. This probably relates to the fact that the affinity of our single-domain antibodies is very high, which allows their use at rather low nanomolar concentrations. The poor performance of the first anti-IgG single-domain antibody generation indeed suggests that such excellent signal to noise ratio is not a trivial feature for a monovalent detection reagent.

For the detection of IgG2a subclass mAbs, we used a combination of two single-domain antibodies, TP1129 and TP1170 (FIG. 4b, FIG. 4—figure supplement 1b). The IgG2a-specific single-domain antibody TP1129 targets an epitope on the Fc-fragment and was obtained after affinity maturation of a lower affinity precursor (FIG. 4—figure supplement 1c). Likewise, the kappa chain-specific Nanobody® TP1170 is an affinity-optimized variant, obtained after error-prone PCR, DNA shuffling and affinity selection (FIG. 4—figure supplement 1d). TP1170 also proved effective in combination with the anti-IgG1 Fc single-domain antibody TP1107 for the detection of IgG1 kappa mAbs (FIG. 4—figure supplement 1e and 1f). The anti-rabbit IgG Fc single-domain antibody TP897 can be used for the detection of polyclonal and monoclonal rabbit IgG (FIG. 4c).

The presented single-domain antibodies are specific for their respective IgG subclass, as shown in the specificity profiling dot blot assay (FIG. 1b). We exploited this for multicolor imaging of Hela cells with different IgG subclasses (FIG. 4d). Mouse IgG1, mouse IgG2a and rabbit IgG-specific single-domain antibodies did not show any cross-reaction and consequently allowed for clean co-localization experiments. Even triple co-localizations were readily possible.

2.7 Rapid One-Step Immunostaining and Co-Localization

Figure 5:
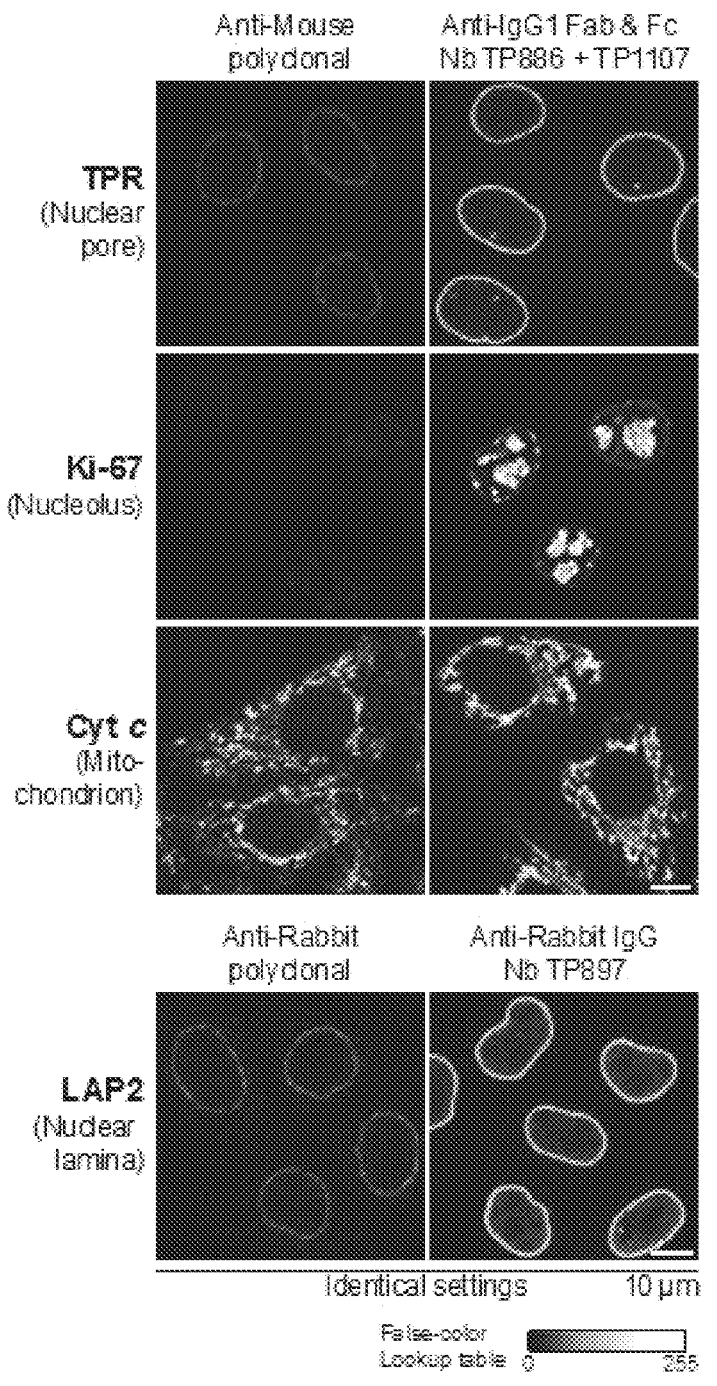
Figure 5:
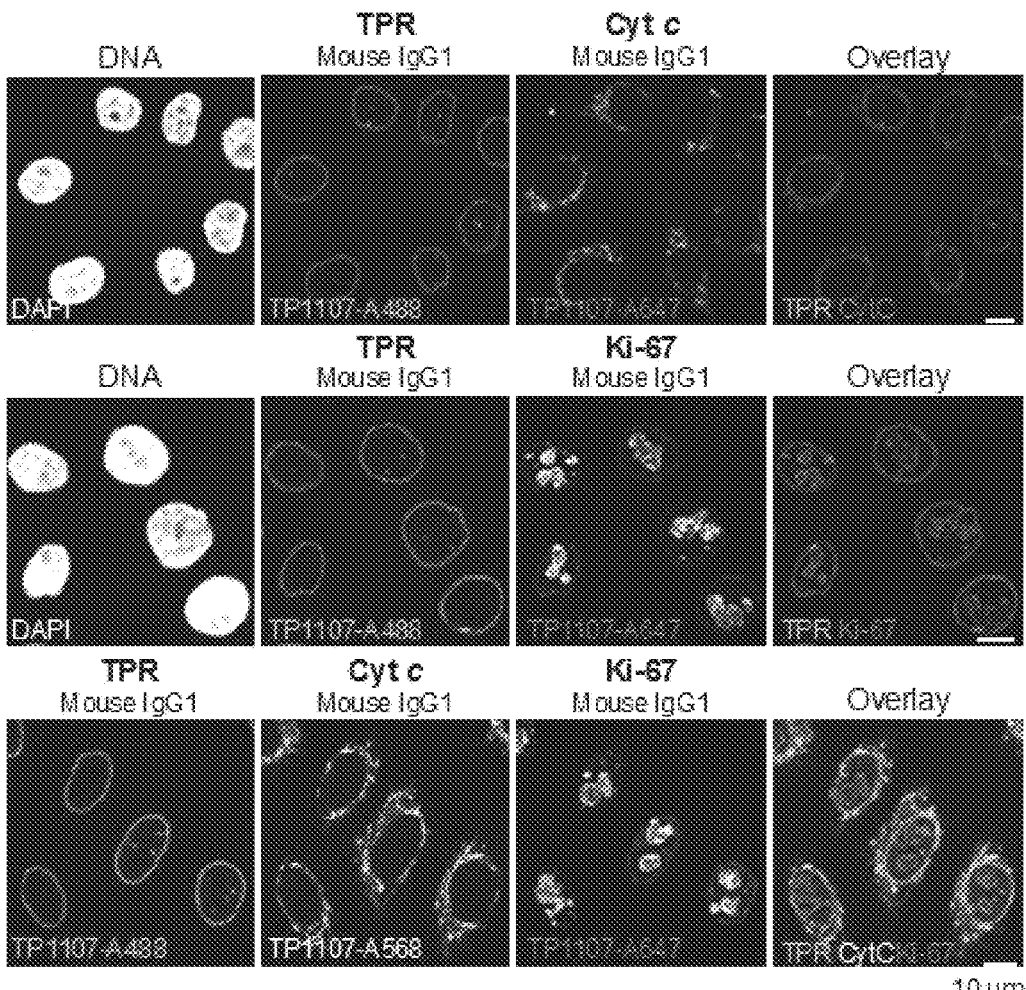

The main reasons for separate incubation steps of primary and secondary IgGs in indirect immunofluorescence and Western blotting are the large size, as well as the bivalent and polyclonal nature of conventional secondary antibodies. If primary and secondary antibodies are pre-incubated, large oligomeric complexes form, which in immunofluorescence cannot easily penetrate into cells to reach their target and thus create background and poor signal (see FIG. 5a). In contrast, anti-IgG single-domain antibodies are monovalent and therefore do not crosslink primary antibodies. This allows streamlining the conventional immunostaining procedure to a single step. The primary antibodies are simply pre-incubated with fluorescently labeled anti-IgG single-domain antibodies and then applied to cells together. After washing, the cells can be directly mounted for imaging. In such a workflow, anti-IgG single-domain antibodies perform exceptionally well (FIG. 5a). This time-saving protocol is also suitable for co-localization studies combining mouse and rabbit IgGs or combining mouse mAbs of different sub-classes.

If the off-rate of the IgG pre-bound single-domain antibodies were negligible over the staining period, then an exchange between the different pre-formed complexes would also be negligible. This would also make it unnecessary to use different IgG subclasses for multicolor imaging. We thus tested a multicolor staining workflow of Hela cells relying solely on IgG1 subclass mAbs (FIG. 5b). For this, we labeled anti-IgG1 Fc single-domain antibody TP1107 with either Alexa 488, Alexa 568 or Alexa 647 maleimide and pre-incubated it with different IgG1 mAbs. The separately pre-incubated mixes were then combined and applied to Hela cells for staining in one-step. Strikingly, we obtained clean dual and even triple co-localizations. In order to preclude an intermixing of colors, unlabeled TP1107 can be added in excess to the final mix and cells can be post-fixed after staining and washing.

3. Discussion

Due to the absence of more sustainable alternatives in the past, the great usefulness of polyclonal secondary antibodies in basic research certainly justified their animal-based production. However, in order to guarantee their constant supply to an ever-growing market, the producing companies had to dramatically increase their livestock, aim for very high antibody titres using aggressive hyper-immunization strategies causing strong side effects and increase the frequency and volume of collected bleedings. It is therefore not surprising that the global industrial scale production of antibodies causes severe animal welfare and ethical problems. The magnitude of these problems recently surfaced in the Santa Cruz Biotechnology scandal (Shen, 2013; Reardon, 2016).

Ideally, one should replace all animal immunization by selecting binders from synthetic libraries (Gray et al., 2016; Moutel et al., 2016; McMahon et al., 2017; Zimmermann et al., 2017). Yet, with a purely synthetic approach it is still not straightforward to obtain high-affinity binders. Further, the synthetic strategy is typically also inferior in terms of binder-specificity, because it lacks the stringent selection against self-reactivity that happens in antigen-exposed animals. The requirement for specificity is particularly high for secondary antibodies. We therefore see the here applied approach of using an immune library for binder selection as the best possible compromise. Since it is generally sufficient to obtain a few good single-domain antibodies out of a small blood sample containing ~100 million lymphocytes, and since we found ways of further improving the initially found ones in vitro, there was no need for any hyper-immunization aiming at high titers. Importantly, once ideal single-domain antibodies are identified, they are defined by their sequence and they can be renewably produced in E. coli at constant quality and without any further animal involvement. Since polyclonal secondary antibody production accounts for the largest share of immunized animals in the world, the anti-IgG single-domain antibodies described in this study have the potential to make a great step forward towards reducing animal use and further contribute to a future of standardized recombinant antibodies (Marx, 2013; Bradbury and Pluckthun, 2015a; Bradbury and Plückthun, 2015b).

We expect that our anti-IgG single-domain antibodies will replace polyclonal secondary antibodies in many of their applications, e.g. in Western blotting and immunofluorescence. For both applications, their site-specific and quantitative modification with fluorophores via maleimide chemistry creates superior reagents with predictable label density and position. Furthermore, the precise targeting of primary mouse antibodies at the kappa chain with a specific Nanobody® could substantially reduce the label displacement in super-resolution microscopy. In the future, we will also explore the direct coupling of anti-IgG single-domain antibodies with engineered cysteines onto colloidal gold particles for electron microscopy, which also suffers from the large linkage error introduced by bulky secondary antibodies.

Due to their monovalent and monoclonal nature, anti-IgG single-domain antibodies do not crosslink primary antibodies and we exploited this for a one-step immunostaining workflow that saves valuable hands-on time and can also be extended to Western blotting. We envision that for routine stainings, preformed complexes of primary antibodies and labeled single-domain antibodies can be prepared as stock solutions or simply bought from commercial suppliers. Due to the high affinity of the described single-domain antibodies, the same strategy also enables multicolor immunostainings based on a single IgG subclass, which could also be relevant for flow cytometry sorting of specific cell types. This would be a cheaper and more flexible alternative to differentially labeled primary antibodies, it does not pose the risk of inactivating an antigen-binding site and it can easily be done if only small amounts of primary antibody are available.

Further, since the DNA sequences of these anti-IgG single-domain antibodies are essentially synthetic building blocks, they can be genetically appended to the multitude of available tags, fluorescent proteins or enzymes to generate fusion proteins with novel functions for tailored applications in basic research and medical diagnostics, and also become valuable tools for immunology to study Fc or B cell receptors and downstream signaling cascades. Furthermore, anti-IgG single-domain antibodies equipped with protease-cleavable affinity tags (Pleiner et al., 2015) will allow the native isolation of any antibody-target complex e.g. for structural studies by cryo-EM or functional assays. Even though the here presented anti-IgG single-domain antibody toolbox is already highly optimized, we will continue to extend it by identifying new single-domain antibodies that decorate complementary binding sites and thus allow a further signal enhancement, and combine them with additional functional elements. In any case, it will be an open resource for all interested labs.

REFERENCES

Arbabi Ghahroudi, M., Desmyter, A., Wyns, L., Hamers, R. & Muyldermans, S. (1997) Selection and identification of single domain antibody fragments from camel heavy-chain antibodies. *FEBS Lett,* 414, 521-526.

Balzarotti, F., Eilers, Y., Gwosch, K. C., Gynnå, A. H., Westphal, V., Stefani, F. D., Elf, J. & Hell, S. W. (2017) Nanometer resolution imaging and tracking of fluorescent molecules with minimal photon fluxes. *Science,* 355, 606-612.

Bates, M., Dempsey, G. T., Chen, K. H. & Zhuang, X. (2012) Multicolor super-resolution fluorescence imaging via multi-parameter fluorophore detection. *Chemphyschem,* 13, 99-107.

Bates, M., Huang, B., Dempsey, G. T. & Zhuang, X. (2007) Multicolor super-resolution imaging with photo-switchable fluorescent probes. *Science,* 317, 1749-1753.

Bradbury, A. & Plückthun, A. (2015a) Reproducibility: Standardize antibodies used in research. *Nature,* 518, 27-29.

Bradbury, A. R. & Pluckthun, A. (2015b) Getting to reproducible antibodies: the rationale for sequenced recombinant characterized reagents. *Protein Eng Des Sel,* 28, 303-305.

Cordes, V. C., Reidenbach, S. & Franke, W. W. (1995) High content of a nuclear pore complex protein in cytoplasmic annulate lamellae of *Xenopus* oocytes. *Eur J Cell Biol,* 68, 240-255.

Cordes, V. C., Reidenbach, S., Rackwitz, H. R. & Franke, W. W. (1997) Identification of protein p270/Tpr as a constitutive component of the nuclear pore complex-attached intranuclear filaments. *J Cell Biol,* 136, 515-529.

Desmyter, A., Spinelli, S., Roussel, A. & Cambillau, C. (2015) Camelid nanobodies: killing two birds with one stone. *Curr Opin Struct Biol,* 32C, 1-8.

Frey, S. & Görlich, D. (2014) A new set of highly efficient, tag-cleaving proteases for purifying recombinant proteins. *J Chromatogr A,* 1337, 95-105.

Göttfert, F., Pleiner, T., Heine, J., Westphal, V., Görlich, D., Sahl, S. J. & Hell, S. W. (2017) Strong signal increase in STED fluorescence microscopy by imaging regions of subdiffraction extent. *Proc Natl Acad Sci USA,* 114, 2125-2130.

Gray, A. C., Sidhu, S. S., Chandrasekera, P. C., Hendriksen, C. F. & Borrebaeck, C. A. (2016) Animal-Friendly Affinity Reagents: Replacing the Needless in the Haystack. *Trends Biotechnol,* 34, 960-969.

Hamers-Casterman, C., Atarhouch, T., Muyldermans, S., Robinson, G., Hamers, C., Songa, E. B., Bendahman, N. & Hamers, R. (1993) Naturally occurring antibodies devoid of light chains. *Nature,* 363, 446-448.

Helma, J., Cardoso, M. C., Muyldermans, S. & Leonhardt, H. (2015) Nanobodies and recombinant binders in cell biology. *J Cell Biol,* 209, 633-644.

Huang, B., Babcock, H. & Zhuang, X. (2010) Breaking the diffraction barrier: super-resolution imaging of cells. *Cell,* 143, 1047-1058.

Huang, F., Sirinakis, G., Allgeyer, E. S., Schroeder, L. K., Duim, W. C., Kromann, E. B., Phan, T., Rivera-Molina, F. E., Myers, J. R., Irnov, I., Lessard, M., Zhang, Y., Handel, M. A., Jacobs-Wagner, C., Lusk, C. P., Rothman, J. E., Toomre, D., Booth, M. J. & Bewersdorf, J. (2016) Ultra-High Resolution 3D Imaging of Whole Cells. *Cell,* 166, 1028-1040.

Hülsmann, B. B., Labokha, A. A. & Görlich, D. (2012) The permeability of reconstituted nuclear pores provides direct evidence for the selective phase model. *Cell,* 150, 738-751.

Kijanka, M., Dorresteijn, B., Oliveira, S. & van Bergen en Henegouwen, P. M. (2015) Nanobody-based cancer therapy of solid tumors. *Nanomedicine (Lond),* 10, 161-174.

Krainer, F. W. & Glieder, A. (2015) An updated view on horseradish peroxidases: recombinant production and biotechnological applications. *Appl Microbiol Biotechnol,* 99, 1611-1625.

Lam, S. S., Martell, J. D., Kamer, K. J., Deerinck, T. J., Ellisman, M. H., Mootha, V. K. & Ting, A. Y. (2015) Directed evolution of APEX2 for electron microscopy and proximity labeling. *Nat Methods,* 12, 51-54.

Liu, L., Spurrier, J., Butt, T. R. & Strickler, J. E. (2008) Enhanced protein expression in the baculovirus/insect cell system using engineered SUMO fusions. *Protein Expr Purif,* 62, 21-28.

Martell, J. D., Deerinck, T. J., Sancak, Y., Poulos, T. L., Mootha, V. K., Sosinsky, G. E., Ellisman, M. H. & Ting, A. Y. (2012) Engineered ascorbate peroxidase as a genetically encoded reporter for electron microscopy. *Nat Biotechnol,* 30, 1143-1148.

Marx, V. (2013) Calling the next generation of affinity reagents. *Nat Methods,* 10, 829-833.

McMahon, C., Baier, A. S., Zheng, S., Pascolutti, R., Ong, J. X., Erlandson, S. C., Hilger, D., Ring, A. M., Manglik, A. & Kruse, A. C. (2017) Platform for rapid nanobody discovery in vitro. *bioRxiv,* doi: https://doi.org/10.1101/151043.

Moutel, S., Bery, N., Bernard, V., Keller, L., Lemesre, E., de Marco, A., Ligat, L., Rain, J. C., Favre, G., Olichon, A. & Perez, F. (2016) NaLi-H1: A universal synthetic library of humanized nanobodies providing highly functional antibodies and intrabodies. *Elife,* 5, Muyldermans, S. (2013) Nanobodies: natural single-domain antibodies. *Annu Rev Biochem,* 82, 775-797.

Pleiner, T., Bates, M., Trakhanov, S., Lee, C. T., Schliep, J. E., Chug, H., Böhning, M., Stark, H., Urlaub, H. &

Görlich, D. (2015) Nanobodies: site-specific labeling for super-resolution imaging, rapid epitope-mapping and native protein complex isolation. *Elife*, 4, e11349.

Reardon, S. (2016) US government issues historic $3.5-million fine over animal welfare. *Nature*, doi: 10.1038/nature.2016.19958.

Ries, J., Kaplan, C., Platonova, E., Eghlidi, H. & Ewers, H. (2012) A simple, versatile method for GFP-based super-resolution microscopy via nanobodies. *Nat Methods, 9,* 582-584.

Rust, M. J., Bates, M. & Zhuang, X. (2006) Sub-diffraction-limit imaging by stochastic optical reconstruction microscopy (STORM). *Nat Methods, 3,* 793-795.

Sahl, S. J., Hell, S. W. & Jakobs, S. (2017) Fluorescence nanoscopy in cell biology. *Nat Rev Mol Cell Biol,*

Shen, H. (2013) Discovery of goat facility adds to antibody provider's woes. *Nature,* doi: 10.1038/nature.2013.12203.

Szymborska, A., de Marco, A., Daigle, N., Cordes, V. C., Briggs, J. A. & Ellenberg, J. (2013) Nuclear pore scaffold structure analyzed by super-resolution microscopy and particle averaging. *Science,* 341, 655-658.

Traenkle, B. & Rothbauer, U. (2017) Under the Microscope: Single-Domain Antibodies for Live-Cell Imaging and Super-Resolution Microscopy. *Front Immunol,* 8, 1030.

Van Bockstaele, F., Holz, J. B. & Revets, H. (2009) The development of nanobodies for therapeutic applications. *Curr Opin Investig Drugs,* 10, 1212-1224.

Weber, K., Rathke, P. C. & Osborn, M. (1978) Cytoplasmic microtubular images in glutaraldehyde-fixed tissue culture cells by electron microscopy and by immunofluorescence microscopy. *Proc Natl Acad Sci USA,* 75, 1820-1824.

Xu, K., Babcock, H. P. & Zhuang, X. (2012) Dual-objective STORM reveals three-dimensional filament organization in the actin cytoskeleton. *Nat Methods,* 9, 185-188.

Zimmermann, I., Egloff, P., Hutter, C., Stohler, P., Bocquet, N., Hug, M., Siegrist, M., Svacha, L., Gera, J. & Gmuer, S. (2017) Synthetic single domain antibodies for the conformational trapping of membrane proteins. *bioRxiv,* doi: https://doi.org/10.1101/168559.

SEQUENCE LISTING

As filed Jul. 17, 2025, and as accepted without errors in communication from the Patent Office Aug. 14, 2025.

The invention claimed is:

1. A combination comprising a plurality of different single domain antibodies or a plurality of different immune complexes comprising a single domain antibody bound to an IgG antibody, wherein the single domain antibodies are selected from a combination of several single domain antibodies recognizing the same type of IgG molecules, which bind to non-overlapping epitopes on said IgG molecules, wherein the single domain antibodies are selected from:
(i) single domain antibodies directed against rabbit IgG of SEQ ID NOs. 1 or 2; or
(ii) single domain antibodies directed against mouse IgG of SEQ ID NOs. 3-34.

2. The combination according to claim 1, wherein the single domain antibodies are selected from a combination of
(i) single domain antibodies of SEQ ID NO. 5 and SEQ ID NO. 8,
(ii) single domain antibodies of SEQ ID NO. 8 and SEQ ID NO. 19,
(iii) single domain antibodies of SEQ ID NO. 18 and SEQ ID NO. 19,
(iv) single domain antibodies of SEQ ID NO. 5 and SEQ ID NO. 18,
(v) single domain antibodies of SEQ ID NO. 5 and SEQ ID NO. 25, or
(vi) single domain antibodies comprising the sequences as shown in SEQ ID NO. 1 and SEQ ID NO. 2.

3. The combination according to claim 1, wherein the single domain antibodies are selected from a combination of 2 or 3 single domain antibodies.

4. The combination according to claim 1, wherein the same type of IgG molecules are selected from the group consisting of mouse IgG1, mouse IgG2a and rabbit IgG.

5. The combination according to claim 1, wherein said non-overlapping epitopes on said IgG molecules are epitopes on different regions on said IgG molecules.

6. The combination according to claim 5, wherein said different regions on said IgG molecules are selected from the group consisting of a light chain, a κ and/or λ light chain, and a Fc or hinge fragment of said IgG molecules.

7. The combination according to claim 5, wherein said epitopes are on the light chain of said IgG molecules.

8. The combination according to claim 5, wherein said epitopes are on the κ and/or λ light chain of said IgG molecules.

9. The combination according to claim 5, wherein said epitopes are on the Fc or hinge fragment of said IgG molecules.

10. A combination comprising a plurality of different single domain antibodies or a plurality of different immune complexes comprising a single domain antibody bound to an IgG antibody, wherein the single domain antibodies are selected from a combination of several single domain antibodies recognizing the same type of IgG molecules, which bind to non-overlapping epitopes on said IgG molecules, wherein at least one single domain antibody of said combination
(i) is directed against rabbit IgG of SEQ ID NOs. 1 or 2; or
(ii) is directed against mouse IgG of SEQ ID NOs. 3-34.

11. A combination comprising a plurality of different single domain antibodies comprising a single domain antibody bound to an IgG antibody, wherein the single domain antibodies are selected from a combination of several single domain antibodies recognizing the same type of IgG molecules, which bind to non-overlapping epitopes on said IgG molecules, wherein the single domain antibodies are selected from a combination of:

(i) the single domain antibodies comprising amino acid sequences of SEQ ID NO. 5 and SEQ ID NO. 8;

(ii) the single domain antibodies comprising the amino acid sequence of SEQ ID NO. 8 and SEQ ID NO. 19;

(iii) the single domain antibodies comprising the amino acid sequences of SEQ ID NO. 18 and SEQ ID NO. 19;

(iv) the single domain antibodies comprising the amino acid sequences of SEQ ID NO. 5 and SEQ ID NO. 18;

(v) the single domain antibodies comprising the amino acid sequences of SEQ ID NO. 5 and SEQ ID NO. 25; or (vi) the single domain antibodies comprising the amino acid sequences of SEQ ID NO:1 and SEQ ID NO:2.

\* \* \* \* \*

SEQUENCE LISTING

```
<160> NUMBER OF SEQ ID NOS: 271

<210> SEQ ID NO 1
<211> LENGTH: 130
<212> TYPE: PRT
<213> ORGANISM: Artificial Sequence
<220> FEATURE:
<223> OTHER INFORMATION: Nb_1_TP896

<400> SEQUENCE: 1

Gln Val Gln Leu Val Glu Ser Gly Gly Gly Leu Ala Gln Pro Gly Gly
1               5                   10                  15

Ser Leu Arg Leu Ser Cys Ala Val Ser Gly Phe Arg Phe Ser Phe Tyr
            20                  25                  30

Gln Met Thr Trp Val Arg Gln Ala Pro Gly Lys Gly Leu Glu Trp Val
        35                  40                  45

Ala Asp Ile Asn Ser Ala Gly Gly Thr Thr Tyr Tyr Ala Asp Ser Val
    50                  55                  60

Lys Gly Arg Phe Ala Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Gly Lys Phe Pro Val Glu Ser Arg Arg His Gly Gly Thr Ala
            100                 105                 110

Gln Trp Asp Glu Tyr Asp Tyr Trp Gly Gln Gly Thr Arg Val Thr Val
            115                 120                 125

Ser Ser
    130

<210> SEQ ID NO 2
<211> LENGTH: 116
<212> TYPE: PRT
<213> ORGANISM: Artificial Sequence
<220> FEATURE:
<223> OTHER INFORMATION: Nb_2_TP897

<400> SEQUENCE: 2
```

-continued

```
Gln Val Gln Leu Val Glu Ser Gly Gly Gly Leu Val Gln Ala Gly Asp
1               5                   10                  15

Ser Leu Arg Leu Ser Cys Val Ala Ser Gly Arg Ser Leu Asp Gly Ala
            20                  25                  30

Thr Met Arg Trp Tyr Arg Gln Ala Pro Gly Lys Glu Arg Glu Phe Val
        35                  40                  45

Ala Gly Ile Phe Trp Asp Glu Ile Gly Thr Glu Tyr Ala Asp Thr Ala
    50                  55                  60

Lys Gly Arg Phe Thr Ile Ser Arg Asp Asn Ala Lys Asn Thr Ile Tyr
65                  70                  75                  80

Leu Gln Met Thr Asn Leu Arg Ser Glu Asp Thr Ala Met Tyr Tyr Cys
                85                  90                  95

Asn Gly Leu Val Phe Gly Gly Glu Tyr Trp Gly Gln Gly Thr Gln Val
            100                 105                 110

Thr Val Ser Ser
        115
```

```
<210> SEQ ID NO 3
<211> LENGTH: 126
<212> TYPE: PRT
<213> ORGANISM: Artificial Sequence
<220> FEATURE:
<223> OTHER INFORMATION: Nb_3_TP974

<400> SEQUENCE: 3
```

```
Gln Val Gln Leu Val Glu Ser Gly Gly Gly Trp Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Ala Ile Asp Thr Gly Gly Gly Tyr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Ser Pro Glu Asp Thr Ala Leu Tyr Tyr Cys
                85                  90                  95

Ala Thr Thr Tyr Ser Gly Asn Tyr Tyr Ser Asp Tyr Thr Ile Gly Asn
            100                 105                 110

Ser Asp Tyr Arg Gly Gln Gly Thr Leu Val Thr Val Ser Ser
        115                 120                 125
```

```
<210> SEQ ID NO 4
<211> LENGTH: 126
<212> TYPE: PRT
<213> ORGANISM: Artificial Sequence
<220> FEATURE:
<223> OTHER INFORMATION: Nb_4_TP1079

<400> SEQUENCE: 4
```

```
Gln Val Gln Leu Val Glu Ser Gly Gly Gly Leu Val Leu Pro Gly Gly
1               5                   10                  15

Ser Leu Arg Leu Ser Cys Val Ala Ser Gly Phe Thr Phe Ser Asp Thr
            20                  25                  30

Ala Met Met Trp Val Arg Gln Ala Pro Gly Lys Gly Arg Glu Trp Val
        35                  40                  45

Ala Ala Ile Asp Thr Gly Gly Ser Thr Tyr Tyr Ala Asp Ser Val
    50                  55                  60
```

-continued

```
Gln Gly Arg Phe Thr Ile Ser Arg Asp Ser Ala Lys Asn Thr Leu Tyr
65                  70                  75                  80

Leu Gln Met Asn Ser Leu Lys Pro Glu Asp Thr Ala Arg Tyr Tyr Cys
                85                  90                  95

Ala Lys Thr Tyr Ser Gly Asn Tyr Tyr Ser Asn Tyr Thr Val Ala Asn
                100                 105                 110

Tyr Gly Thr Thr Gly Arg Gly Thr Leu Val Thr Val Ser Ser
            115                 120                 125

<210> SEQ ID NO 5
<211> LENGTH: 126
<212> TYPE: PRT
<213> ORGANISM: Artificial Sequence
<220> FEATURE:
<223> OTHER INFORMATION: Nb_5_TP1170

<400> SEQUENCE: 5

Gln Val Gln Leu Val Glu Ser Gly Gly Gly Trp Val Gln Pro Gly Gly
1               5                   10                  15

Ser Leu Arg Leu Ser Cys Ala Ala Ser Gly Phe Thr Phe Ser Asp Thr
                20                  25                  30

Ala Met Met Trp Val Arg Gln Ala Pro Gly Lys Gly Arg Glu Trp Val
            35                  40                  45

Ala Ala Ile Asp Thr Gly Gly Gly Tyr Thr Tyr Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Arg Tyr Tyr Cys
                85                  90                  95

Ala Lys Thr Tyr Ser Gly Asn Tyr Tyr Ser Asn Tyr Thr Val Ala Asn
                100                 105                 110

Tyr Gly Thr Thr Gly Arg Gly Thr Leu Val Thr Val Ser Ser
            115                 120                 125

<210> SEQ ID NO 6
<211> LENGTH: 129
<212> TYPE: PRT
<213> ORGANISM: Artificial Sequence
<220> FEATURE:
<223> OTHER INFORMATION: Nb_6_TP975

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Asp Met Ser Trp Val Arg Gln Ala Pro Gly Lys Gly Leu Glu Trp Val
            35                  40                  45

Ser Ala Ile Ser Ser Gly Gly Gly Ser Thr Tyr Tyr Val Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Gly Ser Gly Pro Ala Phe Arg Leu Ser Gly Gly Ser Trp Ser
                100                 105                 110

Pro Arg Gly Asp Gly Ser Arg Gly Gln Gly Thr Leu Val Thr Val Ser
```

```
              115                 120                 125

Ser

<210> SEQ ID NO 7
<211> LENGTH: 126
<212> TYPE: PRT
<213> ORGANISM: Artificial Sequence
<220> FEATURE:
<223> OTHER INFORMATION: Nb_7_TP1014

<400> SEQUENCE: 7

Gln Val Gln Leu Val Glu Ser Gly Gly Gly Glu Val Gln Ala Gly Gly
1               5                   10                  15

Ser Leu Arg Leu Ser Cys Ala Ala Ser Gly Arg Thr Phe Ser Arg Asn
            20                  25                  30

Val Met Gly Trp Phe Arg Gln Ala Pro Gly Lys Glu Arg Glu Phe Leu
            35                  40                  45

Ala Ala Ile Asn Trp Ser Gly Asn Ser Ile Gly Tyr Arg Asp Ser Val
    50                  55                  60

Lys Gly Arg Phe Thr Ala Ser Arg Asp Asn Val Asn Asn Thr Leu Tyr
65                  70                  75                  80

Leu Arg Met Asn Asn Leu Lys Pro Glu Asp Thr Ala Val Tyr Tyr Cys
                85                  90                  95

Ala Ala Arg Gly Ser Ser Asp Tyr Asp Val Ala Met Gln Gly His Glu
            100                 105                 110

Tyr Thr Tyr Trp Gly Gln Gly Thr Gln Val Thr Val Ser Ser
        115                 120                 125

<210> SEQ ID NO 8
<211> LENGTH: 120
<212> TYPE: PRT
<213> ORGANISM: Artificial Sequence
<220> FEATURE:
<223> OTHER INFORMATION: Nb_8_TP1107

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Thr
            20                  25                  30

Trp Met Asn Trp Val Arg Gln Ala Pro Gly Lys Gly Leu Tyr Trp Ile
            35                  40                  45

Ser Ala Ile Asn Pro Asp Gly Gly Asn Thr Ala Tyr Ala Asp Ser Val
    50                  55                  60

Lys Gly Arg Phe Thr Ile Ser Arg Asp Asn Ala Lys Asn Met Val Tyr
65                  70                  75                  80

Leu Gln Met Asp Asn Leu Arg Pro Glu Asp Thr Ala Met Tyr Tyr Cys
                85                  90                  95

Ala Lys Gly Trp Val Arg Leu Pro Asp Pro Asp Leu Val Arg Gly Gln
            100                 105                 110

Gly Thr Gln Val Thr Val Ser Ser
        115                 120

<210> SEQ ID NO 9
<211> LENGTH: 125
<212> TYPE: PRT
<213> ORGANISM: Artificial Sequence
<220> FEATURE:
<223> OTHER INFORMATION: Nb_9_TP878
```

-continued

<400> SEQUENCE: 9

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Ala Trp Tyr Arg His Arg Pro Gly Met Gln Arg Glu Arg Val
        35                  40                  45

Ala Ala Ile Ser Ser Gly Gly Thr Thr Ser Tyr Ala Asp Ser Val Lys
    50                  55                  60

Gly Arg Phe Thr Ile Ser Arg Asp Asn Ala Arg Asp Thr Leu Tyr Leu
65                  70                  75                  80

Gln Met Asn Ser Leu Lys Pro Glu Asp Thr Ala Met Tyr Tyr Cys Ala
            85                  90                  95

Ala Cys Pro Gly Asp Tyr Thr Ser Thr Ile Cys Asn Ser Asp Gly Met
            100                 105                 110

Asp Tyr Trp Gly Lys Gly Thr Leu Val Thr Val Ser Ser
        115                 120                 125
```

<210> SEQ ID NO 10
<211> LENGTH: 125
<212> TYPE: PRT
<213> ORGANISM: Artificial Sequence
<220> FEATURE:
<223> OTHER INFORMATION: Nb_10_TP879

<400> SEQUENCE: 10

```
Gln Val Gln Leu Val Glu Ser Gly Gly Gly Leu Val Gln Pro Gly Gly
1               5                   10                  15

Ser Leu Arg Leu Ser Cys Val Val Ser Gly Gly Thr Met Asn Ala Tyr
            20                  25                  30

Ala Ile Gly Trp Phe Arg Gln Ala Pro Gly Lys Glu Arg Glu Ala Val
        35                  40                  45

Ser Cys Ile Thr Ser Asn Ser Lys Tyr Thr Asn Tyr Ala Asp Ser Val
    50                  55                  60

Lys Gly Arg Phe Thr Ile Ser Arg Asp Asn Ala Lys Ser Thr Ala Tyr
65                  70                  75                  80

Leu Gln Met Asn Ser Leu Glu Pro Glu Asp Thr Ala Val Tyr Tyr Cys
            85                  90                  95

Ala Ala Ala Gln Phe Phe Asn Asp Gly His Gln Tyr Cys Pro Asn Pro
            100                 105                 110

Asn Tyr Trp Gly Gln Gly Thr Gln Val Thr Val Ser Ser
        115                 120                 125
```

<210> SEQ ID NO 11
<211> LENGTH: 117
<212> TYPE: PRT
<213> ORGANISM: Artificial Sequence
<220> FEATURE:
<223> OTHER INFORMATION: Nb_11_TP1104

<400> SEQUENCE: 11

```
Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asp Ser
            20                  25                  30

Pro Met Thr Trp Ala Arg Gln Ala Pro Gly Lys Arg Leu Glu Trp Val
        35                  40                  45
```

Ser Thr Ile Ser Ser Asp Gly Glu Lys Ile Gly Tyr Arg Asp Ala Val
    50              55              60

Lys Gly Arg Phe Thr Ile Ser Arg Asp Asn Ala Lys Asn Thr Leu Tyr
65              70              75              80

Leu Gln Met Asn Ser Leu Lys Pro Glu Asp Thr Ala Val Tyr Tyr Cys
                85              90              95

Leu Asn Val Val Leu Val Gly Arg Glu Val Phe Ser Asn Gly Thr Leu
            100             105             110

Val Thr Val Ser Ser
        115

<210> SEQ ID NO 12
<211> LENGTH: 123
<212> TYPE: PRT
<213> ORGANISM: Artificial Sequence
<220> FEATURE:
<223> OTHER INFORMATION: Nb_12_TP881

<400> SEQUENCE: 12

Gln Val Gln Leu Val Glu Ser Gly Gly Gly Leu Val Gln Pro Gly Gly
1               5               10              15

Ser Leu Arg Leu Ser Cys Ala Ala Phe Gly Phe Thr Phe Ser Asn Tyr
            20              25              30

Tyr Met Asn Trp Val Arg Gln Ala Pro Gly Lys Gly Leu Glu Trp Ile
        35              40              45

Ser Gly Ile Asn Ser Gly Gly Gly Thr Thr Ala Tyr Ala Asp Ser Val
    50              55              60

Lys Gly Arg Phe Thr Ile Ser Arg Asp Asn Ala Lys Asn Thr Leu Tyr
65              70              75              80

Leu Gln Met Asn Ser Leu Lys Pro Glu Asp Thr Ala Val Tyr Tyr Cys
                85              90              95

Ala Lys Gly Ala Val Arg Leu Val Ala Gly Ala Leu Arg Pro Ala Asp
            100             105             110

Trp Gly Gln Gly Thr Gln Val Thr Val Ser Ser
        115             120

<210> SEQ ID NO 13
<211> LENGTH: 124
<212> TYPE: PRT
<213> ORGANISM: Artificial Sequence
<220> FEATURE:
<223> OTHER INFORMATION: Nb_13_TP882

<400> SEQUENCE: 13

Gln Val Gln Leu Val Glu Ser Gly Gly Gly Leu Val Gln Pro Gly Gly
1               5               10              15

Ser Leu Thr Leu Ser Cys Ala Thr Ser Gly Phe Ser Leu Asp Tyr Tyr
            20              25              30

Ser Ile Gly Trp Phe Arg Gln Ala Pro Gly Lys Glu Arg Glu Gly Val
        35              40              45

Ser Cys Ile Ser Ser Thr Gly Gly Ser Thr Asn Tyr Val Asp Ser Val
    50              55              60

Lys Gly Arg Phe Thr Ile Ser Arg Asp Asn Ala Lys Asn Thr Val Tyr
65              70              75              80

Leu Gln Met Asn Ser Leu Lys Pro Glu Asp Thr Gly Val Tyr Tyr Cys
                85              90              95

Ala Ala Tyr Arg Arg Ser Gly Ala Tyr Cys Thr Ser Gly Gly Gln Asp

-continued

```
                100              105              110
Tyr Trp Gly Lys Gly Thr Leu Val Thr Val Ser Ser
        115              120

<210> SEQ ID NO 14
<211> LENGTH: 121
<212> TYPE: PRT
<213> ORGANISM: Artificial Sequence
<220> FEATURE:
<223> OTHER INFORMATION: Nb_14_TP883

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
            35                  40                  45

Ala Cys Ile Thr Ser Ser Glu Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Val Thr Tyr Ala Ser Cys Asn Glu Tyr Asp Tyr Ser Gly
            100              105              110

Gln Gly Thr Gln Val Thr Val Ser Ser
        115              120

<210> SEQ ID NO 15
<211> LENGTH: 120
<212> TYPE: PRT
<213> ORGANISM: Artificial Sequence
<220> FEATURE:
<223> OTHER INFORMATION: Nb_15_TP884

<400> SEQUENCE: 15

Gln Val Gln Leu Val Glu Ser Gly Gly Gly Leu Val Gln Pro Gly Gly
1               5                   10                  15

Ser Leu Thr Leu Ser Cys Val Ile Ser Gly Phe Arg Met Asp Ile Ala
            20                  25                  30

Thr Met Ser Trp Val Arg Gln Ala Pro Gly Lys Gly Leu Glu Trp Val
            35                  40                  45

Ala Gly Ile Ile Asn Tyr Arg Asn Phe Thr Trp Tyr Ser Asp Ser Val
        50                  55                  60

Lys Gly Arg Phe Thr Ile Ser Thr Asp Thr Ala Lys Ser Glu Val Tyr
65                  70                  75                  80

Leu Gln Met Asn Ser Leu Lys Ser Glu Asp Thr Ala Val Tyr Tyr Cys
                85                  90                  95

Ala His Gly Gly Ser Asp Thr Ala Thr Ser Arg Ala Ile Arg Gly Gln
            100              105              110

Gly Thr Gln Val Thr Val Ser Ser
        115              120

<210> SEQ ID NO 16
<211> LENGTH: 132
<212> TYPE: PRT
<213> ORGANISM: Artificial Sequence
<220> FEATURE:
```

<223> OTHER INFORMATION: Nb_16_TP894

<400> SEQUENCE: 16

Gln Val Gln Leu Val Glu Ser Gly Gly Gly Leu Val Gln Pro Gly Gly
1               5                   10                  15

Ser Leu Arg Leu Ser Cys Ala Val Ser Gly Leu Thr Leu Asp Phe Lys
            20                  25                  30

Gly Ile Gly Trp Phe Arg Gln Ala Pro Gly Lys Glu Arg Glu Gly Val
            35                  40                  45

Ser Cys Ile Asn Pro Ser Asp Ser Ser Ala Ala Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Val Ala Phe Glu Gln Lys Asn Ile Tyr Cys Ser Gly Tyr Ser Leu Thr
            100                 105                 110

Leu Ser Ala Arg Gly Val Met Asp His Trp Gly Lys Gly Thr Leu Val
        115                 120                 125

Thr Val Ser Ser
    130

<210> SEQ ID NO 17
<211> LENGTH: 138
<212> TYPE: PRT
<213> ORGANISM: Artificial Sequence
<220> FEATURE:
<223> OTHER INFORMATION: Nb_17_TP895

<400> SEQUENCE: 17

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu His Glu Gly Val
            35                  40                  45

Ser Cys Ile Ser Pro Ser Gly Gly Ser Thr Asn Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Val Ala Val Ala Arg Gly Thr Trp Gly Arg Gly Gly Val Asp Arg Thr
            100                 105                 110

Thr Asp Gln Ala Met Cys Ile Pro Arg Asp Pro Ser Val Asp Phe Trp
        115                 120                 125

Gly Lys Gly Thr Gln Val Thr Val Ser Ser
    130                 135

<210> SEQ ID NO 18
<211> LENGTH: 122
<212> TYPE: PRT
<213> ORGANISM: Artificial Sequence
<220> FEATURE:
<223> OTHER INFORMATION: Nb_18_TP885

<400> SEQUENCE: 18

Gln Val Gln Leu Val Glu Ser Gly Gly Gly Leu Val Gln Ala Gly Gly

-continued

```
1               5              10              15

Ser Val Arg Leu Ser Cys Ala Ala Ser Gly Phe Thr Phe Ser Ser Tyr
            20              25              30

Tyr Met Thr Trp Val Arg Gln Ala Pro Gly Lys Gly Pro Glu Trp Val
            35              40              45

Ser Ala Ile Asn Thr Gly Gly Asp Ala Thr Arg Tyr Ala Glu Ser Val
    50              55              60

Lys Gly Arg Phe Thr Ile Ser Arg Asp Asn Ala Lys Asn Met Leu Tyr
65              70              75              80

Leu Gln Met Asn Ser Leu Lys Pro Glu Asp Thr Ala Leu Tyr Tyr Cys
                85              90              95

Gly Arg Val Pro Gly Tyr Ser Asp Tyr Arg Gln Gly Tyr Asp Tyr Arg
            100             105             110

Gly Gln Gly Thr Leu Val Thr Val Ser Ser
        115             120
```

<210> SEQ ID NO 19
<211> LENGTH: 129
<212> TYPE: PRT
<213> ORGANISM: Artificial Sequence
<220> FEATURE:
<223> OTHER INFORMATION: Nb_19_TP886
<220> FEATURE:
<221> NAME/KEY: misc_feature
<222> LOCATION: (108)..(108)
<223> OTHER INFORMATION: Xaa can be any naturally occurring amino acid

<400> SEQUENCE: 19

```
Gln Val Gln Leu Val Glu Ser Gly Gly Gly Leu Val Gln Pro Gly Gly
1               5              10              15

Ser Leu Arg Leu Ser Cys Ala Ala Ser Gly Phe Thr Phe Ala Asn Tyr
            20              25              30

Tyr Met Ser Trp Val Arg Gln Ala Pro Gly Lys Gly Pro Glu Trp Val
            35              40              45

Ser Ala Ile Asn Thr Leu Gly Gly Lys Thr Lys Tyr Ala Asp Ser Val
    50              55              60

Lys Gly Arg Phe Thr Ile Ser Arg Asp Asn Ala Lys Ser Thr Leu Tyr
65              70              75              80

Leu Gln Met Asn Ser Leu Lys Pro Glu Asp Thr Ala Leu Tyr Tyr Cys
                85              90              95

Ala Arg Glu Val Thr Tyr Tyr Ser Gly Thr Tyr Xaa Leu Phe Gly Thr
            100             105             110

Lys Gln Glu Tyr Asp Tyr Arg Gly Gln Gly Thr Gln Val Thr Val Ser
        115             120             125

Ser
```

<210> SEQ ID NO 20
<211> LENGTH: 124
<212> TYPE: PRT
<213> ORGANISM: Artificial Sequence
<220> FEATURE:
<223> OTHER INFORMATION: Nb_20_TP887

<400> SEQUENCE: 20

```
Gln Val Gln Leu Val Glu Ser Gly Gly Gly Leu Val Gln Ala Gly Gly
1               5              10              15

Ser Leu Arg Leu Ser Cys Ala Ala Ser Gly Arg Thr Phe Ser Thr Tyr
            20              25              30
```

```
Ile Met Gly Trp Phe Arg Gln Ala Pro Gly Lys Glu Arg Glu Phe Val
        35                  40                  45

Ala Ala Ile Thr Trp Ile Gly Gly Ser Thr Tyr Tyr Ala Asp Ser Val
    50                  55                  60

Lys Gly Arg Phe Thr Ile Ser Arg Asp Tyr Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Gln Met Lys Phe Gln Ile Thr Thr Met Asp Ser Asp Tyr Asp
                100                 105                 110

Tyr Trp Gly Gln Gly Thr Gln Val Thr Val Ser Ser
        115                 120

<210> SEQ ID NO 21
<211> LENGTH: 124
<212> TYPE: PRT
<213> ORGANISM: Artificial Sequence
<220> FEATURE:
<223> OTHER INFORMATION: Nb_21_TP888

<400> SEQUENCE: 21

Gln Val Gln Leu Val Glu Ser Gly Gly Gly Leu Val Gln Asp Gly Gly
1               5                   10                  15

Ser Leu Arg Leu Ser Cys Ala Ala Ser Gly Arg Thr Phe Ser Val Tyr
            20                  25                  30

Ala Met Gly Trp Phe Arg Gln Ala Pro Gly Lys Glu Arg Glu Phe Val
        35                  40                  45

Ala Ala Ile Ser Trp Ile Gly Gly Ser Thr Tyr Ser Ala Asp Ser Val
    50                  55                  60

Lys Gly Arg Phe Thr Ile Ser Arg Glu Tyr Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Ile Phe His Arg Glu Ile Thr Thr Val Pro Arg Lys Tyr Asp
                100                 105                 110

Tyr Trp Gly Gln Gly Thr Gln Val Thr Val Ser Ser
        115                 120

<210> SEQ ID NO 22
<211> LENGTH: 124
<212> TYPE: PRT
<213> ORGANISM: Artificial Sequence
<220> FEATURE:
<223> OTHER INFORMATION: Nb_22_TP889

<400> SEQUENCE: 22

Gln Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Ala Ile Ser Trp Ile Gly Gly Ser Thr Tyr Tyr Ala Asp Ser Val
    50                  55                  60

Lys Gly Arg Phe Thr Ile Ser Arg Asp Tyr Ala Glu Asn Thr Leu Tyr
65                  70                  75                  80

Leu Gln Met Asn Ser Leu Lys Pro Glu Asp Thr Ala Val Tyr Tyr Cys
                85                  90                  95
```

-continued

```
Ala Ala Ser Thr Met Arg Ser Ile Asp Phe Tyr Val Thr Asp Phe Gly
            100                 105                 110

Ser Trp Gly Gln Gly Thr Leu Val Thr Val Ser Ser
        115                 120

<210> SEQ ID NO 23
<211> LENGTH: 124
<212> TYPE: PRT
<213> ORGANISM: Artificial Sequence
<220> FEATURE:
<223> OTHER INFORMATION: Nb_23_TP890

<400> SEQUENCE: 23

Gln Val Gln Leu Val Glu Ser Gly Gly Glu Ala Val Gln Thr Gly Gly
1               5                   10                  15

Ser Leu Arg Leu Ser Cys Ala Ala Ser Gly Arg Thr Phe Ser Thr Tyr
            20                  25                  30

Leu Met Gly Trp Phe Arg Gln Ala Pro Gly Lys Glu Arg Glu Phe Val
        35                  40                  45

Ala Ala Ile Ser Trp Ile Gly Gly Ser Thr Tyr Tyr Ala Asp Ser Val
    50                  55                  60

Lys Gly Arg Phe Thr Ile Ser Arg Asp Tyr Ala Glu Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Thr Phe Lys Trp Glu Val Thr Thr Thr Pro Asp Gly Tyr Asp
            100                 105                 110

Tyr Trp Gly Gln Gly Thr Gln Val Thr Val Ser Ser
        115                 120

<210> SEQ ID NO 24
<211> LENGTH: 125
<212> TYPE: PRT
<213> ORGANISM: Artificial Sequence
<220> FEATURE:
<223> OTHER INFORMATION: Nb_24_TP1106

<400> SEQUENCE: 24

Gln Val Gln Leu Val Glu Ser Gly Gly Gly Leu Val Gln Pro Gly Gly
1               5                   10                  15

Ser Leu Arg Leu Tyr Cys Ala Ala Ser Gly Arg Thr Asp Thr Thr Tyr
            20                  25                  30

Ala Leu Gly Trp Phe Arg Gln Pro Pro Gly Lys Glu Arg Gln Phe Val
        35                  40                  45

Ala Ser Ile Thr Trp Ile Gly Gly Ala Thr Asn Tyr Ala Ala Ser Val
    50                  55                  60

Lys Gly Arg Phe Thr Ile Ser Lys Asp Leu Gly Thr Asn Thr Phe Asn
65                  70                  75                  80

Leu Gln Met Asn Ser Leu Thr Pro Asp Asp Thr Ala Val Tyr Tyr Cys
                85                  90                  95

Ala Ala Ala Val Val Arg Gln Trp Pro Asn Ala His Gln Gly Ala Tyr
            100                 105                 110

Asp Tyr Trp Gly Gln Gly Thr Gln Val Thr Val Ser Ser
        115                 120                 125

<210> SEQ ID NO 25
<211> LENGTH: 127
<212> TYPE: PRT
```

-continued

```
<213> ORGANISM: Artificial Sequence
<220> FEATURE:
<223> OTHER INFORMATION: Nb_25_TP1129

<400> SEQUENCE: 25

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Ala
            20                  25                  30

Tyr Met Ser Trp Val Arg Gln Ala Pro Gly Lys Gly Pro Glu Trp Val
        35                  40                  45

Ser Thr Ile Ser Thr Gly Gly Gly Ile Val Asn Tyr Ala Asp Ser Val
    50                  55                  60

Lys Gly Arg Phe Ala Ile Ser Arg Asp Asn Ala Lys Asn Thr Leu Tyr
65                  70                  75                  80

Leu Gln Met Asn Lys Leu Lys Pro Glu Asp Thr Ala Leu Tyr Tyr Cys
                85                  90                  95

Ala Ser Asn Lys Gly Pro His Tyr His Ser Asp Tyr Phe Asp Ser Asn
            100                 105                 110

Leu Tyr Asp Phe Trp Gly Gln Gly Thr Leu Val Thr Val Ser Ser
        115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Nb_26_TP921

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Ala
            20                  25                  30

Tyr Met Ser Trp Val Arg Gln Ala Pro Gly Lys Gly Pro Glu Trp Val
        35                  40                  45

Ser Thr Ile Ser Thr Gly Gly Gly Ile Val Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Lys Leu Lys Pro Glu Asp Thr Ala Leu Tyr Tyr Cys
                85                  90                  95

Ala Ser Asn Lys Gly Pro His Tyr Tyr Ser Asp Tyr Phe Asp Ser Asn
            100                 105                 110

Gln Tyr Asp Phe Trp Gly Gln Gly Thr Gln Val Thr Val Ser Ser
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Nb_27_TP922

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Tyr Met Ser Trp Val Arg Gln Ala Pro Gly Lys Gly Leu Glu Trp Val
        35                  40                  45

Ser Asp Ile Ser Thr Asp Gly Gly Arg Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Phe Cys
                85                  90                  95

Ala Arg Glu Gly Trp Glu Asp Thr Ile Thr Glu Glu Pro Asn Asp Glu
                100                 105                 110

Asn Tyr Trp Gly Lys Gly Thr Leu Val Thr Val Ser Ser
        115                 120                 125
```

<210> SEQ ID NO 28
<211> LENGTH: 114
<212> TYPE: PRT
<213> ORGANISM: Artificial Sequence
<220> FEATURE:
<223> OTHER INFORMATION: Nb_28_TP923

<400> SEQUENCE: 28

```
Gln Val Gln Leu Val Glu Ser Gly Gly Gly Leu Val Gln Pro Gly Glu
1               5                   10                  15

Ser Leu Thr Leu Ser Cys Ala Ala Ser Gly Phe Thr Phe Ser Asn Val
        20                  25                  30

Ala Met Ser Trp Val Arg Gln Ala Pro Arg Lys Gly Leu Glu Trp Val
        35                  40                  45

Ser Ser Ile Ser Ser Asp Gly Gly Arg Thr Leu Tyr Ala Ala Ser Val
    50                  55                  60

Lys Gly Arg Phe Thr Val Ser Arg Asp Asn Ala Lys Asn Thr Leu Thr
65                  70                  75                  80

Leu Gln Met Asp Ser Leu Lys Ala Glu Asp Thr Ala Val Tyr Tyr Cys
                85                  90                  95

Thr Glu Glu Glu Gly Gly Thr Arg Gly Gln Gly Thr Gln Val Thr Val
                100                 105                 110

Ser Ser
```

<210> SEQ ID NO 29
<211> LENGTH: 126
<212> TYPE: PRT
<213> ORGANISM: Artificial Sequence
<220> FEATURE:
<223> OTHER INFORMATION: Nb_29_TP926

<400> SEQUENCE: 29

```
Gln Val Gln Leu Val Glu Ser Gly Gly Gly Leu Val Gln Ala Gly Gly
1               5                   10                  15

Ser Leu Arg Leu Ser Cys Ala Ala Ser Glu Thr Ile Phe Ser Ile Asn
        20                  25                  30

Val Met Gly Trp Phe Arg Gln Ala Pro Gly Lys Glu Arg Glu Leu Val
        35                  40                  45

Ala Lys Ile Ser Ser Val Gly Ser Thr Tyr Tyr Ala Asp Pro Val Lys
    50                  55                  60

Gly Arg Phe Thr Ile Ser Arg Asp Asp Thr Lys Asn Thr Leu Ser Leu
65                  70                  75                  80

Gln Met Asn Ser Leu Lys Pro Glu Asp Thr Ala Met Tyr Tyr Cys Ala
                85                  90                  95
```

-continued

```
Ala Cys Ala Arg Cys Phe Phe Val Pro Arg Met Thr Ser Ala Ala Ala
            100                 105                 110

Tyr Gly Tyr Trp Gly Gln Gly Thr Gln Val Thr Val Ser Ser
        115                 120                 125

<210> SEQ ID NO 30
<211> LENGTH: 125
<212> TYPE: PRT
<213> ORGANISM: Artificial Sequence
<220> FEATURE:
<223> OTHER INFORMATION: Nb_30_TP925

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Ser Tyr
            20                  25                  30

Gly Ile Gly Trp Phe Arg Gln Ala Pro Gly Lys Ala Arg Gln Ala Ile
        35                  40                  45

Leu Cys Ile Ser Ser Arg Gly Glu Thr Thr Thr Tyr Gly Asp Ser Val
    50                  55                  60

Gln Gly Arg Phe Thr Ser Ser Arg Asp Asn Ala Lys Asn Thr Ala Tyr
65                  70                  75                  80

Leu Gln Met Asn His Leu Lys Pro Glu Asp Thr Ala Val Tyr Tyr Cys
                85                  90                  95

Ala Ala Val Arg Leu Ser Arg Gly Tyr Leu Cys Arg Asn Tyr Asp Met
            100                 105                 110

Asp Tyr Trp Gly Lys Gly Thr Gln Val Thr Val Ser Ser
        115                 120                 125

<210> SEQ ID NO 31
<211> LENGTH: 126
<212> TYPE: PRT
<213> ORGANISM: Artificial Sequence
<220> FEATURE:
<223> OTHER INFORMATION: Nb_31_TP979

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Leu Ala Pro Gly Lys Glu Arg Glu Gly Val
        35                  40                  45

Ser Cys Ile Ser Ser Ser Gly Gly Ser Thr Asn Tyr Ala Asp Ser Val
    50                  55                  60

Lys Gly Arg Phe Thr Ile Ser Arg Asn Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Leu Gly Val Gly Asp Gly Ser Ser Cys Pro Asp Ser Ala Tyr Glu
            100                 105                 110

Tyr Ala Tyr Trp Gly Gln Gly Thr Gln Val Thr Val Ser Ser
        115                 120                 125

<210> SEQ ID NO 32
<211> LENGTH: 120
<212> TYPE: PRT
```

<213> ORGANISM: Artificial Sequence
<220> FEATURE:
<223> OTHER INFORMATION: Nb_32_TP984

<400> SEQUENCE: 32

```
Gln Val Gln Leu Val Glu Ser Gly Gly Gly Leu Val Gln Gly Gly Gly
1               5                   10                  15

Ser Leu Arg Leu Ser Cys Ala Ala Ser Arg Ser Ile Phe Ser Ile Asn
            20                  25                  30

Ala Met Gly Trp Tyr Arg Gln Ala Leu Gly Lys Glu Arg Glu Leu Val
            35                  40                  45

Ala Ala Ile Ser Ser Gly Gly Ser Thr Tyr Tyr Val Asp Ser Val Lys
        50                  55                  60

Gly Arg Phe Thr Ile Ser Arg Asp His Val Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Leu Gln Ser Trp Gly Ser Tyr Pro His Asp Asp Tyr Trp Gly Gln
            100                 105                 110

Gly Thr Gln Val Thr Val Ser Ser
        115                 120
```

<210> SEQ ID NO 33
<211> LENGTH: 122
<212> TYPE: PRT
<213> ORGANISM: Artificial Sequence
<220> FEATURE:
<223> OTHER INFORMATION: Nb_33_TP924

<400> SEQUENCE: 33

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
            35                  40                  45

Gly Asp Ile Asn Gly Val Gly Asn Tyr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Ala Pro Gly Gly Ala Ala Thr Val Val Gly Gly Pro Tyr Asp Tyr Trp
            100                 105                 110

Gly Gln Gly Thr Gln Val Thr Val Ser Ser
        115                 120
```

<210> SEQ ID NO 34
<211> LENGTH: 125
<212> TYPE: PRT
<213> ORGANISM: Artificial Sequence
<220> FEATURE:
<223> OTHER INFORMATION: Nb_34_TP929

<400> SEQUENCE: 34

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30
```

```
Ala Ile Gly Trp Phe Arg Gln Ala Pro Gly Lys Glu Arg Glu Gly Val
        35                  40                  45

Ser Cys Ile Ser Ser Ser Ser Gly Arg Thr Asp Tyr Val Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Leu Glu Arg Ala Thr Met Cys Pro Arg Asp Pro Thr Trp Tyr
            100                 105                 110

Asp Tyr Trp Gly Gln Gly Thr Gln Val Thr Val Ser Ser
        115                 120                 125
```

```
<210> SEQ ID NO 35
<211> LENGTH: 21
<212> TYPE: PRT
<213> ORGANISM: Artificial Sequence
<220> FEATURE:
<223> OTHER INFORMATION: TP896 CDRIII

<400> SEQUENCE: 35

Gly Lys Phe Pro Val Glu Ser Arg Arg His Gly Gly Thr Ala Gln Trp
1               5                   10                  15

Asp Glu Tyr Asp Tyr
            20
```

```
<210> SEQ ID NO 36
<211> LENGTH: 7
<212> TYPE: PRT
<213> ORGANISM: Artificial Sequence
<220> FEATURE:
<223> OTHER INFORMATION: TP897 CDRIII

<400> SEQUENCE: 36

Leu Val Phe Gly Gly Glu Tyr
1               5
```

```
<210> SEQ ID NO 37
<211> LENGTH: 17
<212> TYPE: PRT
<213> ORGANISM: Artificial Sequence
<220> FEATURE:
<223> OTHER INFORMATION: TP1170 CDRIII

<400> SEQUENCE: 37

Thr Tyr Ser Gly Asn Tyr Tyr Ser Asn Tyr Thr Val Ala Asn Tyr Gly
1               5                   10                  15

Thr
```

```
<210> SEQ ID NO 38
<211> LENGTH: 20
<212> TYPE: PRT
<213> ORGANISM: Artificial Sequence
<220> FEATURE:
<223> OTHER INFORMATION: TP975 CDRIII

<400> SEQUENCE: 38

Gly Ser Gly Pro Ala Phe Arg Leu Ser Gly Gly Ser Trp Ser Pro Arg
1               5                   10                  15

Gly Asp Gly Ser
            20
```

```
<210> SEQ ID NO 39
<211> LENGTH: 17
<212> TYPE: PRT
<213> ORGANISM: Artificial Sequence
<220> FEATURE:
<223> OTHER INFORMATION: TP1014 CDRIII

<400> SEQUENCE: 39

Arg Gly Ser Ser Asp Tyr Asp Val Ala Met Gln Gly His Glu Tyr Thr
1               5                   10                  15

Tyr

<210> SEQ ID NO 40
<211> LENGTH: 11
<212> TYPE: PRT
<213> ORGANISM: Artificial Sequence
<220> FEATURE:
<223> OTHER INFORMATION: TP1107 CDRIII

<400> SEQUENCE: 40

Gly Trp Val Arg Leu Pro Asp Pro Asp Leu Val
1               5                   10

<210> SEQ ID NO 41
<211> LENGTH: 17
<212> TYPE: PRT
<213> ORGANISM: Artificial Sequence
<220> FEATURE:
<223> OTHER INFORMATION: TP878 CDRIII

<400> SEQUENCE: 41

Cys Pro Gly Asp Tyr Thr Ser Thr Ile Cys Asn Ser Asp Gly Met Asp
1               5                   10                  15

Tyr

<210> SEQ ID NO 42
<211> LENGTH: 16
<212> TYPE: PRT
<213> ORGANISM: Artificial Sequence
<220> FEATURE:
<223> OTHER INFORMATION: TP879 CDRIII

<400> SEQUENCE: 42

Ala Gln Phe Phe Asn Asp Gly His Gln Tyr Cys Pro Asn Pro Asn Tyr
1               5                   10                  15

<210> SEQ ID NO 43
<211> LENGTH: 8
<212> TYPE: PRT
<213> ORGANISM: Artificial Sequence
<220> FEATURE:
<223> OTHER INFORMATION: TP1104 CDRIII

<400> SEQUENCE: 43

Val Val Leu Val Gly Arg Glu Val
1               5

<210> SEQ ID NO 44
<211> LENGTH: 14
<212> TYPE: PRT
<213> ORGANISM: Artificial Sequence
<220> FEATURE:
<223> OTHER INFORMATION: TP881 CDRIII

<400> SEQUENCE: 44
```

-continued

```
Gly Ala Val Arg Leu Val Ala Gly Ala Leu Arg Pro Ala Asp
1               5                   10

<210> SEQ ID NO 45
<211> LENGTH: 15
<212> TYPE: PRT
<213> ORGANISM: Artificial Sequence
<220> FEATURE:
<223> OTHER INFORMATION: TP882 CDRIII

<400> SEQUENCE: 45

Tyr Arg Arg Ser Gly Ala Tyr Cys Thr Ser Gly Gly Gln Asp Tyr
1               5                   10                  15

<210> SEQ ID NO 46
<211> LENGTH: 12
<212> TYPE: PRT
<213> ORGANISM: Artificial Sequence
<220> FEATURE:
<223> OTHER INFORMATION: TP883 CDRIII

<400> SEQUENCE: 46

Ala Val Thr Tyr Ala Ser Cys Asn Glu Tyr Asp Tyr
1               5                   10

<210> SEQ ID NO 47
<211> LENGTH: 11
<212> TYPE: PRT
<213> ORGANISM: Artificial Sequence
<220> FEATURE:
<223> OTHER INFORMATION: TP884 CDRIII

<400> SEQUENCE: 47

Gly Gly Ser Asp Thr Ala Thr Ser Arg Ala Ile
1               5                   10

<210> SEQ ID NO 48
<211> LENGTH: 23
<212> TYPE: PRT
<213> ORGANISM: Artificial Sequence
<220> FEATURE:
<223> OTHER INFORMATION: TP894 CDRIII

<400> SEQUENCE: 48

Phe Glu Gln Lys Asn Ile Tyr Cys Ser Gly Tyr Ser Leu Thr Leu Ser
1               5                   10                  15

Ala Arg Gly Val Met Asp His
            20

<210> SEQ ID NO 49
<211> LENGTH: 29
<212> TYPE: PRT
<213> ORGANISM: Artificial Sequence
<220> FEATURE:
<223> OTHER INFORMATION: TP895 CDRIII

<400> SEQUENCE: 49

Val Ala Arg Gly Thr Trp Gly Arg Gly Gly Val Asp Arg Thr Thr Asp
1               5                   10                  15

Gln Ala Met Cys Ile Pro Arg Asp Pro Ser Val Asp Phe
            20                  25

<210> SEQ ID NO 50
<211> LENGTH: 13
<212> TYPE: PRT
<213> ORGANISM: Artificial Sequence
```

```
<220> FEATURE:
<223> OTHER INFORMATION: TP885 CDRIII

<400> SEQUENCE: 50

Val Pro Gly Tyr Ser Asp Tyr Arg Gln Gly Tyr Asp Tyr
1               5                   10

<210> SEQ ID NO 51
<211> LENGTH: 20
<212> TYPE: PRT
<213> ORGANISM: Artificial Sequence
<220> FEATURE:
<223> OTHER INFORMATION: TP886 CDRIII

<400> SEQUENCE: 51

Glu Val Thr Tyr Tyr Ser Gly Thr Tyr Tyr Leu Phe Gly Thr Lys Gln
1               5                   10                  15

Glu Tyr Asp Tyr
            20

<210> SEQ ID NO 52
<211> LENGTH: 15
<212> TYPE: PRT
<213> ORGANISM: Artificial Sequence
<220> FEATURE:
<223> OTHER INFORMATION: TP887 CDRIII

<400> SEQUENCE: 52

Gln Met Lys Phe Gln Ile Thr Thr Met Asp Ser Asp Tyr Asp Tyr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: TP888 CDRIII

<400> SEQUENCE: 53

Ile Phe His Arg Glu Ile Thr Thr Val Pro Arg Lys Tyr Asp Tyr
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: TP889 CDRIII

<400> SEQUENCE: 54

Ser Thr Met Arg Ser Ile Asp Phe Tyr Val Thr Asp Phe Gly Ser
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: TP890 CDRIII

<400> SEQUENCE: 55

Thr Phe Lys Trp Glu Val Thr Thr Thr Pro Asp Gly Tyr Asp Tyr
1               5                   10                  15

<210> SEQ ID NO 56
<211> LENGTH: 16
```

-continued

```
<212> TYPE: PRT
<213> ORGANISM: Artificial Sequence
<220> FEATURE:
<223> OTHER INFORMATION: TP1106 CDRIII

<400> SEQUENCE: 56

Ala Val Val Arg Gln Trp Pro Asn Ala His Gln Gly Ala Tyr Asp Tyr
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: TP1129 CDRIII

<400> SEQUENCE: 57

Asn Lys Gly Pro His Tyr His Ser Asp Tyr Phe Asp Ser Asn Leu Tyr
1               5                   10                  15

Asp Phe

<210> SEQ ID NO 58
<211> LENGTH: 16
<212> TYPE: PRT
<213> ORGANISM: Artificial Sequence
<220> FEATURE:
<223> OTHER INFORMATION: TP922 CDRIII

<400> SEQUENCE: 58

Glu Gly Trp Glu Asp Thr Ile Thr Glu Glu Pro Asn Asp Glu Asn Tyr
1               5                   10                  15

<210> SEQ ID NO 59
<211> LENGTH: 5
<212> TYPE: PRT
<213> ORGANISM: Artificial Sequence
<220> FEATURE:
<223> OTHER INFORMATION: TP923 CDRIII

<400> SEQUENCE: 59

Glu Glu Gly Gly Thr
1               5

<210> SEQ ID NO 60
<211> LENGTH: 18
<212> TYPE: PRT
<213> ORGANISM: Artificial Sequence
<220> FEATURE:
<223> OTHER INFORMATION: TP926 CDRIII

<400> SEQUENCE: 60

Cys Ala Arg Cys Phe Phe Val Pro Arg Met Thr Ser Ala Ala Ala Tyr
1               5                   10                  15

Gly Tyr

<210> SEQ ID NO 61
<211> LENGTH: 16
<212> TYPE: PRT
<213> ORGANISM: Artificial Sequence
<220> FEATURE:
<223> OTHER INFORMATION: TP925 CDRIII

<400> SEQUENCE: 61

Val Arg Leu Ser Arg Gly Tyr Leu Cys Arg Asn Tyr Asp Met Asp Tyr
1               5                   10                  15
```

```
<210> SEQ ID NO 62
<211> LENGTH: 17
<212> TYPE: PRT
<213> ORGANISM: Artificial Sequence
<220> FEATURE:
<223> OTHER INFORMATION: TP979 CDRIII

<400> SEQUENCE: 62

Gly Val Gly Asp Gly Ser Ser Cys Pro Asp Ser Ala Tyr Glu Tyr Ala
1               5                   10                  15

Tyr

<210> SEQ ID NO 63
<211> LENGTH: 12
<212> TYPE: PRT
<213> ORGANISM: Artificial Sequence
<220> FEATURE:
<223> OTHER INFORMATION: TP984 CDRIII

<400> SEQUENCE: 63

Leu Gln Ser Trp Gly Ser Tyr Pro His Asp Asp Tyr
1               5                   10

<210> SEQ ID NO 64
<211> LENGTH: 13
<212> TYPE: PRT
<213> ORGANISM: Artificial Sequence
<220> FEATURE:
<223> OTHER INFORMATION: TP924 CDRIII

<400> SEQUENCE: 64

Gly Gly Ala Ala Thr Val Val Gly Gly Pro Tyr Asp Tyr
1               5                   10

<210> SEQ ID NO 65
<211> LENGTH: 16
<212> TYPE: PRT
<213> ORGANISM: Artificial Sequence
<220> FEATURE:
<223> OTHER INFORMATION: TP929 CDRIII

<400> SEQUENCE: 65

Leu Glu Arg Ala Thr Met Cys Pro Arg Asp Pro Thr Trp Tyr Asp Tyr
1               5                   10                  15

<210> SEQ ID NO 66
<211> LENGTH: 25
<212> TYPE: PRT
<213> ORGANISM: Artificial Sequence
<220> FEATURE:
<223> OTHER INFORMATION: TP896 FWI

<400> SEQUENCE: 66

Gln Val Gln Leu Val Glu Ser Gly Gly Gly Leu Ala Gln Pro Gly Gly
1               5                   10                  15

Ser Leu Arg Leu Ser Cys Ala Val Ser
            20                  25

<210> SEQ ID NO 67
<211> LENGTH: 10
<212> TYPE: PRT
<213> ORGANISM: Artificial Sequence
<220> FEATURE:
<223> OTHER INFORMATION: TP896 CDRI

<400> SEQUENCE: 67
```

```
Gly Phe Arg Phe Ser Phe Tyr Gln Met Thr
1               5               10

<210> SEQ ID NO 68
<211> LENGTH: 14
<212> TYPE: PRT
<213> ORGANISM: Artificial Sequence
<220> FEATURE:
<223> OTHER INFORMATION: TP896 FWII

<400> SEQUENCE: 68

Trp Val Arg Gln Ala Pro Gly Lys Gly Leu Glu Trp Val Ala
1               5               10

<210> SEQ ID NO 69
<211> LENGTH: 8
<212> TYPE: PRT
<213> ORGANISM: Artificial Sequence
<220> FEATURE:
<223> OTHER INFORMATION: TP896 CDRII

<400> SEQUENCE: 69

Asp Ile Asn Ser Ala Gly Gly Thr
1               5

<210> SEQ ID NO 70
<211> LENGTH: 41
<212> TYPE: PRT
<213> ORGANISM: Artificial Sequence
<220> FEATURE:
<223> OTHER INFORMATION: TP896 FWIII

<400> SEQUENCE: 70

Thr Tyr Tyr Ala Asp Ser Val Lys Gly Arg Phe Ala Ile Ser Arg Asp
1               5               10              15

Asn Ala Lys Asn Thr Leu Tyr Leu Gln Met Asn Ser Leu Lys Pro Glu
            20              25              30

Asp Thr Ala Val Tyr Tyr Cys Ala Lys
        35              40

<210> SEQ ID NO 71
<211> LENGTH: 11
<212> TYPE: PRT
<213> ORGANISM: Artificial Sequence
<220> FEATURE:
<223> OTHER INFORMATION: TP896 FWIV

<400> SEQUENCE: 71

Trp Gly Gln Gly Thr Arg Val Thr Val Ser Ser
1               5               10

<210> SEQ ID NO 72
<211> LENGTH: 25
<212> TYPE: PRT
<213> ORGANISM: Artificial Sequence
<220> FEATURE:
<223> OTHER INFORMATION: TP897 FWI

<400> SEQUENCE: 72

Gln Val Gln Leu Val Glu Ser Gly Gly Gly Leu Val Gln Ala Gly Asp
1               5               10              15

Ser Leu Arg Leu Ser Cys Val Ala Ser
            20              25
```

```
<210> SEQ ID NO 73
<211> LENGTH: 10
<212> TYPE: PRT
<213> ORGANISM: Artificial Sequence
<220> FEATURE:
<223> OTHER INFORMATION: TP897 CDRI

<400> SEQUENCE: 73

Gly Arg Ser Leu Asp Gly Ala Thr Met Arg
1               5                   10

<210> SEQ ID NO 74
<211> LENGTH: 14
<212> TYPE: PRT
<213> ORGANISM: Artificial Sequence
<220> FEATURE:
<223> OTHER INFORMATION: TP897 FWII

<400> SEQUENCE: 74

Trp Tyr Arg Gln Ala Pro Gly Lys Glu Arg Glu Phe Val Ala
1               5                   10

<210> SEQ ID NO 75
<211> LENGTH: 8
<212> TYPE: PRT
<213> ORGANISM: Artificial Sequence
<220> FEATURE:
<223> OTHER INFORMATION: TP897 CDRII

<400> SEQUENCE: 75

Gly Ile Phe Trp Asp Glu Ile Gly
1               5

<210> SEQ ID NO 76
<211> LENGTH: 41
<212> TYPE: PRT
<213> ORGANISM: Artificial Sequence
<220> FEATURE:
<223> OTHER INFORMATION: TP897 FWIII

<400> SEQUENCE: 76

Thr Glu Tyr Ala Asp Thr Ala Lys Gly Arg Phe Thr Ile Ser Arg Asp
1               5                   10                  15

Asn Ala Lys Asn Thr Ile Tyr Leu Gln Met Thr Asn Leu Arg Ser Glu
            20                  25                  30

Asp Thr Ala Met Tyr Tyr Cys Asn Gly
        35                  40

<210> SEQ ID NO 77
<211> LENGTH: 11
<212> TYPE: PRT
<213> ORGANISM: Artificial Sequence
<220> FEATURE:
<223> OTHER INFORMATION: TP897 FWIV

<400> SEQUENCE: 77

Trp Gly Gln Gly Thr Gln Val Thr Val Ser Ser
1               5                   10

<210> SEQ ID NO 78
<211> LENGTH: 25
<212> TYPE: PRT
<213> ORGANISM: Artificial Sequence
<220> FEATURE:
<223> OTHER INFORMATION: TP974 FWI

<400> SEQUENCE: 78
```

-continued

```
Gln Val Gln Leu Val Glu Ser Gly Gly Gly Trp Val Gln Pro Gly Gly
1               5                   10                  15

Ser Leu Arg Leu Ser Cys Ala Ala Ser
            20                  25

<210> SEQ ID NO 79
<211> LENGTH: 10
<212> TYPE: PRT
<213> ORGANISM: Artificial Sequence
<220> FEATURE:
<223> OTHER INFORMATION: TP974 CDRI

<400> SEQUENCE: 79

Gly Phe Thr Phe Ser Ser Tyr Ala Met Ser
1               5                   10

<210> SEQ ID NO 80
<211> LENGTH: 14
<212> TYPE: PRT
<213> ORGANISM: Artificial Sequence
<220> FEATURE:
<223> OTHER INFORMATION: TP974 FWII

<400> SEQUENCE: 80

Trp Val Arg Gln Ala Pro Gly Lys Gly Pro Glu Trp Val Ser
1               5                   10

<210> SEQ ID NO 81
<211> LENGTH: 8
<212> TYPE: PRT
<213> ORGANISM: Artificial Sequence
<220> FEATURE:
<223> OTHER INFORMATION: TP974 CDRII

<400> SEQUENCE: 81

Ala Ile Asp Thr Gly Gly Gly Tyr
1               5

<210> SEQ ID NO 82
<211> LENGTH: 41
<212> TYPE: PRT
<213> ORGANISM: Artificial Sequence
<220> FEATURE:
<223> OTHER INFORMATION: TP974 FWIII

<400> SEQUENCE: 82

Thr Tyr Tyr Ala Asp Ser Val Lys Gly Arg Phe Thr Ile Ser Arg Asp
1               5                   10                  15

Asn Ala Lys Asn Thr Leu Tyr Leu Gln Met Asn Ser Leu Ser Pro Glu
            20                  25                  30

Asp Thr Ala Leu Tyr Tyr Cys Ala Thr
        35                  40

<210> SEQ ID NO 83
<211> LENGTH: 17
<212> TYPE: PRT
<213> ORGANISM: Artificial Sequence
<220> FEATURE:
<223> OTHER INFORMATION: TP974 CDRIII

<400> SEQUENCE: 83

Thr Tyr Ser Gly Asn Tyr Tyr Ser Asp Tyr Thr Ile Gly Asn Ser Asp
1               5                   10                  15

Tyr
```

```
<210> SEQ ID NO 84
<211> LENGTH: 11
<212> TYPE: PRT
<213> ORGANISM: Artificial Sequence
<220> FEATURE:
<223> OTHER INFORMATION: TP974 FWIV

<400> SEQUENCE: 84

Arg Gly Gln Gly Thr Leu Val Thr Val Ser Ser
1               5                   10

<210> SEQ ID NO 85
<211> LENGTH: 25
<212> TYPE: PRT
<213> ORGANISM: Artificial Sequence
<220> FEATURE:
<223> OTHER INFORMATION: TP1079 FWI

<400> SEQUENCE: 85

Gln Val Gln Leu Val Glu Ser Gly Gly Gly Leu Val Leu Pro Gly Gly
1               5                   10                  15

Ser Leu Arg Leu Ser Cys Val Ala Ser
            20                  25

<210> SEQ ID NO 86
<211> LENGTH: 10
<212> TYPE: PRT
<213> ORGANISM: Artificial Sequence
<220> FEATURE:
<223> OTHER INFORMATION: TP1079 CDRI

<400> SEQUENCE: 86

Gly Phe Thr Phe Ser Asp Thr Ala Met Met
1               5                   10

<210> SEQ ID NO 87
<211> LENGTH: 14
<212> TYPE: PRT
<213> ORGANISM: Artificial Sequence
<220> FEATURE:
<223> OTHER INFORMATION: TP1079 FWII

<400> SEQUENCE: 87

Trp Val Arg Gln Ala Pro Gly Lys Gly Arg Glu Trp Val Ala
1               5                   10

<210> SEQ ID NO 88
<211> LENGTH: 8
<212> TYPE: PRT
<213> ORGANISM: Artificial Sequence
<220> FEATURE:
<223> OTHER INFORMATION: TP1079 CDRII

<400> SEQUENCE: 88

Ala Ile Asp Thr Gly Gly Ser Ser
1               5

<210> SEQ ID NO 89
<211> LENGTH: 41
<212> TYPE: PRT
<213> ORGANISM: Artificial Sequence
<220> FEATURE:
<223> OTHER INFORMATION: TP1079 FWIII

<400> SEQUENCE: 89
```

```
Thr Tyr Tyr Ala Asp Ser Val Gln Gly Arg Phe Thr Ile Ser Arg Asp
1               5                   10                  15

Ser Ala Lys Asn Thr Leu Tyr Leu Gln Met Asn Ser Leu Lys Pro Glu
            20                  25                  30

Asp Thr Ala Arg Tyr Tyr Cys Ala Lys
        35                  40
```

<210> SEQ ID NO 90
<211> LENGTH: 11
<212> TYPE: PRT
<213> ORGANISM: Artificial Sequence
<220> FEATURE:
<223> OTHER INFORMATION: TP1079 FWIV

<400> SEQUENCE: 90

```
Thr Gly Arg Gly Thr Leu Val Thr Val Ser Ser
1               5                   10
```

<210> SEQ ID NO 91
<211> LENGTH: 25
<212> TYPE: PRT
<213> ORGANISM: Artificial Sequence
<220> FEATURE:
<223> OTHER INFORMATION: TP1170 FWI

<400> SEQUENCE: 91

```
Gln Val Gln Leu Val Glu Ser Gly Gly Gly Trp Val Gln Pro Gly Gly
1               5                   10                  15

Ser Leu Arg Leu Ser Cys Ala Ala Ser
            20                  25
```

<210> SEQ ID NO 92
<211> LENGTH: 10
<212> TYPE: PRT
<213> ORGANISM: Artificial Sequence
<220> FEATURE:
<223> OTHER INFORMATION: TP1170 CDRI

<400> SEQUENCE: 92

```
Gly Phe Thr Phe Ser Asp Thr Ala Met Met
1               5                   10
```

<210> SEQ ID NO 93
<211> LENGTH: 14
<212> TYPE: PRT
<213> ORGANISM: Artificial Sequence
<220> FEATURE:
<223> OTHER INFORMATION: TP1170 FWII

<400> SEQUENCE: 93

```
Trp Val Arg Gln Ala Pro Gly Lys Gly Arg Glu Trp Val Ala
1               5                   10
```

<210> SEQ ID NO 94
<211> LENGTH: 8
<212> TYPE: PRT
<213> ORGANISM: Artificial Sequence
<220> FEATURE:
<223> OTHER INFORMATION: TP1170 CDRII

<400> SEQUENCE: 94

```
Ala Ile Asp Thr Gly Gly Gly Tyr
1               5
```

<210> SEQ ID NO 95

```
<211> LENGTH: 41
<212> TYPE: PRT
<213> ORGANISM: Artificial Sequence
<220> FEATURE:
<223> OTHER INFORMATION: TP1170 FWIII

<400> SEQUENCE: 95

Thr Tyr Tyr Ala Asp Ser Val Lys Gly Arg Phe Thr Ile Ser Arg Asp
1               5                   10                  15

Asn Ala Lys Asn Thr Leu Tyr Leu Gln Met Asn Ser Leu Lys Pro Glu
            20                  25                  30

Asp Thr Ala Arg Tyr Tyr Cys Ala Lys
        35                  40

<210> SEQ ID NO 96
<211> LENGTH: 11
<212> TYPE: PRT
<213> ORGANISM: Artificial Sequence
<220> FEATURE:
<223> OTHER INFORMATION: TP1170 FWIV

<400> SEQUENCE: 96

Thr Gly Arg Gly Thr Leu Val Thr Val Ser Ser
1               5                   10

<210> SEQ ID NO 97
<211> LENGTH: 25
<212> TYPE: PRT
<213> ORGANISM: Artificial Sequence
<220> FEATURE:
<223> OTHER INFORMATION: TP975 FWI

<400> SEQUENCE: 97

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 98
<211> LENGTH: 10
<212> TYPE: PRT
<213> ORGANISM: Artificial Sequence
<220> FEATURE:
<223> OTHER INFORMATION: TP975 CDRI

<400> SEQUENCE: 98

Gly Phe Thr Phe Ser Asn Tyr Asp Met Ser
1               5                   10

<210> SEQ ID NO 99
<211> LENGTH: 14
<212> TYPE: PRT
<213> ORGANISM: Artificial Sequence
<220> FEATURE:
<223> OTHER INFORMATION: TP975 FWII

<400> SEQUENCE: 99

Trp Val Arg Gln Ala Pro Gly Lys Gly Leu Glu Trp Val Ser
1               5                   10

<210> SEQ ID NO 100
<211> LENGTH: 8
<212> TYPE: PRT
<213> ORGANISM: Artificial Sequence
<220> FEATURE:
<223> OTHER INFORMATION: TP975 CDRII
```

<400> SEQUENCE: 100

Ala Ile Ser Ser Gly Gly Gly Ser
1               5

<210> SEQ ID NO 101
<211> LENGTH: 41
<212> TYPE: PRT
<213> ORGANISM: Artificial Sequence
<220> FEATURE:
<223> OTHER INFORMATION: TP975 FWIII

<400> SEQUENCE: 101

Thr Tyr Tyr Val Asp Ser Val Lys Gly Arg Phe Thr Ile Ser Arg Asp
1               5                   10                  15

Asn Ala Lys Asn Thr Val Tyr Leu Gln Met Asn Ser Leu Lys Pro Glu
            20                  25                  30

Asp Thr Ala Val Tyr Tyr Cys Ala Thr
        35                  40

<210> SEQ ID NO 102
<211> LENGTH: 11
<212> TYPE: PRT
<213> ORGANISM: Artificial Sequence
<220> FEATURE:
<223> OTHER INFORMATION: TP975 FWIV

<400> SEQUENCE: 102

Arg Gly Gln Gly Thr Leu Val Thr Val Ser Ser
1               5                   10

<210> SEQ ID NO 103
<211> LENGTH: 25
<212> TYPE: PRT
<213> ORGANISM: Artificial Sequence
<220> FEATURE:
<223> OTHER INFORMATION: TP1014 FWI

<400> SEQUENCE: 103

Gln Val Gln Leu Val Glu Ser Gly Gly Gly Glu Val Gln Ala Gly Gly
1               5                   10                  15

Ser Leu Arg Leu Ser Cys Ala Ala Ser
            20                  25

<210> SEQ ID NO 104
<211> LENGTH: 10
<212> TYPE: PRT
<213> ORGANISM: Artificial Sequence
<220> FEATURE:
<223> OTHER INFORMATION: TP1014 CDRI

<400> SEQUENCE: 104

Gly Arg Thr Phe Ser Arg Asn Val Met Gly
1               5                   10

<210> SEQ ID NO 105
<211> LENGTH: 14
<212> TYPE: PRT
<213> ORGANISM: Artificial Sequence
<220> FEATURE:
<223> OTHER INFORMATION: TP1014 FWII

<400> SEQUENCE: 105

Trp Phe Arg Gln Ala Pro Gly Lys Glu Arg Glu Phe Leu Ala
1               5                   10

```
<210> SEQ ID NO 106
<211> LENGTH: 8
<212> TYPE: PRT
<213> ORGANISM: Artificial Sequence
<220> FEATURE:
<223> OTHER INFORMATION: TP1014 CDRII

<400> SEQUENCE: 106

Ala Ile Asn Trp Ser Gly Asn Ser
1               5

<210> SEQ ID NO 107
<211> LENGTH: 41
<212> TYPE: PRT
<213> ORGANISM: Artificial Sequence
<220> FEATURE:
<223> OTHER INFORMATION: TP1014 FWIII

<400> SEQUENCE: 107

Ile Gly Tyr Arg Asp Ser Val Lys Gly Arg Phe Thr Ala Ser Arg Asp
1               5                   10                  15

Asn Val Asn Asn Thr Leu Tyr Leu Arg Met Asn Asn Leu Lys Pro Glu
            20                  25                  30

Asp Thr Ala Val Tyr Tyr Cys Ala Ala
        35                  40

<210> SEQ ID NO 108
<211> LENGTH: 11
<212> TYPE: PRT
<213> ORGANISM: Artificial Sequence
<220> FEATURE:
<223> OTHER INFORMATION: TP1014 FWIV

<400> SEQUENCE: 108

Trp Gly Gln Gly Thr Gln Val Thr Val Ser Ser
1               5                   10

<210> SEQ ID NO 109
<211> LENGTH: 25
<212> TYPE: PRT
<213> ORGANISM: Artificial Sequence
<220> FEATURE:
<223> OTHER INFORMATION: TP1107 FWI

<400> SEQUENCE: 109

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 110
<211> LENGTH: 10
<212> TYPE: PRT
<213> ORGANISM: Artificial Sequence
<220> FEATURE:
<223> OTHER INFORMATION: TP1107 CDRI

<400> SEQUENCE: 110

Gly Phe Thr Phe Ser Asp Thr Trp Met Asn
1               5                   10

<210> SEQ ID NO 111
<211> LENGTH: 14
<212> TYPE: PRT
```

-continued

<213> ORGANISM: Artificial Sequence
<220> FEATURE:
<223> OTHER INFORMATION: TP1107 FWII

<400> SEQUENCE: 111

Trp Val Arg Gln Ala Pro Gly Lys Gly Leu Tyr Trp Ile Ser
1               5                   10

<210> SEQ ID NO 112
<211> LENGTH: 8
<212> TYPE: PRT
<213> ORGANISM: Artificial Sequence
<220> FEATURE:
<223> OTHER INFORMATION: TP1107 CDRII

<400> SEQUENCE: 112

Ala Ile Asn Pro Asp Gly Gly Asn
1               5

<210> SEQ ID NO 113
<211> LENGTH: 41
<212> TYPE: PRT
<213> ORGANISM: Artificial Sequence
<220> FEATURE:
<223> OTHER INFORMATION: TP1107 FWIII

<400> SEQUENCE: 113

Thr Ala Tyr Ala Asp Ser Val Lys Gly Arg Phe Thr Ile Ser Arg Asp
1               5                   10                  15

Asn Ala Lys Asn Met Val Tyr Leu Gln Met Asp Asn Leu Arg Pro Glu
            20                  25                  30

Asp Thr Ala Met Tyr Tyr Cys Ala Lys
        35                  40

<210> SEQ ID NO 114
<211> LENGTH: 11
<212> TYPE: PRT
<213> ORGANISM: Artificial Sequence
<220> FEATURE:
<223> OTHER INFORMATION: TP1107 FWIV

<400> SEQUENCE: 114

Arg Gly Gln Gly Thr Gln Val Thr Val Ser Ser
1               5                   10

<210> SEQ ID NO 115
<211> LENGTH: 25
<212> TYPE: PRT
<213> ORGANISM: Artificial Sequence
<220> FEATURE:
<223> OTHER INFORMATION: TP878 FWI

<400> SEQUENCE: 115

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 116
<211> LENGTH: 10
<212> TYPE: PRT
<213> ORGANISM: Artificial Sequence
<220> FEATURE:
<223> OTHER INFORMATION: TP878 CDRI

<400> SEQUENCE: 116

Gly Ser Ile Phe Ser Ile Asn Ala Met Ala
1               5                   10

<210> SEQ ID NO 117
<211> LENGTH: 14
<212> TYPE: PRT
<213> ORGANISM: Artificial Sequence
<220> FEATURE:
<223> OTHER INFORMATION: TP878 FWII

<400> SEQUENCE: 117

Trp Tyr Arg His Arg Pro Gly Met Gln Arg Glu Arg Val Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: TP878 CDRII

<400> SEQUENCE: 118

Ala Ile Ser Ser Gly Gly Thr
1               5

<210> SEQ ID NO 119
<211> LENGTH: 41
<212> TYPE: PRT
<213> ORGANISM: Artificial Sequence
<220> FEATURE:
<223> OTHER INFORMATION: TP878 FWIII

<400> SEQUENCE: 119

Thr Ser Tyr Ala Asp Ser Val Lys Gly Arg Phe Thr Ile Ser Arg Asp
1               5                   10                  15

Asn Ala Arg Asp Thr Leu Tyr Leu Gln Met Asn Ser Leu Lys Pro Glu
                20                  25                  30

Asp Thr Ala Met Tyr Tyr Cys Ala Ala
            35                  40

<210> SEQ ID NO 120
<211> LENGTH: 11
<212> TYPE: PRT
<213> ORGANISM: Artificial Sequence
<220> FEATURE:
<223> OTHER INFORMATION: TP878 FWIV

<400> SEQUENCE: 120

Trp Gly Lys Gly Thr Leu Val Thr Val Ser Ser
1               5                   10

<210> SEQ ID NO 121
<211> LENGTH: 25
<212> TYPE: PRT
<213> ORGANISM: Artificial Sequence
<220> FEATURE:
<223> OTHER INFORMATION: TP879 FWI

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Val Val Ser
                20                  25

-continued

```
<210> SEQ ID NO 122
<211> LENGTH: 10
<212> TYPE: PRT
<213> ORGANISM: Artificial Sequence
<220> FEATURE:
<223> OTHER INFORMATION: TP879 CDRI

<400> SEQUENCE: 122

Gly Gly Thr Met Asn Ala Tyr Ala Ile Gly
1               5                   10

<210> SEQ ID NO 123
<211> LENGTH: 14
<212> TYPE: PRT
<213> ORGANISM: Artificial Sequence
<220> FEATURE:
<223> OTHER INFORMATION: TP879 FWII

<400> SEQUENCE: 123

Trp Phe Arg Gln Ala Pro Gly Lys Glu Arg Glu Ala Val Ser
1               5                   10

<210> SEQ ID NO 124
<211> LENGTH: 8
<212> TYPE: PRT
<213> ORGANISM: Artificial Sequence
<220> FEATURE:
<223> OTHER INFORMATION: TP879 CDRII

<400> SEQUENCE: 124

Cys Ile Thr Ser Asn Ser Lys Tyr
1               5

<210> SEQ ID NO 125
<211> LENGTH: 41
<212> TYPE: PRT
<213> ORGANISM: Artificial Sequence
<220> FEATURE:
<223> OTHER INFORMATION: TP879 FWIII

<400> SEQUENCE: 125

Thr Asn Tyr Ala Asp Ser Val Lys Gly Arg Phe Thr Ile Ser Arg Asp
1               5                   10                  15

Asn Ala Lys Ser Thr Ala Tyr Leu Gln Met Asn Ser Leu Glu Pro Glu
            20                  25                  30

Asp Thr Ala Val Tyr Tyr Cys Ala Ala
        35                  40

<210> SEQ ID NO 126
<211> LENGTH: 11
<212> TYPE: PRT
<213> ORGANISM: Artificial Sequence
<220> FEATURE:
<223> OTHER INFORMATION: TP879 FWIV

<400> SEQUENCE: 126

Trp Gly Gln Gly Thr Gln Val Thr Val Ser Ser
1               5                   10

<210> SEQ ID NO 127
<211> LENGTH: 25
<212> TYPE: PRT
<213> ORGANISM: Artificial Sequence
<220> FEATURE:
<223> OTHER INFORMATION: TP1104 FWI

<400> SEQUENCE: 127
```

```
Gln Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 128
<211> LENGTH: 10
<212> TYPE: PRT
<213> ORGANISM: Artificial Sequence
<220> FEATURE:
<223> OTHER INFORMATION: TP1104 CDRI

<400> SEQUENCE: 128

Gly Phe Thr Phe Ser Asp Ser Pro Met Thr
1               5                   10

<210> SEQ ID NO 129
<211> LENGTH: 14
<212> TYPE: PRT
<213> ORGANISM: Artificial Sequence
<220> FEATURE:
<223> OTHER INFORMATION: TP1104 FWII

<400> SEQUENCE: 129

Trp Ala Arg Gln Ala Pro Gly Lys Arg Leu Glu Trp Val Ser
1               5                   10

<210> SEQ ID NO 130
<211> LENGTH: 8
<212> TYPE: PRT
<213> ORGANISM: Artificial Sequence
<220> FEATURE:
<223> OTHER INFORMATION: TP1104 CDRII

<400> SEQUENCE: 130

Thr Ile Ser Ser Asp Gly Glu Lys
1               5

<210> SEQ ID NO 131
<211> LENGTH: 41
<212> TYPE: PRT
<213> ORGANISM: Artificial Sequence
<220> FEATURE:
<223> OTHER INFORMATION: TP1104 FWIII

<400> SEQUENCE: 131

Ile Gly Tyr Arg Asp Ala Val Lys Gly Arg Phe Thr Ile Ser Arg Asp
1               5                   10                  15

Asn Ala Lys Asn Thr Leu Tyr Leu Gln Met Asn Ser Leu Lys Pro Glu
            20                  25                  30

Asp Thr Ala Val Tyr Tyr Cys Leu Asn
        35                  40

<210> SEQ ID NO 132
<211> LENGTH: 11
<212> TYPE: PRT
<213> ORGANISM: Artificial Sequence
<220> FEATURE:
<223> OTHER INFORMATION: TP1104 FWIV

<400> SEQUENCE: 132

Phe Ser Asn Gly Thr Leu Val Thr Val Ser Ser
1               5                   10
```

```
<210> SEQ ID NO 133
<211> LENGTH: 25
<212> TYPE: PRT
<213> ORGANISM: Artificial Sequence
<220> FEATURE:
<223> OTHER INFORMATION: TP881 FWI

<400> SEQUENCE: 133

Gln Val Gln Leu Val Glu Ser Gly Gly Gly Leu Val Gln Pro Gly Gly
1               5                   10                  15

Ser Leu Arg Leu Ser Cys Ala Ala Phe
            20                  25

<210> SEQ ID NO 134
<211> LENGTH: 10
<212> TYPE: PRT
<213> ORGANISM: Artificial Sequence
<220> FEATURE:
<223> OTHER INFORMATION: TP881 CDRI

<400> SEQUENCE: 134

Gly Phe Thr Phe Ser Asn Tyr Tyr Met Asn
1               5                   10

<210> SEQ ID NO 135
<211> LENGTH: 14
<212> TYPE: PRT
<213> ORGANISM: Artificial Sequence
<220> FEATURE:
<223> OTHER INFORMATION: TP881 FWII

<400> SEQUENCE: 135

Trp Val Arg Gln Ala Pro Gly Lys Gly Leu Glu Trp Ile Ser
1               5                   10

<210> SEQ ID NO 136
<211> LENGTH: 8
<212> TYPE: PRT
<213> ORGANISM: Artificial Sequence
<220> FEATURE:
<223> OTHER INFORMATION: TP881 CDRII

<400> SEQUENCE: 136

Gly Ile Asn Ser Gly Gly Gly Thr
1               5

<210> SEQ ID NO 137
<211> LENGTH: 41
<212> TYPE: PRT
<213> ORGANISM: Artificial Sequence
<220> FEATURE:
<223> OTHER INFORMATION: TP881 FWIII

<400> SEQUENCE: 137

Thr Ala Tyr Ala Asp Ser Val Lys Gly Arg Phe Thr Ile Ser Arg Asp
1               5                   10                  15

Asn Ala Lys Asn Thr Leu Tyr Leu Gln Met Asn Ser Leu Lys Pro Glu
            20                  25                  30

Asp Thr Ala Val Tyr Tyr Cys Ala Lys
        35                  40

<210> SEQ ID NO 138
<211> LENGTH: 11
<212> TYPE: PRT
<213> ORGANISM: Artificial Sequence
<220> FEATURE:
```

```
<223> OTHER INFORMATION: TP881 FWIV

<400> SEQUENCE: 138

Trp Gly Gln Gly Thr Gln Val Thr Val Ser Ser
1               5                   10

<210> SEQ ID NO 139
<211> LENGTH: 25
<212> TYPE: PRT
<213> ORGANISM: Artificial Sequence
<220> FEATURE:
<223> OTHER INFORMATION: TP882 FWI

<400> SEQUENCE: 139

Gln Val Gln Leu Val Glu Ser Gly Gly Gly Leu Val Gln Pro Gly Gly
1               5                   10                  15

Ser Leu Thr Leu Ser Cys Ala Thr Ser
            20                  25

<210> SEQ ID NO 140
<211> LENGTH: 10
<212> TYPE: PRT
<213> ORGANISM: Artificial Sequence
<220> FEATURE:
<223> OTHER INFORMATION: TP882 CDRI

<400> SEQUENCE: 140

Gly Phe Ser Leu Asp Tyr Tyr Ser Ile Gly
1               5                   10

<210> SEQ ID NO 141
<211> LENGTH: 14
<212> TYPE: PRT
<213> ORGANISM: Artificial Sequence
<220> FEATURE:
<223> OTHER INFORMATION: TP882 FWII

<400> SEQUENCE: 141

Trp Phe Arg Gln Ala Pro Gly Lys Glu Arg Glu Gly Val Ser
1               5                   10

<210> SEQ ID NO 142
<211> LENGTH: 8
<212> TYPE: PRT
<213> ORGANISM: Artificial Sequence
<220> FEATURE:
<223> OTHER INFORMATION: TP882 CDRII

<400> SEQUENCE: 142

Cys Ile Ser Ser Thr Gly Gly Ser
1               5

<210> SEQ ID NO 143
<211> LENGTH: 41
<212> TYPE: PRT
<213> ORGANISM: Artificial Sequence
<220> FEATURE:
<223> OTHER INFORMATION: TP882 FWIII

<400> SEQUENCE: 143

Thr Asn Tyr Val Asp Ser Val Lys Gly Arg Phe Thr Ile Ser Arg Asp
1               5                   10                  15

Asn Ala Lys Asn Thr Val Tyr Leu Gln Met Asn Ser Leu Lys Pro Glu
            20                  25                  30

Asp Thr Gly Val Tyr Tyr Cys Ala Ala
```

```
                    35                        40

<210> SEQ ID NO 144
<211> LENGTH: 11
<212> TYPE: PRT
<213> ORGANISM: Artificial Sequence
<220> FEATURE:
<223> OTHER INFORMATION: TP882 FWIV

<400> SEQUENCE: 144

Trp Gly Lys Gly Thr Leu Val Thr Val Ser Ser
1               5                   10

<210> SEQ ID NO 145
<211> LENGTH: 25
<212> TYPE: PRT
<213> ORGANISM: Artificial Sequence
<220> FEATURE:
<223> OTHER INFORMATION: TP883 FWI

<400> SEQUENCE: 145

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 146
<211> LENGTH: 10
<212> TYPE: PRT
<213> ORGANISM: Artificial Sequence
<220> FEATURE:
<223> OTHER INFORMATION: TP883 CDRI

<400> SEQUENCE: 146

Gly Phe Thr Leu Asp Tyr Tyr Ala Ile Gly
1               5                   10

<210> SEQ ID NO 147
<211> LENGTH: 14
<212> TYPE: PRT
<213> ORGANISM: Artificial Sequence
<220> FEATURE:
<223> OTHER INFORMATION: TP883 FWII

<400> SEQUENCE: 147

Trp Phe Arg Gln Ala Pro Gly Lys Glu Arg Glu Gly Val Ala
1               5                   10

<210> SEQ ID NO 148
<211> LENGTH: 8
<212> TYPE: PRT
<213> ORGANISM: Artificial Sequence
<220> FEATURE:
<223> OTHER INFORMATION: TP883 CDRII

<400> SEQUENCE: 148

Cys Ile Thr Ser Ser Glu Gly Ser
1               5

<210> SEQ ID NO 149
<211> LENGTH: 41
<212> TYPE: PRT
<213> ORGANISM: Artificial Sequence
<220> FEATURE:
<223> OTHER INFORMATION: TP883 FWIII

<400> SEQUENCE: 149
```

```
Thr Tyr Tyr Ala Asp Ser Val Lys Gly Arg Phe Thr Ile Ser Arg Asp
1               5                   10                  15

Asn Ala Lys Asn Thr Val Tyr Leu Gln Met Asn Ser Leu Lys Pro Glu
            20                  25                  30

Asp Thr Ala Val Tyr Tyr Cys Ala Ala
        35                  40

<210> SEQ ID NO 150
<211> LENGTH: 11
<212> TYPE: PRT
<213> ORGANISM: Artificial Sequence
<220> FEATURE:
<223> OTHER INFORMATION: TP883 FWIV

<400> SEQUENCE: 150

Ser Gly Gln Gly Thr Gln Val Thr Val Ser Ser
1               5                   10

<210> SEQ ID NO 151
<211> LENGTH: 25
<212> TYPE: PRT
<213> ORGANISM: Artificial Sequence
<220> FEATURE:
<223> OTHER INFORMATION: TP884 FWI

<400> SEQUENCE: 151

Gln Val Gln Leu Val Glu Ser Gly Gly Gly Leu Val Gln Pro Gly Gly
1               5                   10                  15

Ser Leu Thr Leu Ser Cys Val Ile Ser
            20                  25

<210> SEQ ID NO 152
<211> LENGTH: 10
<212> TYPE: PRT
<213> ORGANISM: Artificial Sequence
<220> FEATURE:
<223> OTHER INFORMATION: TP884 CDRI

<400> SEQUENCE: 152

Gly Phe Arg Met Asp Ile Ala Thr Met Ser
1               5                   10

<210> SEQ ID NO 153
<211> LENGTH: 14
<212> TYPE: PRT
<213> ORGANISM: Artificial Sequence
<220> FEATURE:
<223> OTHER INFORMATION: TP884 FWII

<400> SEQUENCE: 153

Trp Val Arg Gln Ala Pro Gly Lys Gly Leu Glu Trp Val Ala
1               5                   10

<210> SEQ ID NO 154
<211> LENGTH: 8
<212> TYPE: PRT
<213> ORGANISM: Artificial Sequence
<220> FEATURE:
<223> OTHER INFORMATION: TP884 CDRII

<400> SEQUENCE: 154

Gly Ile Ile Asn Tyr Arg Asn Phe
1               5
```

```
<210> SEQ ID NO 155
<211> LENGTH: 41
<212> TYPE: PRT
<213> ORGANISM: Artificial Sequence
<220> FEATURE:
<223> OTHER INFORMATION: TP884 FWIII

<400> SEQUENCE: 155

Thr Trp Tyr Ser Asp Ser Val Lys Gly Arg Phe Thr Ile Ser Thr Asp
1               5                   10                  15

Thr Ala Lys Ser Glu Val Tyr Leu Gln Met Asn Ser Leu Lys Ser Glu
            20                  25                  30

Asp Thr Ala Val Tyr Tyr Cys Ala His
        35                  40

<210> SEQ ID NO 156
<211> LENGTH: 11
<212> TYPE: PRT
<213> ORGANISM: Artificial Sequence
<220> FEATURE:
<223> OTHER INFORMATION: TP884 FWIV

<400> SEQUENCE: 156

Arg Gly Gln Gly Thr Gln Val Thr Val Ser Ser
1               5                   10

<210> SEQ ID NO 157
<211> LENGTH: 25
<212> TYPE: PRT
<213> ORGANISM: Artificial Sequence
<220> FEATURE:
<223> OTHER INFORMATION: TP894 FWI

<400> SEQUENCE: 157

Gln Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 158
<211> LENGTH: 10
<212> TYPE: PRT
<213> ORGANISM: Artificial Sequence
<220> FEATURE:
<223> OTHER INFORMATION: TP894 CDRI

<400> SEQUENCE: 158

Gly Leu Thr Leu Asp Phe Lys Gly Ile Gly
1               5                   10

<210> SEQ ID NO 159
<211> LENGTH: 14
<212> TYPE: PRT
<213> ORGANISM: Artificial Sequence
<220> FEATURE:
<223> OTHER INFORMATION: TP894 FWII

<400> SEQUENCE: 159

Trp Phe Arg Gln Ala Pro Gly Lys Glu Arg Glu Gly Val Ser
1               5                   10

<210> SEQ ID NO 160
<211> LENGTH: 8
<212> TYPE: PRT
<213> ORGANISM: Artificial Sequence
<220> FEATURE:
```

<223> OTHER INFORMATION: TP894 CDRII

<400> SEQUENCE: 160

Cys Ile Asn Pro Ser Asp Ser Ser
1                   5

<210> SEQ ID NO 161
<211> LENGTH: 41
<212> TYPE: PRT
<213> ORGANISM: Artificial Sequence
<220> FEATURE:
<223> OTHER INFORMATION: TP894 FWIII

<400> SEQUENCE: 161

Ala Ala Tyr Ala Asp Ser Val Lys Gly Arg Phe Thr Ile Ser Arg Asp
1                   5                   10                  15

Asn Ala Lys Asn Thr Val Tyr Leu Gln Met Asn Asn Leu Gln Pro Glu
                20                  25                  30

Asp Thr Ala Val Tyr Tyr Cys Val Ala
        35                  40

<210> SEQ ID NO 162
<211> LENGTH: 11
<212> TYPE: PRT
<213> ORGANISM: Artificial Sequence
<220> FEATURE:
<223> OTHER INFORMATION: TP894 FWIV

<400> SEQUENCE: 162

Trp Gly Lys Gly Thr Leu Val Thr Val Ser Ser
1                   5                   10

<210> SEQ ID NO 163
<211> LENGTH: 25
<212> TYPE: PRT
<213> ORGANISM: Artificial Sequence
<220> FEATURE:
<223> OTHER INFORMATION: TP895 FWI

<400> SEQUENCE: 163

Gln Val Gln Leu Val Glu Ser Gly Gly Gly Leu Val Gln Pro Gly Gly
1                   5                   10                  15

Ser Leu Arg Leu Ser Cys Ala Ala Ser
            20                  25

<210> SEQ ID NO 164
<211> LENGTH: 10
<212> TYPE: PRT
<213> ORGANISM: Artificial Sequence
<220> FEATURE:
<223> OTHER INFORMATION: TP895 CDRI

<400> SEQUENCE: 164

Gly Phe Thr Leu Asp Tyr Tyr Ala Ile Gly
1                   5                   10

<210> SEQ ID NO 165
<211> LENGTH: 14
<212> TYPE: PRT
<213> ORGANISM: Artificial Sequence
<220> FEATURE:
<223> OTHER INFORMATION: TP895 FWII

<400> SEQUENCE: 165

Trp Phe Arg Gln Ala Pro Gly Lys Glu His Glu Gly Val Ser

```
1               5                    10

<210> SEQ ID NO 166
<211> LENGTH: 8
<212> TYPE: PRT
<213> ORGANISM: Artificial Sequence
<220> FEATURE:
<223> OTHER INFORMATION: TP895 CDRII

<400> SEQUENCE: 166

Cys Ile Ser Pro Ser Gly Gly Ser
1               5

<210> SEQ ID NO 167
<211> LENGTH: 41
<212> TYPE: PRT
<213> ORGANISM: Artificial Sequence
<220> FEATURE:
<223> OTHER INFORMATION: TP895 FWIII

<400> SEQUENCE: 167

Thr Asn Tyr Ala Asp Ser Val Lys Gly Arg Phe Thr Ile Ser Arg Asp
1               5                    10                   15

Asn Ala Lys Asn Thr Val Tyr Leu Gln Met Asn Ser Leu Lys Pro Glu
            20                   25                   30

Asp Thr Ala Val Tyr Ser Cys Val Ala
        35                   40

<210> SEQ ID NO 168
<211> LENGTH: 11
<212> TYPE: PRT
<213> ORGANISM: Artificial Sequence
<220> FEATURE:
<223> OTHER INFORMATION: TP895 FWIV

<400> SEQUENCE: 168

Trp Gly Lys Gly Thr Gln Val Thr Val Ser Ser
1               5                    10

<210> SEQ ID NO 169
<211> LENGTH: 25
<212> TYPE: PRT
<213> ORGANISM: Artificial Sequence
<220> FEATURE:
<223> OTHER INFORMATION: TP885 FWI

<400> SEQUENCE: 169

Gln Val Gln Leu Val Glu Ser Gly Gly Gly Leu Val Gln Ala Gly Gly
1               5                    10                   15

Ser Val Arg Leu Ser Cys Ala Ala Ser
            20                   25

<210> SEQ ID NO 170
<211> LENGTH: 10
<212> TYPE: PRT
<213> ORGANISM: Artificial Sequence
<220> FEATURE:
<223> OTHER INFORMATION: TP885 CDRI

<400> SEQUENCE: 170

Gly Phe Thr Phe Ser Ser Tyr Tyr Met Thr
1               5                    10

<210> SEQ ID NO 171
<211> LENGTH: 14
```

```
<212> TYPE: PRT
<213> ORGANISM: Artificial Sequence
<220> FEATURE:
<223> OTHER INFORMATION: TP885 FWII

<400> SEQUENCE: 171

Trp Val Arg Gln Ala Pro Gly Lys Gly Pro Glu Trp Val Ser
1               5                   10

<210> SEQ ID NO 172
<211> LENGTH: 8
<212> TYPE: PRT
<213> ORGANISM: Artificial Sequence
<220> FEATURE:
<223> OTHER INFORMATION: TP885 CDRII

<400> SEQUENCE: 172

Ala Ile Asn Thr Gly Gly Asp Ala
1               5

<210> SEQ ID NO 173
<211> LENGTH: 41
<212> TYPE: PRT
<213> ORGANISM: Artificial Sequence
<220> FEATURE:
<223> OTHER INFORMATION: TP885 FWIII

<400> SEQUENCE: 173

Thr Arg Tyr Ala Glu Ser Val Lys Gly Arg Phe Thr Ile Ser Arg Asp
1               5                   10                  15

Asn Ala Lys Asn Met Leu Tyr Leu Gln Met Asn Ser Leu Lys Pro Glu
            20                  25                  30

Asp Thr Ala Leu Tyr Tyr Cys Gly Arg
        35                  40

<210> SEQ ID NO 174
<211> LENGTH: 11
<212> TYPE: PRT
<213> ORGANISM: Artificial Sequence
<220> FEATURE:
<223> OTHER INFORMATION: TP885 FWIV

<400> SEQUENCE: 174

Arg Gly Gln Gly Thr Leu Val Thr Val Ser Ser
1               5                   10

<210> SEQ ID NO 175
<211> LENGTH: 25
<212> TYPE: PRT
<213> ORGANISM: Artificial Sequence
<220> FEATURE:
<223> OTHER INFORMATION: TP886 FWI

<400> SEQUENCE: 175

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 176
<211> LENGTH: 10
<212> TYPE: PRT
<213> ORGANISM: Artificial Sequence
<220> FEATURE:
<223> OTHER INFORMATION: TP886 CDRI
```

-continued

<400> SEQUENCE: 176

Gly Phe Thr Phe Ala Asn Tyr Tyr Met Ser
1               5                   10

<210> SEQ ID NO 177
<211> LENGTH: 14
<212> TYPE: PRT
<213> ORGANISM: Artificial Sequence
<220> FEATURE:
<223> OTHER INFORMATION: TP886 FWII

<400> SEQUENCE: 177

Trp Val Arg Gln Ala Pro Gly Lys Gly Pro Glu Trp Val Ser
1               5                   10

<210> SEQ ID NO 178
<211> LENGTH: 8
<212> TYPE: PRT
<213> ORGANISM: Artificial Sequence
<220> FEATURE:
<223> OTHER INFORMATION: TP886 CDRII

<400> SEQUENCE: 178

Ala Ile Asn Thr Leu Gly Gly Lys
1               5

<210> SEQ ID NO 179
<211> LENGTH: 41
<212> TYPE: PRT
<213> ORGANISM: Artificial Sequence
<220> FEATURE:
<223> OTHER INFORMATION: TP886 FWIII

<400> SEQUENCE: 179

Thr Lys Tyr Ala Asp Ser Val Lys Gly Arg Phe Thr Ile Ser Arg Asp
1               5                   10                  15

Asn Ala Lys Ser Thr Leu Tyr Leu Gln Met Asn Ser Leu Lys Pro Glu
            20                  25                  30

Asp Thr Ala Leu Tyr Tyr Cys Ala Arg
        35                  40

<210> SEQ ID NO 180
<211> LENGTH: 11
<212> TYPE: PRT
<213> ORGANISM: Artificial Sequence
<220> FEATURE:
<223> OTHER INFORMATION: TP886 FWIV

<400> SEQUENCE: 180

Arg Gly Gln Gly Thr Gln Val Thr Val Ser Ser
1               5                   10

<210> SEQ ID NO 181
<211> LENGTH: 25
<212> TYPE: PRT
<213> ORGANISM: Artificial Sequence
<220> FEATURE:
<223> OTHER INFORMATION: TP887 FWI

<400> SEQUENCE: 181

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

```
<210> SEQ ID NO 182
<211> LENGTH: 10
<212> TYPE: PRT
<213> ORGANISM: Artificial Sequence
<220> FEATURE:
<223> OTHER INFORMATION: TP887 CDRI

<400> SEQUENCE: 182

Gly Arg Thr Phe Ser Thr Tyr Ile Met Gly
1               5                   10

<210> SEQ ID NO 183
<211> LENGTH: 14
<212> TYPE: PRT
<213> ORGANISM: Artificial Sequence
<220> FEATURE:
<223> OTHER INFORMATION: TP887 FWII

<400> SEQUENCE: 183

Trp Phe Arg Gln Ala Pro Gly Lys Glu Arg Glu Phe Val Ala
1               5                   10

<210> SEQ ID NO 184
<211> LENGTH: 8
<212> TYPE: PRT
<213> ORGANISM: Artificial Sequence
<220> FEATURE:
<223> OTHER INFORMATION: TP887 CDRII

<400> SEQUENCE: 184

Ala Ile Thr Trp Ile Gly Gly Ser
1               5

<210> SEQ ID NO 185
<211> LENGTH: 41
<212> TYPE: PRT
<213> ORGANISM: Artificial Sequence
<220> FEATURE:
<223> OTHER INFORMATION: TP887 FWIII

<400> SEQUENCE: 185

Thr Tyr Tyr Ala Asp Ser Val Lys Gly Arg Phe Thr Ile Ser Arg Asp
1               5                   10                  15

Tyr Ala Lys Asn Thr Leu Tyr Leu Gln Met Asn Ser Leu Lys Pro Glu
            20                  25                  30

Asp Thr Ala Val Tyr Tyr Cys Ala Ala
        35                  40

<210> SEQ ID NO 186
<211> LENGTH: 11
<212> TYPE: PRT
<213> ORGANISM: Artificial Sequence
<220> FEATURE:
<223> OTHER INFORMATION: TP887 FWIV

<400> SEQUENCE: 186

Trp Gly Gln Gly Thr Gln Val Thr Val Ser Ser
1               5                   10

<210> SEQ ID NO 187
<211> LENGTH: 25
<212> TYPE: PRT
<213> ORGANISM: Artificial Sequence
<220> FEATURE:
<223> OTHER INFORMATION: TP888 FWI
```

-continued

```
<400> SEQUENCE: 187

Gln Val Gln Leu Val Glu Ser Gly Gly Gly Leu Val Gln Asp Gly Gly
1               5                   10                  15

Ser Leu Arg Leu Ser Cys Ala Ala Ser
            20                  25

<210> SEQ ID NO 188
<211> LENGTH: 10
<212> TYPE: PRT
<213> ORGANISM: Artificial Sequence
<220> FEATURE:
<223> OTHER INFORMATION: TP888 CDRI

<400> SEQUENCE: 188

Gly Arg Thr Phe Ser Val Tyr Ala Met Gly
1               5                   10

<210> SEQ ID NO 189
<211> LENGTH: 14
<212> TYPE: PRT
<213> ORGANISM: Artificial Sequence
<220> FEATURE:
<223> OTHER INFORMATION: TP888 FWII

<400> SEQUENCE: 189

Trp Phe Arg Gln Ala Pro Gly Lys Glu Arg Glu Phe Val Ala
1               5                   10

<210> SEQ ID NO 190
<211> LENGTH: 8
<212> TYPE: PRT
<213> ORGANISM: Artificial Sequence
<220> FEATURE:
<223> OTHER INFORMATION: TP888 CDRII

<400> SEQUENCE: 190

Ala Ile Ser Trp Ile Gly Gly Ser
1               5

<210> SEQ ID NO 191
<211> LENGTH: 41
<212> TYPE: PRT
<213> ORGANISM: Artificial Sequence
<220> FEATURE:
<223> OTHER INFORMATION: TP888 FWIII

<400> SEQUENCE: 191

Thr Tyr Ser Ala Asp Ser Val Lys Gly Arg Phe Thr Ile Ser Arg Glu
1               5                   10                  15

Tyr Ala Lys Asn Thr Leu Tyr Leu Gln Met Asn Ser Leu Arg Pro Glu
            20                  25                  30

Asp Thr Ala Val Tyr Tyr Cys Ala Ala
        35                  40

<210> SEQ ID NO 192
<211> LENGTH: 11
<212> TYPE: PRT
<213> ORGANISM: Artificial Sequence
<220> FEATURE:
<223> OTHER INFORMATION: TP888 FWIV

<400> SEQUENCE: 192

Trp Gly Gln Gly Thr Gln Val Thr Val Ser Ser
1               5                   10
```

-continued

```
<210> SEQ ID NO 193
<211> LENGTH: 25
<212> TYPE: PRT
<213> ORGANISM: Artificial Sequence
<220> FEATURE:
<223> OTHER INFORMATION: TP889 FWI

<400> SEQUENCE: 193

Gln Val Gln Leu Val Glu Ser Gly Gly Gly Leu Val Gln Ala Gly Asp
1               5                   10                  15

Ser Leu Arg Leu Ser Cys Thr Ala Ser
            20                  25

<210> SEQ ID NO 194
<211> LENGTH: 10
<212> TYPE: PRT
<213> ORGANISM: Artificial Sequence
<220> FEATURE:
<223> OTHER INFORMATION: TP889 CDRI

<400> SEQUENCE: 194

Gly Arg Thr Phe Ser Thr Tyr Ala Met Gly
1               5                   10

<210> SEQ ID NO 195
<211> LENGTH: 14
<212> TYPE: PRT
<213> ORGANISM: Artificial Sequence
<220> FEATURE:
<223> OTHER INFORMATION: TP889 FWII

<400> SEQUENCE: 195

Trp Phe Arg Gln Ala Pro Gly Lys Glu Arg Glu Phe Val Ala
1               5                   10

<210> SEQ ID NO 196
<211> LENGTH: 8
<212> TYPE: PRT
<213> ORGANISM: Artificial Sequence
<220> FEATURE:
<223> OTHER INFORMATION: TP889 CDRII

<400> SEQUENCE: 196

Ala Ile Ser Trp Ile Gly Gly Ser
1               5

<210> SEQ ID NO 197
<211> LENGTH: 41
<212> TYPE: PRT
<213> ORGANISM: Artificial Sequence
<220> FEATURE:
<223> OTHER INFORMATION: TP889 FWIII

<400> SEQUENCE: 197

Thr Tyr Tyr Ala Asp Ser Val Lys Gly Arg Phe Thr Ile Ser Arg Asp
1               5                   10                  15

Tyr Ala Glu Asn Thr Leu Tyr Leu Gln Met Asn Ser Leu Lys Pro Glu
            20                  25                  30

Asp Thr Ala Val Tyr Tyr Cys Ala Ala
        35                  40

<210> SEQ ID NO 198
<211> LENGTH: 11
<212> TYPE: PRT
<213> ORGANISM: Artificial Sequence
```

-continued

```
<220> FEATURE:
<223> OTHER INFORMATION: TP889 FWIV

<400> SEQUENCE: 198

Trp Gly Gln Gly Thr Leu Val Thr Val Ser Ser
1               5                   10

<210> SEQ ID NO 199
<211> LENGTH: 25
<212> TYPE: PRT
<213> ORGANISM: Artificial Sequence
<220> FEATURE:
<223> OTHER INFORMATION: TP890 FWI

<400> SEQUENCE: 199

Gln Val Gln Leu Val Glu Ser Gly Gly Glu Ala Val Gln Thr Gly Gly
1               5                   10                  15

Ser Leu Arg Leu Ser Cys Ala Ala Ser
            20                  25

<210> SEQ ID NO 200
<211> LENGTH: 10
<212> TYPE: PRT
<213> ORGANISM: Artificial Sequence
<220> FEATURE:
<223> OTHER INFORMATION: TP890 CDRI

<400> SEQUENCE: 200

Gly Arg Thr Phe Ser Thr Tyr Leu Met Gly
1               5                   10

<210> SEQ ID NO 201
<211> LENGTH: 14
<212> TYPE: PRT
<213> ORGANISM: Artificial Sequence
<220> FEATURE:
<223> OTHER INFORMATION: TP890 FWII

<400> SEQUENCE: 201

Trp Phe Arg Gln Ala Pro Gly Lys Glu Arg Glu Phe Val Ala
1               5                   10

<210> SEQ ID NO 202
<211> LENGTH: 8
<212> TYPE: PRT
<213> ORGANISM: Artificial Sequence
<220> FEATURE:
<223> OTHER INFORMATION: TP890 CDRII

<400> SEQUENCE: 202

Ala Ile Ser Trp Ile Gly Gly Ser
1               5

<210> SEQ ID NO 203
<211> LENGTH: 41
<212> TYPE: PRT
<213> ORGANISM: Artificial Sequence
<220> FEATURE:
<223> OTHER INFORMATION: TP890 FWIII

<400> SEQUENCE: 203

Thr Tyr Tyr Ala Asp Ser Val Lys Gly Arg Phe Thr Ile Ser Arg Asp
1               5                   10                  15

Tyr Ala Glu Asn Thr Leu Tyr Leu Gln Met Asn Ser Leu Lys Pro Glu
            20                  25                  30
```

-continued

```
Asp Thr Ala Val Tyr Tyr Cys Ala Ala
        35                  40

<210> SEQ ID NO 204
<211> LENGTH: 11
<212> TYPE: PRT
<213> ORGANISM: Artificial Sequence
<220> FEATURE:
<223> OTHER INFORMATION: TP890 FWIV

<400> SEQUENCE: 204

Trp Gly Gln Gly Thr Gln Val Thr Val Ser Ser
1               5                   10

<210> SEQ ID NO 205
<211> LENGTH: 25
<212> TYPE: PRT
<213> ORGANISM: Artificial Sequence
<220> FEATURE:
<223> OTHER INFORMATION: TP1106 FWI

<400> SEQUENCE: 205

Gln Val Gln Leu Val Glu Ser Gly Gly Gly Leu Val Gln Pro Gly Gly
1               5                   10                  15

Ser Leu Arg Leu Tyr Cys Ala Ala Ser
            20                  25

<210> SEQ ID NO 206
<211> LENGTH: 10
<212> TYPE: PRT
<213> ORGANISM: Artificial Sequence
<220> FEATURE:
<223> OTHER INFORMATION: TP1106 CDRI

<400> SEQUENCE: 206

Gly Arg Thr Asp Thr Thr Tyr Ala Leu Gly
1               5                   10

<210> SEQ ID NO 207
<211> LENGTH: 14
<212> TYPE: PRT
<213> ORGANISM: Artificial Sequence
<220> FEATURE:
<223> OTHER INFORMATION: TP1106 FWII

<400> SEQUENCE: 207

Trp Phe Arg Gln Pro Pro Gly Lys Glu Arg Gln Phe Val Ala
1               5                   10

<210> SEQ ID NO 208
<211> LENGTH: 8
<212> TYPE: PRT
<213> ORGANISM: Artificial Sequence
<220> FEATURE:
<223> OTHER INFORMATION: TP1106 CDRII

<400> SEQUENCE: 208

Ser Ile Thr Trp Ile Gly Gly Ala
1               5

<210> SEQ ID NO 209
<211> LENGTH: 41
<212> TYPE: PRT
<213> ORGANISM: Artificial Sequence
<220> FEATURE:
<223> OTHER INFORMATION: TP1106 FWIII
```

```
<400> SEQUENCE: 209

Thr Asn Tyr Ala Ala Ser Val Lys Gly Arg Phe Thr Ile Ser Lys Asp
1               5                   10                  15

Leu Gly Thr Asn Thr Phe Asn Leu Gln Met Asn Ser Leu Thr Pro Asp
            20                  25                  30

Asp Thr Ala Val Tyr Tyr Cys Ala Ala
        35                  40

<210> SEQ ID NO 210
<211> LENGTH: 11
<212> TYPE: PRT
<213> ORGANISM: Artificial Sequence
<220> FEATURE:
<223> OTHER INFORMATION: TP1106 FWIV

<400> SEQUENCE: 210

Trp Gly Gln Gly Thr Gln Val Thr Val Ser Ser
1               5                   10

<210> SEQ ID NO 211
<211> LENGTH: 25
<212> TYPE: PRT
<213> ORGANISM: Artificial Sequence
<220> FEATURE:
<223> OTHER INFORMATION: TP1129 FWI

<400> SEQUENCE: 211

Gln Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 212
<211> LENGTH: 10
<212> TYPE: PRT
<213> ORGANISM: Artificial Sequence
<220> FEATURE:
<223> OTHER INFORMATION: TP1129 CDRI

<400> SEQUENCE: 212

Gly Phe Thr Phe Ser Ser Ala Tyr Met Ser
1               5                   10

<210> SEQ ID NO 213
<211> LENGTH: 14
<212> TYPE: PRT
<213> ORGANISM: Artificial Sequence
<220> FEATURE:
<223> OTHER INFORMATION: TP1129 FWII

<400> SEQUENCE: 213

Trp Val Arg Gln Ala Pro Gly Lys Gly Pro Glu Trp Val Ser
1               5                   10

<210> SEQ ID NO 214
<211> LENGTH: 8
<212> TYPE: PRT
<213> ORGANISM: Artificial Sequence
<220> FEATURE:
<223> OTHER INFORMATION: TP1129 CDRII

<400> SEQUENCE: 214

Thr Ile Ser Thr Gly Gly Gly Ile
1               5
```

-continued

<210> SEQ ID NO 215
<211> LENGTH: 41
<212> TYPE: PRT
<213> ORGANISM: Artificial Sequence
<220> FEATURE:
<223> OTHER INFORMATION: TP1129 FWIII

<400> SEQUENCE: 215

Val Asn Tyr Ala Asp Ser Val Lys Gly Arg Phe Ala Ile Ser Arg Asp
1               5                   10                  15

Asn Ala Lys Asn Thr Leu Tyr Leu Gln Met Asn Lys Leu Lys Pro Glu
            20                  25                  30

Asp Thr Ala Leu Tyr Tyr Cys Ala Ser
        35                  40

<210> SEQ ID NO 216
<211> LENGTH: 11
<212> TYPE: PRT
<213> ORGANISM: Artificial Sequence
<220> FEATURE:
<223> OTHER INFORMATION: TP1129 FWIV

<400> SEQUENCE: 216

Trp Gly Gln Gly Thr Leu Val Thr Val Ser Ser
1               5                   10

<210> SEQ ID NO 217
<211> LENGTH: 25
<212> TYPE: PRT
<213> ORGANISM: Artificial Sequence
<220> FEATURE:
<223> OTHER INFORMATION: TP921 FWI

<400> SEQUENCE: 217

Gln Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 218
<211> LENGTH: 10
<212> TYPE: PRT
<213> ORGANISM: Artificial Sequence
<220> FEATURE:
<223> OTHER INFORMATION: TP921 CDRI

<400> SEQUENCE: 218

Gly Phe Thr Phe Ser Ser Ala Tyr Met Ser
1               5                   10

<210> SEQ ID NO 219
<211> LENGTH: 14
<212> TYPE: PRT
<213> ORGANISM: Artificial Sequence
<220> FEATURE:
<223> OTHER INFORMATION: TP921 FWII

<400> SEQUENCE: 219

Trp Val Arg Gln Ala Pro Gly Lys Gly Pro Glu Trp Val Ser
1               5                   10

<210> SEQ ID NO 220
<211> LENGTH: 8
<212> TYPE: PRT
<213> ORGANISM: Artificial Sequence -continued

```
<220> FEATURE:
<223> OTHER INFORMATION: TP921 CDRII

<400> SEQUENCE: 220

Thr Ile Ser Thr Gly Gly Gly Ile
1               5

<210> SEQ ID NO 221
<211> LENGTH: 41
<212> TYPE: PRT
<213> ORGANISM: Artificial Sequence
<220> FEATURE:
<223> OTHER INFORMATION: TP921 FWIII

<400> SEQUENCE: 221

Val Asn Tyr Ala Asp Ser Val Lys Gly Arg Phe Thr Ile Ser Arg Asp
1               5                   10                  15

Asn Ala Lys Asn Thr Leu Tyr Leu Gln Met Asn Lys Leu Lys Pro Glu
            20                  25                  30

Asp Thr Ala Leu Tyr Tyr Cys Ala Ser
        35                  40

<210> SEQ ID NO 222
<211> LENGTH: 18
<212> TYPE: PRT
<213> ORGANISM: Artificial Sequence
<220> FEATURE:
<223> OTHER INFORMATION: TP921 CDRIII

<400> SEQUENCE: 222

Asn Lys Gly Pro His Tyr Tyr Ser Asp Tyr Phe Asp Ser Asn Gln Tyr
1               5                   10                  15

Asp Phe

<210> SEQ ID NO 223
<211> LENGTH: 11
<212> TYPE: PRT
<213> ORGANISM: Artificial Sequence
<220> FEATURE:
<223> OTHER INFORMATION: TP921 FWIV

<400> SEQUENCE: 223

Trp Gly Gln Gly Thr Gln Val Thr Val Ser Ser
1               5                   10

<210> SEQ ID NO 224
<211> LENGTH: 25
<212> TYPE: PRT
<213> ORGANISM: Artificial Sequence
<220> FEATURE:
<223> OTHER INFORMATION: TP922 FWI

<400> SEQUENCE: 224

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 225
<211> LENGTH: 10
<212> TYPE: PRT
<213> ORGANISM: Artificial Sequence
<220> FEATURE:
<223> OTHER INFORMATION: TP922 CDRI
```

```
<400> SEQUENCE: 225

Gly Phe Thr Phe Ser Ser Tyr Tyr Met Ser
1               5                   10

<210> SEQ ID NO 226
<211> LENGTH: 14
<212> TYPE: PRT
<213> ORGANISM: Artificial Sequence
<220> FEATURE:
<223> OTHER INFORMATION: TP922 FWII

<400> SEQUENCE: 226

Trp Val Arg Gln Ala Pro Gly Lys Gly Leu Glu Trp Val Ser
1               5                   10

<210> SEQ ID NO 227
<211> LENGTH: 8
<212> TYPE: PRT
<213> ORGANISM: Artificial Sequence
<220> FEATURE:
<223> OTHER INFORMATION: TP922 CDRII

<400> SEQUENCE: 227

Asp Ile Ser Thr Asp Gly Gly Arg
1               5

<210> SEQ ID NO 228
<211> LENGTH: 41
<212> TYPE: PRT
<213> ORGANISM: Artificial Sequence
<220> FEATURE:
<223> OTHER INFORMATION: TP922 FWIII

<400> SEQUENCE: 228

Thr Leu Tyr Ala Asp Ser Val Lys Gly Arg Phe Thr Ile Ser Arg Asp
1               5                   10                  15

Asn Ala Lys Asn Thr Leu Tyr Leu Gln Met Asn Ser Leu Lys Pro Glu
            20                  25                  30

Asp Thr Ala Leu Tyr Phe Cys Ala Arg
        35                  40

<210> SEQ ID NO 229
<211> LENGTH: 11
<212> TYPE: PRT
<213> ORGANISM: Artificial Sequence
<220> FEATURE:
<223> OTHER INFORMATION: TP922 FWIV

<400> SEQUENCE: 229

Trp Gly Lys Gly Thr Leu Val Thr Val Ser Ser
1               5                   10

<210> SEQ ID NO 230
<211> LENGTH: 25
<212> TYPE: PRT
<213> ORGANISM: Artificial Sequence
<220> FEATURE:
<223> OTHER INFORMATION: TP923 FWI

<400> SEQUENCE: 230

Gln Val Gln Leu Val Glu Ser Gly Gly Gly Leu Val Gln Pro Gly Glu
1               5                   10                  15

Ser Leu Thr Leu Ser Cys Ala Ala Ser
            20                  25
```

```
<210> SEQ ID NO 231
<211> LENGTH: 10
<212> TYPE: PRT
<213> ORGANISM: Artificial Sequence
<220> FEATURE:
<223> OTHER INFORMATION: TP923 CDRI

<400> SEQUENCE: 231

Gly Phe Thr Phe Ser Asn Val Ala Met Ser
1               5                   10

<210> SEQ ID NO 232
<211> LENGTH: 14
<212> TYPE: PRT
<213> ORGANISM: Artificial Sequence
<220> FEATURE:
<223> OTHER INFORMATION: TP923 FWII

<400> SEQUENCE: 232

Trp Val Arg Gln Ala Pro Arg Lys Gly Leu Glu Trp Val Ser
1               5                   10

<210> SEQ ID NO 233
<211> LENGTH: 8
<212> TYPE: PRT
<213> ORGANISM: Artificial Sequence
<220> FEATURE:
<223> OTHER INFORMATION: TP923 CDRII

<400> SEQUENCE: 233

Ser Ile Ser Ser Asp Gly Gly Arg
1               5

<210> SEQ ID NO 234
<211> LENGTH: 41
<212> TYPE: PRT
<213> ORGANISM: Artificial Sequence
<220> FEATURE:
<223> OTHER INFORMATION: TP923 FWIII

<400> SEQUENCE: 234

Thr Leu Tyr Ala Ala Ser Val Lys Gly Arg Phe Thr Val Ser Arg Asp
1               5                   10                  15

Asn Ala Lys Asn Thr Leu Thr Leu Gln Met Asp Ser Leu Lys Ala Glu
            20                  25                  30

Asp Thr Ala Val Tyr Tyr Cys Thr Glu
        35                  40

<210> SEQ ID NO 235
<211> LENGTH: 11
<212> TYPE: PRT
<213> ORGANISM: Artificial Sequence
<220> FEATURE:
<223> OTHER INFORMATION: TP923 FWIV

<400> SEQUENCE: 235

Arg Gly Gln Gly Thr Gln Val Thr Val Ser Ser
1               5                   10

<210> SEQ ID NO 236
<211> LENGTH: 25
<212> TYPE: PRT
<213> ORGANISM: Artificial Sequence
<220> FEATURE:
<223> OTHER INFORMATION: TP926 FWI
```

-continued

```
<400> SEQUENCE: 236

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 237
<211> LENGTH: 10
<212> TYPE: PRT
<213> ORGANISM: Artificial Sequence
<220> FEATURE:
<223> OTHER INFORMATION: TP926 CDRI

<400> SEQUENCE: 237

Glu Thr Ile Phe Ser Ile Asn Val Met Gly
1               5                   10

<210> SEQ ID NO 238
<211> LENGTH: 14
<212> TYPE: PRT
<213> ORGANISM: Artificial Sequence
<220> FEATURE:
<223> OTHER INFORMATION: TP926 FWII

<400> SEQUENCE: 238

Trp Phe Arg Gln Ala Pro Gly Lys Glu Arg Glu Leu Val Ala
1               5                   10

<210> SEQ ID NO 239
<211> LENGTH: 7
<212> TYPE: PRT
<213> ORGANISM: Artificial Sequence
<220> FEATURE:
<223> OTHER INFORMATION: TP926 CDRII

<400> SEQUENCE: 239

Lys Ile Ser Ser Val Gly Ser
1               5

<210> SEQ ID NO 240
<211> LENGTH: 41
<212> TYPE: PRT
<213> ORGANISM: Artificial Sequence
<220> FEATURE:
<223> OTHER INFORMATION: TP926 FWIII

<400> SEQUENCE: 240

Thr Tyr Tyr Ala Asp Pro Val Lys Gly Arg Phe Thr Ile Ser Arg Asp
1               5                   10                  15

Asp Thr Lys Asn Thr Leu Ser Leu Gln Met Asn Ser Leu Lys Pro Glu
            20                  25                  30

Asp Thr Ala Met Tyr Tyr Cys Ala Ala
        35                  40

<210> SEQ ID NO 241
<211> LENGTH: 11
<212> TYPE: PRT
<213> ORGANISM: Artificial Sequence
<220> FEATURE:
<223> OTHER INFORMATION: TP926 FWIV

<400> SEQUENCE: 241

Trp Gly Gln Gly Thr Gln Val Thr Val Ser Ser
1               5                   10
```

-continued

```
<210> SEQ ID NO 242
<211> LENGTH: 25
<212> TYPE: PRT
<213> ORGANISM: Artificial Sequence
<220> FEATURE:
<223> OTHER INFORMATION: TP925 FWI

<400> SEQUENCE: 242

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 243
<211> LENGTH: 10
<212> TYPE: PRT
<213> ORGANISM: Artificial Sequence
<220> FEATURE:
<223> OTHER INFORMATION: TP925 CDRI

<400> SEQUENCE: 243

Gly Phe Thr Leu Asp Ser Tyr Gly Ile Gly
1               5                   10

<210> SEQ ID NO 244
<211> LENGTH: 14
<212> TYPE: PRT
<213> ORGANISM: Artificial Sequence
<220> FEATURE:
<223> OTHER INFORMATION: TP925 FWII

<400> SEQUENCE: 244

Trp Phe Arg Gln Ala Pro Gly Lys Ala Arg Gln Ala Ile Leu
1               5                   10

<210> SEQ ID NO 245
<211> LENGTH: 8
<212> TYPE: PRT
<213> ORGANISM: Artificial Sequence
<220> FEATURE:
<223> OTHER INFORMATION: TP925 CDRII

<400> SEQUENCE: 245

Cys Ile Ser Ser Arg Gly Glu Thr
1               5

<210> SEQ ID NO 246
<211> LENGTH: 41
<212> TYPE: PRT
<213> ORGANISM: Artificial Sequence
<220> FEATURE:
<223> OTHER INFORMATION: TP925 FWIII

<400> SEQUENCE: 246

Thr Thr Tyr Gly Asp Ser Val Gln Gly Arg Phe Thr Ser Ser Arg Asp
1               5                   10                  15

Asn Ala Lys Asn Thr Ala Tyr Leu Gln Met Asn His Leu Lys Pro Glu
            20                  25                  30

Asp Thr Ala Val Tyr Tyr Cys Ala Ala
        35                  40

<210> SEQ ID NO 247
<211> LENGTH: 11
<212> TYPE: PRT
<213> ORGANISM: Artificial Sequence
```

```
<220> FEATURE:
<223> OTHER INFORMATION: TP925 FWIV

<400> SEQUENCE: 247

Trp Gly Lys Gly Thr Gln Val Thr Val Ser Ser
1               5                   10

<210> SEQ ID NO 248
<211> LENGTH: 25
<212> TYPE: PRT
<213> ORGANISM: Artificial Sequence
<220> FEATURE:
<223> OTHER INFORMATION: TP979 FWI

<400> SEQUENCE: 248

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 249
<211> LENGTH: 10
<212> TYPE: PRT
<213> ORGANISM: Artificial Sequence
<220> FEATURE:
<223> OTHER INFORMATION: TP979 CDRI

<400> SEQUENCE: 249

Gly Phe Thr Leu Asp Tyr Tyr Ala Ile Gly
1               5                   10

<210> SEQ ID NO 250
<211> LENGTH: 14
<212> TYPE: PRT
<213> ORGANISM: Artificial Sequence
<220> FEATURE:
<223> OTHER INFORMATION: TP979 FWII

<400> SEQUENCE: 250

Trp Phe Arg Leu Ala Pro Gly Lys Glu Arg Glu Gly Val Ser
1               5                   10

<210> SEQ ID NO 251
<211> LENGTH: 8
<212> TYPE: PRT
<213> ORGANISM: Artificial Sequence
<220> FEATURE:
<223> OTHER INFORMATION: TP979 CDRII

<400> SEQUENCE: 251

Cys Ile Ser Ser Ser Gly Gly Ser
1               5

<210> SEQ ID NO 252
<211> LENGTH: 41
<212> TYPE: PRT
<213> ORGANISM: Artificial Sequence
<220> FEATURE:
<223> OTHER INFORMATION: TP979 FWIII

<400> SEQUENCE: 252

Thr Asn Tyr Ala Asp Ser Val Lys Gly Arg Phe Thr Ile Ser Arg Asn
1               5                   10                  15

Asn Ala Lys Asn Thr Val Tyr Leu Gln Met Asn Ser Leu Lys Pro Glu
            20                  25                  30
```

-continued

```
Asp Thr Ala Val Tyr Tyr Cys Ala Leu
        35                  40

<210> SEQ ID NO 253
<211> LENGTH: 11
<212> TYPE: PRT
<213> ORGANISM: Artificial Sequence
<220> FEATURE:
<223> OTHER INFORMATION: TP979 FWIV

<400> SEQUENCE: 253

Trp Gly Gln Gly Thr Gln Val Thr Val Ser Ser
1               5                   10

<210> SEQ ID NO 254
<211> LENGTH: 25
<212> TYPE: PRT
<213> ORGANISM: Artificial Sequence
<220> FEATURE:
<223> OTHER INFORMATION: TP984 FWI

<400> SEQUENCE: 254

Gln Val Gln Leu Val Glu Ser Gly Gly Gly Leu Val Gln Gly Gly Gly
1               5                   10                  15

Ser Leu Arg Leu Ser Cys Ala Ala Ser
            20                  25

<210> SEQ ID NO 255
<211> LENGTH: 10
<212> TYPE: PRT
<213> ORGANISM: Artificial Sequence
<220> FEATURE:
<223> OTHER INFORMATION: TP984 CDRI

<400> SEQUENCE: 255

Arg Ser Ile Phe Ser Ile Asn Ala Met Gly
1               5                   10

<210> SEQ ID NO 256
<211> LENGTH: 14
<212> TYPE: PRT
<213> ORGANISM: Artificial Sequence
<220> FEATURE:
<223> OTHER INFORMATION: TP984 FWII

<400> SEQUENCE: 256

Trp Tyr Arg Gln Ala Leu Gly Lys Glu Arg Glu Leu Val Ala
1               5                   10

<210> SEQ ID NO 257
<211> LENGTH: 7
<212> TYPE: PRT
<213> ORGANISM: Artificial Sequence
<220> FEATURE:
<223> OTHER INFORMATION: TP984 CDRII

<400> SEQUENCE: 257

Ala Ile Ser Ser Gly Gly Ser
1               5

<210> SEQ ID NO 258
<211> LENGTH: 41
<212> TYPE: PRT
<213> ORGANISM: Artificial Sequence
<220> FEATURE:
<223> OTHER INFORMATION: TP984 FWIII
```

```
<400> SEQUENCE: 258

Thr Tyr Tyr Val Asp Ser Val Lys Gly Arg Phe Thr Ile Ser Arg Asp
1               5                   10                  15

His Val Lys Asn Thr Leu Tyr Leu Gln Met Asn Ser Leu Lys Pro Glu
            20                  25                  30

Asp Thr Ala Met Tyr Tyr Cys Ala Ala
        35                  40

<210> SEQ ID NO 259
<211> LENGTH: 11
<212> TYPE: PRT
<213> ORGANISM: Artificial Sequence
<220> FEATURE:
<223> OTHER INFORMATION: TP984 FWIV

<400> SEQUENCE: 259

Trp Gly Gln Gly Thr Gln Val Thr Val Ser Ser
1               5                   10

<210> SEQ ID NO 260
<211> LENGTH: 25
<212> TYPE: PRT
<213> ORGANISM: Artificial Sequence
<220> FEATURE:
<223> OTHER INFORMATION: TP924 FWI

<400> SEQUENCE: 260

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 261
<211> LENGTH: 10
<212> TYPE: PRT
<213> ORGANISM: Artificial Sequence
<220> FEATURE:
<223> OTHER INFORMATION: TP924 CDRI

<400> SEQUENCE: 261

Gly Phe Thr Phe Ser Ser Tyr Ala Met Thr
1               5                   10

<210> SEQ ID NO 262
<211> LENGTH: 14
<212> TYPE: PRT
<213> ORGANISM: Artificial Sequence
<220> FEATURE:
<223> OTHER INFORMATION: TP924 FWII

<400> SEQUENCE: 262

Trp Val Arg Gln Ala Pro Gly Lys Gly Leu Glu Trp Val Gly
1               5                   10

<210> SEQ ID NO 263
<211> LENGTH: 8
<212> TYPE: PRT
<213> ORGANISM: Artificial Sequence
<220> FEATURE:
<223> OTHER INFORMATION: TP924 CDRII

<400> SEQUENCE: 263

Asp Ile Asn Gly Val Gly Asn Tyr
1               5
```

-continued

```
<210> SEQ ID NO 264
<211> LENGTH: 41
<212> TYPE: PRT
<213> ORGANISM: Artificial Sequence
<220> FEATURE:
<223> OTHER INFORMATION: TP924 FWIII

<400> SEQUENCE: 264

Thr Tyr Tyr Ala Asp Ser Val Lys Gly Arg Phe Thr Ile Ser Arg Asp
1               5                   10                  15

Asn Ala Lys Asn Thr Leu Tyr Leu Gln Met Asn Asn Leu Lys Pro Glu
            20                  25                  30

Asp Thr Ala Val Tyr Tyr Cys Ala Pro
        35                  40

<210> SEQ ID NO 265
<211> LENGTH: 11
<212> TYPE: PRT
<213> ORGANISM: Artificial Sequence
<220> FEATURE:
<223> OTHER INFORMATION: TP924 FWIV

<400> SEQUENCE: 265

Trp Gly Gln Gly Thr Gln Val Thr Val Ser Ser
1               5                   10

<210> SEQ ID NO 266
<211> LENGTH: 25
<212> TYPE: PRT
<213> ORGANISM: Artificial Sequence
<220> FEATURE:
<223> OTHER INFORMATION: TP929 FWI

<400> SEQUENCE: 266

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 267
<211> LENGTH: 10
<212> TYPE: PRT
<213> ORGANISM: Artificial Sequence
<220> FEATURE:
<223> OTHER INFORMATION: TP929 CDRI

<400> SEQUENCE: 267

Gly Phe Thr Leu Asp Tyr Tyr Ala Ile Gly
1               5                   10

<210> SEQ ID NO 268
<211> LENGTH: 14
<212> TYPE: PRT
<213> ORGANISM: Artificial Sequence
<220> FEATURE:
<223> OTHER INFORMATION: TP929 FWII

<400> SEQUENCE: 268

Trp Phe Arg Gln Ala Pro Gly Lys Glu Arg Glu Gly Val Ser
1               5                   10

<210> SEQ ID NO 269
<211> LENGTH: 8
<212> TYPE: PRT
<213> ORGANISM: Artificial Sequence
```

-continued

```
<220> FEATURE:
<223> OTHER INFORMATION: TP929 CDRII

<400> SEQUENCE: 269

Cys Ile Ser Ser Ser Ser Gly Arg
1               5

<210> SEQ ID NO 270
<211> LENGTH: 41
<212> TYPE: PRT
<213> ORGANISM: Artificial Sequence
<220> FEATURE:
<223> OTHER INFORMATION: TP929 FWIII

<400> SEQUENCE: 270

Thr Asp Tyr Val Asp Ser Val Lys Gly Arg Phe Thr Ile Ser Arg Asp
1               5                   10                  15

Asn Ala Arg Asn Thr Val Tyr Leu Gln Met Asn Ser Leu Lys Pro Glu
            20                  25                  30

Asp Thr Ala Val Tyr Tyr Cys Ala Ala
        35                  40

<210> SEQ ID NO 271
<211> LENGTH: 11
<212> TYPE: PRT
<213> ORGANISM: Artificial Sequence
<220> FEATURE:
<223> OTHER INFORMATION: TP929 FWIV

<400> SEQUENCE: 271

Trp Gly Gln Gly Thr Gln Val Thr Val Ser Ser
1               5                   10
```